(12) United States Patent
Bürli et al.

(10) Patent No.: US 7,348,427 B2
(45) Date of Patent: *Mar. 25, 2008

(54) ANTIPATHOGENIC BENZAMIDE COMPOUNDS

(75) Inventors: Roland W. Bürli, Pasadena, CA (US); Jacob Kaizerman, South San Francisco, CA (US); Peter Jones, Bridgenorth (GB)

(73) Assignee: Genesoft Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/004,615

(22) Filed: Dec. 2, 2004

(65) Prior Publication Data

US 2006/0069034 A1 Mar. 30, 2006

Related U.S. Application Data

(63) Continuation of application No. 10/165,764, filed on Jun. 6, 2002, now abandoned.

(60) Provisional application No. 60/298,206, filed on Jun. 13, 2001, provisional application No. 60/342,309, filed on Dec. 21, 2001.

(51) Int. Cl.
*C07D 417/14* (2006.01)
*C07D 413/14* (2006.01)

(52) U.S. Cl. ............ 544/133; 544/141; 544/139; 544/140; 544/134; 544/137; 544/138

(58) Field of Classification Search ............ 544/141, 544/139, 140, 134, 133, 137, 138
See application file for complete search history.

(56) References Cited

U.S. PATENT DOCUMENTS

| | | | |
|---|---|---|---|
| 5,049,579 | A | 9/1991 | Lazzari et al. |
| 5,472,976 | A | 12/1995 | Animati et al. |
| 5,670,534 | A | 9/1997 | Animati et al. |
| 5,698,674 | A | 12/1997 | Bruice et al. |
| 5,753,629 | A | 5/1998 | Beria et al. |
| 5,808,087 | A | 9/1998 | Matsunaga et al. |
| 5,821,258 | A | 10/1998 | Matsunaga et al. |
| 5,852,011 | A | 12/1998 | Matsunaga et al. |
| 5,998,140 | A | 12/1999 | Dervan et al. |
| 6,090,947 | A | 7/2000 | Dervan et al. |
| 6,143,901 | A | 11/2000 | Dervan |
| 6,177,408 | B1 | 1/2001 | Cozzi et al. |
| 6,555,693 | B2 | 4/2003 | Ge et al. |
| 2003/0083268 | A1 | 5/2003 | Burli et al. |
| 2003/0199516 | A1* | 10/2003 | Moser et al. .......... 514/252.02 |

FOREIGN PATENT DOCUMENTS

| | | |
|---|---|---|
| JP | 8-269008 A2 | 10/1996 |
| WO | WO 93/13739 A2 | 7/1993 |
| WO | WO 94/20463 A1 | 9/1994 |
| WO | WO 97/03957 A1 | 2/1997 |
| WO | WO 97/28123 A1 | 8/1997 |
| WO | WO 98/21202 A1 | 5/1998 |
| WO | WO 98/35702 A1 | 8/1998 |
| WO | WO 98/37066 A1 | 8/1998 |
| WO | WO 98/37067 A1 | 8/1998 |
| WO | WO 98/37087 A1 | 8/1998 |
| WO | WO 98/45284 A1 | 10/1998 |
| WO | WO 98/49142 A1 | 11/1998 |
| WO | WO 98/50582 A1 | 11/1998 |
| WO | WO 98/52614 A2 | 11/1998 |
| WO | WO 99/50266 A1 | 10/1999 |
| WO | WO 99/64413 A1 | 12/1999 |
| WO | WO 00/06541 A1 | 2/2000 |
| WO | WO 00/06542 A1 | 2/2000 |
| WO | WO 00/15209 A2 | 3/2000 |
| WO | WO 00/15773 A2 | 3/2000 |
| WO | WO 02/00650 A2 | 1/2002 |

OTHER PUBLICATIONS

U.S. Appl. No. 60/322,704, filed Sep. 13, 2001, Moser et al.*
Acamone et al., 1986, "Synthesis, DNA binding and antiviral activity of distamycin analogues containing different heterocyclic moieties," *Anti-Cancer Drug Design* 1:235-244.
Bailly and Chaires, 1998, "Sequence-specific DNA minor groove binders. Design and synthesis of netropsin and distamycin analogues," *Bioconjugate Chemistry* 9(5):513-538.
Boger et al., 2000, "Total synthesis of distamycin A and 2640 analogues: A solution-phase combinatorial approach to the discovery of new, bioactive DNA binding agents and development of a rapid, high-throughput screen for determining relative DNA binding affinity or DNA binding sequence selectivity," *J. Am. Chem. Soc.* 122:6382-6394.
Ellervik et al., 2000, "Hydroxybenzamide/pyrrole pair distinguishes T-A from A-T base pairs in the minor groove of DNA," *J. Am. Chem. Soc.* 122:9354-9360.

(Continued)

Primary Examiner—Rebecca Anderson
(74) Attorney, Agent, or Firm—Townsend and Townsend and Crew LLP

(57) ABSTRACT

Antipathogenic benzamide compounds having the formula

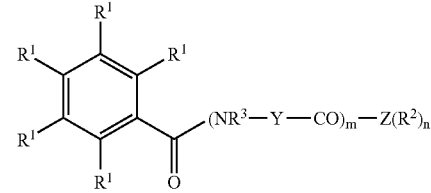

wherein at least one of the $R^1$ groups is F, Cl, CN or $CF_3$ and $R^2$, $R^3$, Y, Z, m, and n are as defined herein.

5 Claims, 6 Drawing Sheets

OTHER PUBLICATIONS

Figure 1A:
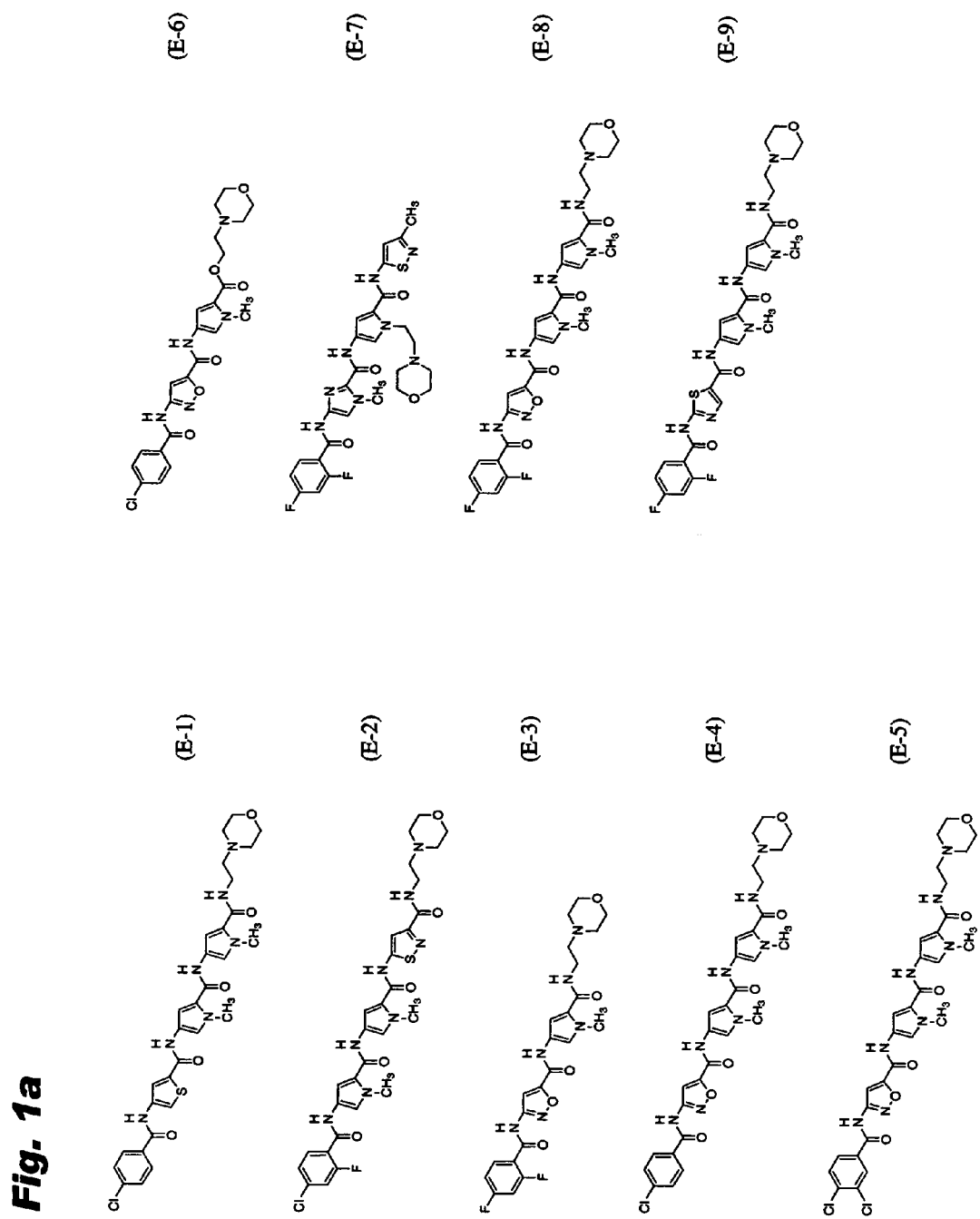

Floreancig et al., 2000, "Recognition of the minor groove of DNA by hairpin polyamides containing α-substituted-β-amino acids," *J. Am. Chem. Soc.* 122:6342-6350.

Kelly et al., 1996, "Binding site size limit of the 2:1 pyrrole-imidazole polyamide-DNA motif," *Proc. Natl. Acad. Sci. U.S.A.* 93:6981-6985.

Khalaf et al., 2000, "The synthesis of some head to head linked DNA minor groove binders," *Tetrahedron* 56:5225-5239.

Machon and Ryng, 1981, "Synthesis and biological properties of 5-benzoylamino-3-methyl-4-isoxazolocarboxylic acid derivatives," *Archivum Immunologiae et Therapiae Experimentalis* 29:813-821.

Mrksich et al., 1994, "Hairpin peptide motif. A new class of oligopeptides for sequence-specific recognition in the minor groove of double-helical DNA," *J. Am. Chem. Soc.* 116:7983-7988.

Neidle, S., 2001, "DNA minor-groove recognition by small molecules," *Natl. Prod. Rep.* 18:291-309.

Nielsen, P., 1991, "Sequence-selective DNA recognition by synthetic ligands," *Bioconjugate Chemistry* 2(1):1-12.

Plescia et al., 1994, "3α-hydroxysteroid dehydrogenase inhibitory activity of some N(3)-(1-R-4-carboxypyrazol-5-yl)-1,2,3-benzotriazin-4(3H)-one and quinazolin-4(3H)-one acids," *Il Farmaco* 47(7,8):505-507.

Rao et al., 1988, "Interaction of synthetic analogues of distamycin and netropsin with nucleic acids. Does curvature of ligand play a role in distamycin-DNA interactions?" *Biochemistry* 27(8):3018-3024.

Trauger et al., 1996, "Recognition of DNA by designed ligands at subnanomolar concentrations," *Nature* 382:559-561.

Wade et al., 1992, "Design of peptides that bind in the minor groove of DNA at 5'-(A,T)G(A,T)C(A,T)-3' sequences by a dimeric side-by-side motif," *J. Am. Chem. Soc.* 114:8784-8794.

White et al., 1997, "On the pairing rules for recognition in the minor groove of DNA by pyrrole-imidazole polyamides," *Chemistry & Biology* 4:569-578.

White et al., 1998, "Recognition of the four Watson-Crick base pairs in the DNA minor groove by synthetic ligands," *Nature* 391:468-471.

* cited by examiner

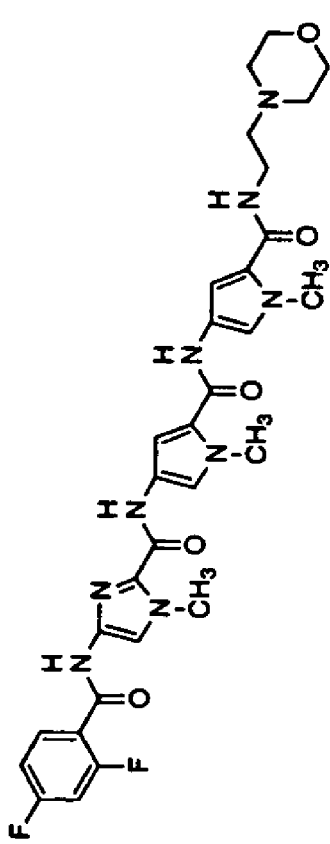

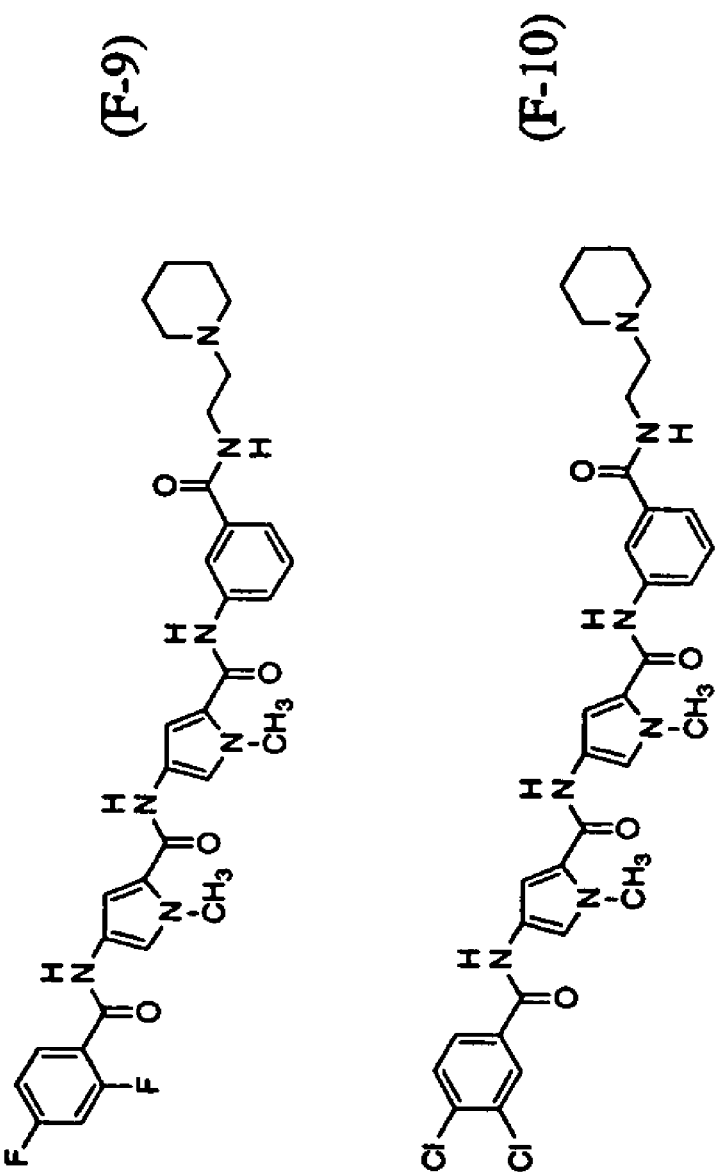

SEQUENCE LISTING

```
<160> NUMBER OF SEQ ID NOS: 7

<210> SEQ ID NO 1
<211> LENGTH: 310
<212> TYPE: DNA
<213> ORGANISM: Artificial Sequence
<220> FEATURE:
<223> OTHER INFORMATION: Description of Artificial Sequence:310 bp dsDNA
      EdoRI/PvuII restriction fragment from Plasmid A

<400> SEQUENCE: 1
aattcgagct cggtacccgg ggatcctcta gatgccgcta agtactatgc cgctaactac      60
tatgccgcta attactatgc cgctaaatac tatgccgcta actagtatgc cgctatgcag     120
gcatgcaagc ttggcgtaat catggtcata gctgtttcct gtgtgaaatt gttatccgct     180
cacaattcca cacaacatac gagccggaag cataaagtgt aaagcctggg gtgcctaatg     240
agtgagctaa ctcacattaa ttgcgttgcg ctcactgccc gctttccagt cgggaaacct     300
gtcgtgccag                                                            310

<210> SEQ ID NO 2
<211> LENGTH: 352
<212> TYPE: DNA
<213> ORGANISM: Artificial Sequence
<220> FEATURE:
<223> OTHER INFORMATION: Description of Artificial Sequence:352 bp dsDNA
      EdoRI/PvuII restriction fragment from Plasmid B

<400> SEQUENCE: 2
ctggcacgac aggtttcccg actggaaagc gggcagtgag cgcaacgcaa ttaatgtgag      60
ttagcgcgaa ttgatctggt ttgacagctt atcatcgact gcacggtgca ccaatgcttc     120
tggcgtcagg cagccatcgg aagctgtggt atggctgtgc aggtcgtaaa tcactgcata     180
attcgtgtcg ctcaaggcgc actcccgttc tggataatgt tttttgcgcc gacatcataa     240
cggttctggc aaatattctg aaatgagctg ttgacaatta atcatccggc tcgtataatg     300
```

```
tgtggaattg tgagcggata acaatttcac acaggaaaca gaccatggaa tt        352

<210> SEQ ID NO 3
<211> LENGTH: 56
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 3
ctagatgccg ctaagtacta tgccgctaac tactatgccg ctaattacta tgccgc     56

<210> SEQ ID NO 4
<211> LENGTH: 48
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 4
catagtaatt agcggcatag tagttagcgg catagtactt agcggcat             48

<210> SEQ ID NO 5
<211> LENGTH: 36
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 5
taaatactat gccgctaact agtatgccgc tatgca                          36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial
      Sequence:5'-phosphorylated complementary
      oligonucleotide for Plasmid A preparation

<400> SEQUENCE: 6
tagcggcata ctagttagcg gcatagtatt tagcgg                          36

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:Plasmid B
      target sequence

<400> SEQUENCE: 7
aattaatcat                                                       10
```

ANTIPATHOGENIC BENZAMIDE COMPOUNDS

CROSS REFERENCE TO RELATED APPLICATIONS

This application is a continuation of U.S. patent application Ser. No. 10/165,764, filed Jun. 6, 2002, now abandoned which claims benefit of Provisional Patent Application No. 60/342,309, filed Dec. 21, 2001 and 60/298,206 filed Jun. 13, 2001. The disclosures of which are incorporated herein by reference.

STATEMENT REGARDING FEDERALLY SPONSORED RESEARCH OR DEVELOPMENT

This invention was made with Government support under Grant No. N65236-99-1-5427 awarded by the Space and Naval Warfare Systems Command. The Government has certain rights in this invention.

BACKGROUND OF THE INVENTION

1. Field of the Invention

This invention relates to antipathogenic compounds and methods for their use.

2. Description of Related Art

A number of naturally occurring or synthetic compounds bind to double stranded nucleic acid, especially double stranded DNA ("dsDNA"). Some bind to the major groove, while others bind to the minor groove. Still others intercalate between adjacent base pairs. Combination binding modes are known, in which a compound has binding interactions with more than one nucleic acid site.

It has been proposed to use dsDNA binding compounds to regulate the expression of genes for medical purposes. If a disease is characterized by the overexpression or undesired expression of a gene (e.g., an oncogene), in principle the disease can be treated by suppressing wholly or partially the gene's expression via the binding of a compound to the gene or a promoter site thereof and interfering with transcription. Infections by pathogens such as fungi, bacteria, and viruses can be treated with compounds that interfere with the expression of genes essential for the pathogen's proliferation. Or, in a disease characterized by non- or under-expression of a beneficial gene, the expression of the beneficial gene can be up-regulated with a compound that binds to the binding site of a repressor, displacing the repressor.

The natural products distamycin and netropsin represent a class of DNA-binding compounds that has been studied over the years:

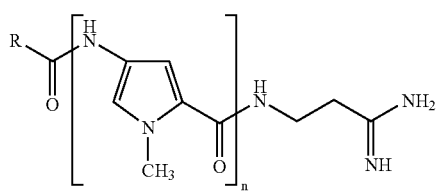

Distamycin: R = H
n = 3
Netropsin: R = H$_2$N(C=NH)NHCH$_2$
n = 2

Structurally, distamycin and netropsin are heteroaromatic polyamides, having as their core structural motif N-methylpyrrole carboxamide residues. They bind to the minor groove, their crescent molecular shapes providing a conformational fit within the groove. The binding occurs with a preference for A,T rich dsDNA tracts.

Many heteroaromatic polyamides have been synthesized elaborating on the distamycin/netropsin motif, with the objective of enhancing or varying biological activity, increasing binding affinity to dsDNA, and/or improving specificity in base pair sequence recognition. See Bailly et al., *Bioconjugate Chemistry* 1998, 9 (5), 513-538, and Neidle, *Nat. Prod. Rep.* 2001, 18, 291-309. The use of synthetic heteroaromatic polyamides in therapeutics has been proposed, for example, in Dervan et al., U.S. Pat. No. 5,998,140 (1999); Dervan et al., WO 00/15209 (2000); Dervan, WO 00/15773 (2000); and Gottesfeld et al., WO 98/35702 (1998).

BRIEF SUMMARY OF THE INVENTION

This invention provides benzamide compounds having the formula

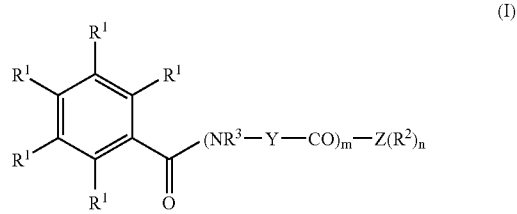

(I)

including the pharmaceutically acceptable salts thereof.

Each $R^1$ is independently H, F, Cl, CN, CF$_3$, OH, N(R$^2$)$_2$, OR$^2$ or a substituted or unsubstituted (C$_1$-C$_{12}$)alkyl group, or a substituted or unsubstituted (C$_1$-C$_{12}$)heteroalkyl group, with the proviso that at least one $R^1$ is F, Cl, CN, OCF$_3$, OCF$_2$H, or CF$_3$ (preferably F, Cl, or OCF$_2$H). Each $R^2$ and $R^3$ is independently H, a substituted or unsubstituted (C$_1$-C$_{12}$)alkyl group, or a substituted or unsubstituted (C$_1$-C$_{12}$) heteroalkyl group.

Each Y is independently a branched or unbranched, substituted or unsubstituted (C$_1$-C$_5$)alkylene group or a substituted or unsubstituted, aromatic or heteroaromatic ring system, wherein the ring system has at least one of a 5- or 6-member aromatic or heteroaromatic ring or fused 6,6 or 6,5 aromatic or heteroaromatic rings, with the proviso that at least one Y is a substituted or unsubstituted 5-member heteroaromatic ring.

Preferably, Y in the moiety —(NR$^3$—Y—CO)— immediately adjacent to

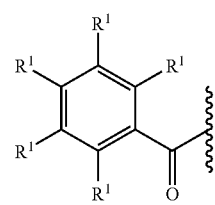

is a 5- or 6-member heteroaromatic ring.

Subscript m is an integer from 1 to 25, inclusive, preferably from 1 to 6, more preferably from 2 to 4.

Z is either O or N, with subscript n being 1 if Z is O and 2 if Z is N.

Compound (I) has at least one basic group having a $pK_b$ of 12 or less or a quaternized nitrogen group.

Preferably, each moiety —$(NR^3$—Y—CO)— is independently selected from the group consisting of:

(a) moieties $M^1$ having the formula

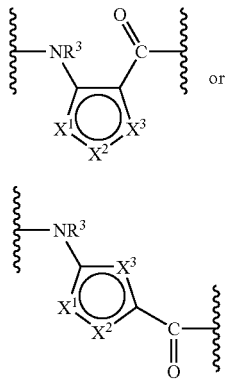

(IIa)

(IIb)

wherein one of $X^1$, $X^2$, and $X^3$ is a ring vertex selected from the group consisting of —O—, —S—, and —NR2—, and the other two of $X^1$, $X^2$, and $X^3$ are ring vertices selected from the group consisting of =N— and =$CR^4$—;

(b) moieties $M^2$ having the formula

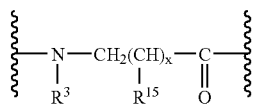

(III)

wherein x is 0 or 1 and each $R^{15}$ is independently H, OH, $NH_2$, or F;

(c) moieties $M^3$ having the formula

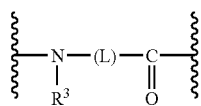

(IV)

wherein each L is independently a divalent moiety separating —NH— and —(C=O)— by 3 or 4 atoms; and (d) moieties $M^4$ having the formula

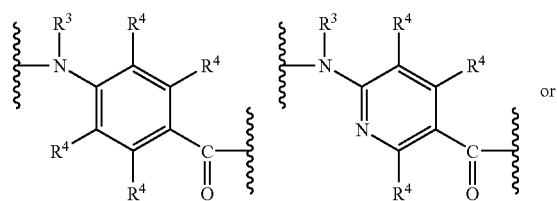

-continued

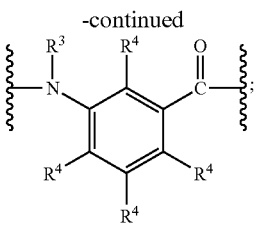

with the proviso that at least one moiety —$(NR^3$—Y—CO)— is a moiety $M^1$.

In the preceding formulae $M^1$ to $M^4$, $R^2$ and $R^3$ are as previously defined and each $R^4$ is independently H, F, Cl, Br, I, CN, OH, $NO_2$, $NH_2$, a substituted or unsubstituted ($C_1$-$C_{12}$)alkyl group, or a substituted or unsubstituted ($C_1$-$C_{12}$) heteroalkyl group.

Preferably, the moiety —$(NR^3$—Y—CO)— immediately adjacent to the residue

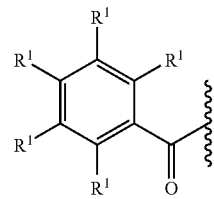

is a moiety $M^1$.

BRIEF DESCRIPTION OF THE DRAWING(S)

FIGS. 1a-1c, 2a-2b, and 3 illustrate compounds according to this invention.

DETAILED DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g. alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl, heteroalkyl, aryl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', ,—NR'—C(O)NR"R'", —S(O)$_2$R', —NH—C($NH_2$)=NH, —NR'C($NH_2$)=NH, —NH—C($NH_2$)=NR', —S(O)R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R"and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula —T—C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$)$_r$-B-, wherein A and B are independently —$CH_2$—, —O—, —NH—, —S—, —S(O)—, —S(O)$_2$), —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfiric, monohydrogensuifuric, hydriodic, or phosphorous acids and the like, as well as the salts derived from relatively nontoxic organic acids like acetic, ascorbic, propionic, isobutyric, maleic, malonic, lactic, malic, glutamic, benzoic, succinic, suberic, flimaric, mandelic, phthalic, benzenesulfonic, p-tolylsulfonic, citric, tartaric, methanesulfonic, lactobionic, and the like. Also included are salts of amino acids such as arginate and the like, and salts of organic acids like glucuronic or galactunoric acids and the like (see, for example, Berge, S. M., et al, "Pharmaceutical Salts", *Journal ofPharnaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (chiral centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

In the discussions below, reference is made to dsDNA as the nucleic acid, but it is to be understood that the invention is not limited to dsDNA and is applicable to other nucleic acids, i.e., ribonucleic acid.

Compounds

Compounds (I) of this invention are poly- or oligoamides having a benzamide unit and heteroaromatic carboxamide units.

Compounds (I) are believed to be DNA-binding compounds, which bind to the minor groove of dsDNA. Different polyamide-dsDNA binding modes are possible. In the simplest mode, often referred to as the 1:1 binding mode, a single polyamide molecule fits in the channel formed by the minor groove. In what is referred to as the 2:1 binding mode, two polyamide molecules fit side-by-side in the minor groove, preferably aligned in an antiparallel manner (i.e., with one polyamide being aligned N-to-C and the other polyamide being aligned C-to-N, where "C" and "N" refer to the carboxy and amino termini, respectively of the polyamides). Lastly, in what is referred to as a "hairpin" binding mode, a single polyamide molecule that has a more or less centrally positioned flexible moiety (i.e., a moiety $M^3$, as discussed in greater detail hereinbelow) folds around itself to adopt a hairpin conformation when it is bound to the minor groove, so that a first portion of the polyamide at one side of the hairpin turn is adjacent to a second portion of the polyamide at the other side of the hairpin turn.

In formula (I)

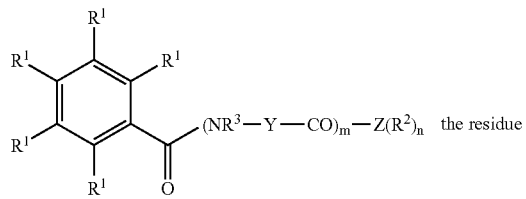

the residue

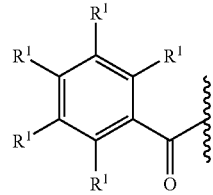

preferably is selected from the group consisting of

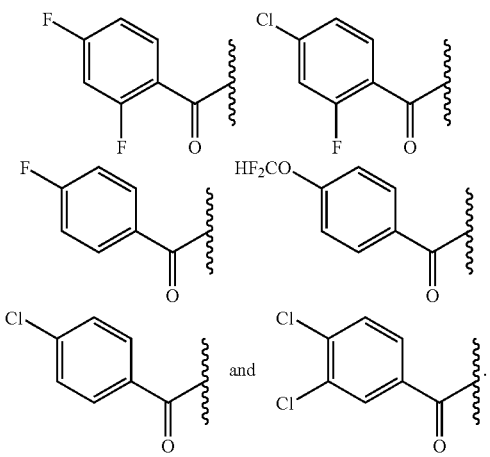

Moieties M¹, described by formulae IIa and IIb

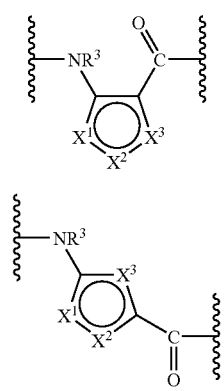

provide preferred heteroaromatic polyamide building blocks. Moieties M¹ are 5-membered ring heteroaromatic moieties, the selection of $X^1$, $X^2$, and $X^3$ determining the type of heteroaromatic ring. Exemplary heteroaromatic rings include imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene.

The circle in the five-membered rings of formulae IIa and IIb is meant to indicate the presence of two double bonds, which, in some embodiments, can move within the ring.

Preferred moieties M¹ are IIc (hereinafter "Py"), formally derived from 1-methyl-4-aminopyrrole-2-carboxylic acid, IId (hereinafter "Hp"), formally derived from 1-methyl-3-hydroxy4aminopyrrole-2-carboxylic acid, and IIe (hereinafter "Im"), formally derived from 1-methyl-4-aminoimidazole-2 carboxylic acid:

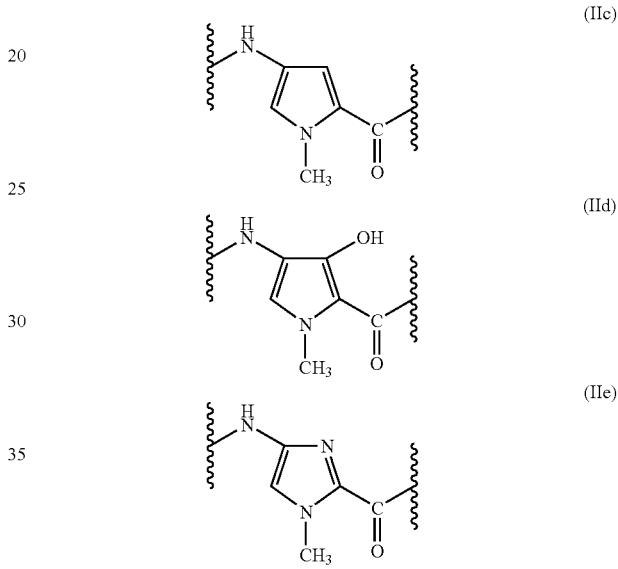

It has been shown by Dervan and co-workers (see, e.g., Dervan, U.S. Pat. No. 6,143,901 (2000); Dervan et al., WO 98/37066 (1998); White et al., Nature 391, 468 (1998); White et al., Chem. Biol. 1997, 4, 569) that, in a 2:1 binding mode to dsDNA, moieties Py, Im, and Hp moieties can be used to recognize specific dsDNA base pairs, giving rise to a set of "pairing rules" correlating heteroaromatic moiety pairs and DNA base pairs. These pairing rules are summarized below:

| Heteroaromatic Pair | dsDNA Base Pair(s) Recognized |
| --- | --- |
| Im/Py | G/C |
| Py/Im | C/G |
| Py/Py | A/T, T/A (degenerate) |
| Hp/Py | T/A |
| Py/Hp | A/T |

Such recognition can lead to sequence-specific dsDNA binding, enabling the design of compounds (I) that target predetermined DNA base pair sequences, for example, a specific promoter site or a sequence characteristic of a gene.

Optionally, compound (I) can include one or more moieties M²

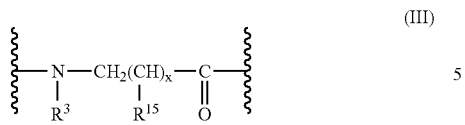
(III)

A moiety $M^2$ can function as a "spacer" for adjusting the positioning of the heteroaromatic moieties $M^1$ or $M^4$ relative to the dsDNA base pairs at the binding site. As a compound (I) binds in the minor groove, the alignment of heteroaromatic moieties $M^1$ and $M^4$ with the DNA base pairs with which they to interact of optimal binding or sequence recognition may drift as the number of heteroaromatic moieties $M^1$ and $M^4$ increases. Alternatively, incorporation of a moiety $M^2$ adds flexibility to compound (I), allowing its curvature to more accurately match that of the minor groove. The incorporation of one or more flexible moieties $M^2$ relaxes the curvature of the compound backbone, permitting larger compounds (I) to bind to longer sequences of DNA. In some preferred embodiments a moiety $M^2$ is present for every 4 to 5 heteroaromatic moieties $M^1$ or $M^4$, more preferably interrupting long sequences of $M^1$ and/or $M^4$ groups.

Preferred moieties $M^2$ are those corresponding to glycine (x=0 in formula III, depicted as IIIa below) and β-alanine (n=1 and $R^{15}$=H in formula III; depicted as IIIb below, hereinafter "β"), with the latter being especially preferred.

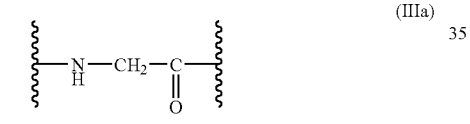
(IIIa)

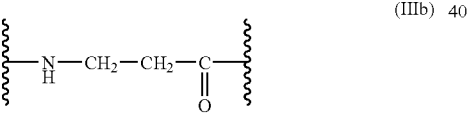
(IIIb)

Moieties $M^2$ in which x=1 and $R^{15}$=OH, $NH_2$, or F can be used to alter the binding affinity and specificity (relative to β-alanine), as disclosed in Floreancig et al., *J. Am. Chem. Soc.*, 2000, 122, 6342; the disclosure of which is incorporated herein by reference.

When present in compound (I), optional moieties $M^3$ (formula IV)

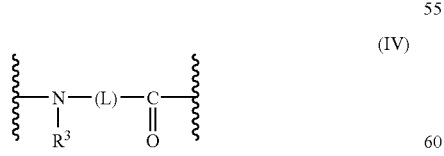
(IV)

have a group L providing a spacer of 3 to 4 atoms between —NH— and —C(=O)— and can be used to introduce a hairpin turn into compound (I). See Mrksich et al., *J. Am. Chem. Soc.* 1994, 116, 7983. Exemplary moieties $M^3$ include:

(IVa)

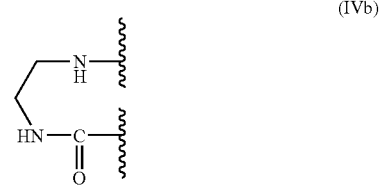
(IVb)

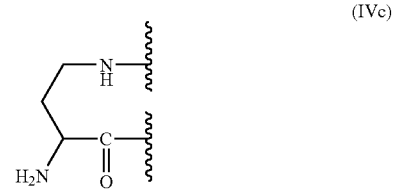
(IVc)

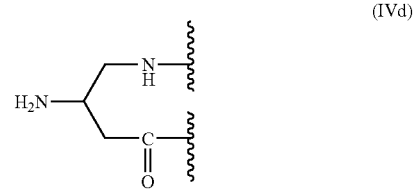
(IVd)

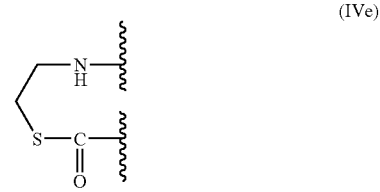
(IVe)

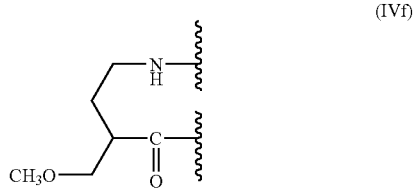
(IVf)

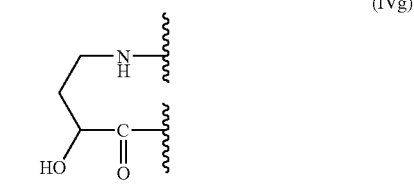
(IVg)

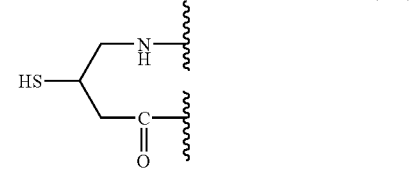
(IVh)

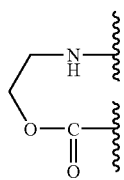 (IVi)

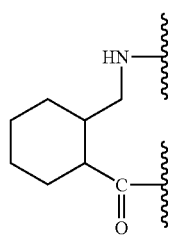 (IVj)

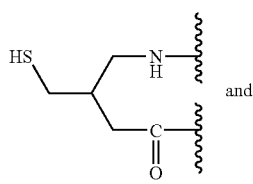 (IVk)

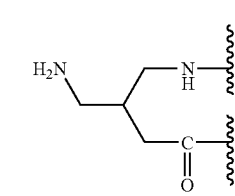 (IVl)

and

Moieties IVa (hereinafter "γ"), corresponding to γ-aminobutyric acid, and IVc, corresponding to 2,4-diaminobutyric acid, are preferred. Selecting one enantiomer or the other of moieties $M^3$ that are chiral allows stereochemical control of the binding of polyamides to the minor groove, for example as disclosed in Baird et al., WO 98/45284 (1998) in respect of R-2,4-diarninobutyric acid and S-2,4-diaminobutyric acid (corresponding to R-IVc and S-IVc, respectively).

Yet another class of moieties $M^3$ is represented by the formula

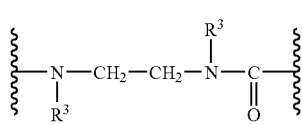

($R^3$ as previously defined)

While the group L preferably provides a 3-atom separation between the —NH— and the —(C=O)—, a 4-atom separation is also permissible, as illustrated by a 5-aminovaleric acid residue (i.e., L equals —(CH$_2$)$_4$—):

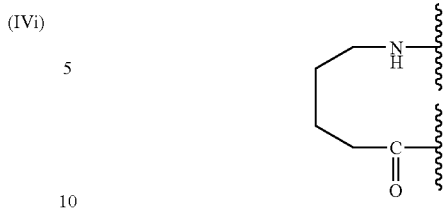

L can have pendant groups, which serve to enhance solubility or function as attachment points for other groups (e.g., IVc, IVd, IVg, IVh, IVk, IVl). The 3 to 4 atoms can be part of a larger group, which provides conformational rigidity (e.g., IVj). The 3 to 4 atoms can comprise carbon atoms only or it can include heteroatoms (e.g., IVb, IVe, IVi).

Moieties $M^4$ optionally can be used to introduce a aromatic or heteroaromatic residues other than $M^1$ into compound (I), in particular aryl-benzimidazole, pyridinyl carboxamide, or benzamide residues.

The group $Z(R^2)_n$ can be viewed as a terminal group, forming an amide or ester cap at the C-terminus of compound (I). In the case of Z=N, the two groups $R^2$ can be linked to each other to form a cyclic structure. A group $Z(R_2)_n$ can contain a basic group (as defined hereinbelow). Examples of suitable groups $Z(R^2)_n$ containing a basic group include:

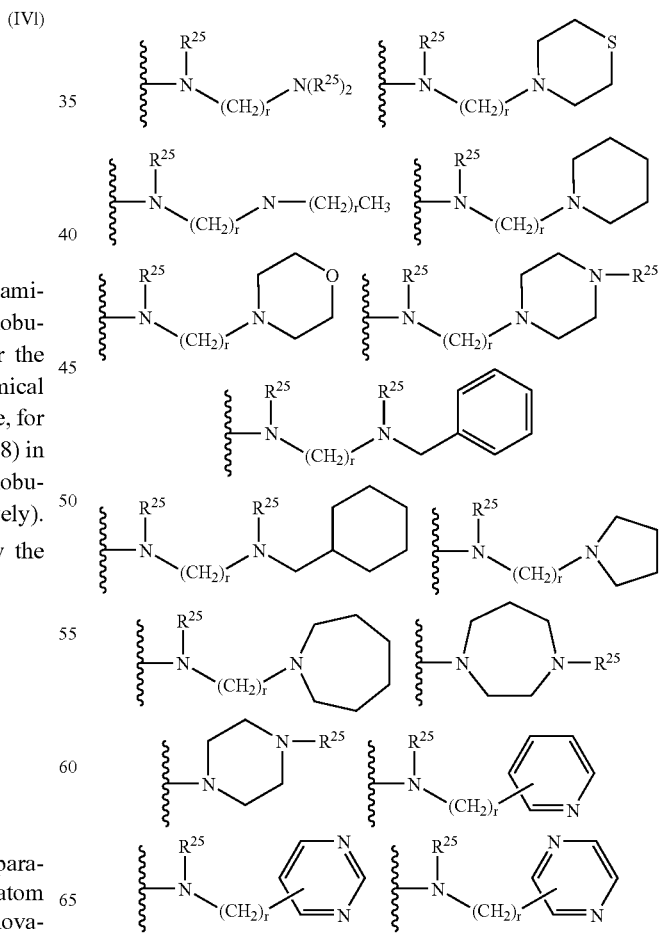

-continued

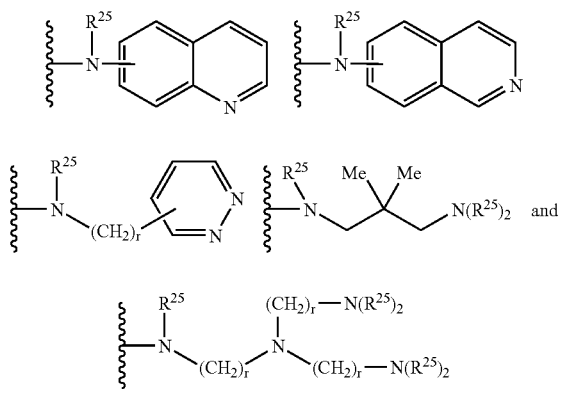

Examples of suitable groups $Z(R^2)_n$ not containing a basic group include:

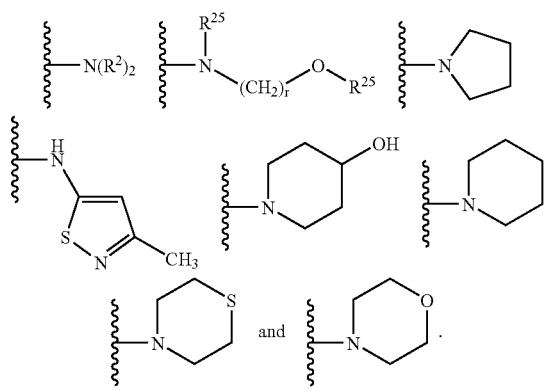

In the foregoing formulae, r is an integer ranging from 2 to 8, inclusive (preferably 2 to 6), and each $R^{25}$ is independently H, $CH_3$, $CH_2CH_3$, $CH_2CH_2CH_3$, or $CH(CH_3)_2$.

Compounds of this invention having such groups $Z(R^2)_n$ preferably have a basic group having a $pK_b$ of 12 or less or a quaternized nitrogen group located in a moiety $M^1$ or $M^4$ or in the N-terminal benzamide group.

The classification of the 5-amino-3-methylisothiazole group as a "nonbasic" $Z(R^2)_n$ group is somewhat arbitrary, as its $pK_b$ is marginal, normally around 12-13 (i.e., $pK_a$ 1-2) and depending on the molecular structure of the entire compound, it may qualify or not as a basic group as such is defined herein. Preferably, where a 5-amino-3-methylisothiazole is present, the compound has a basic group elsewhere in the molecule, for example pendant from a moiety $M^1$ or $M^4$, as exemplified by compounds C-21 to C-25, D-1, D-6, D-8, D-15 to D-24, D-28 to D-29, and E-7, infra.

The preceding illustrative formulae of basic and nonbasic groups $Z(R^2)_n$ have been drawn with Z as N and n as 2 for convenience. Those skilled in the art will appreciate that in these formulae the residue $NR^{25}$ can be replaced with O to give the corresponding groups $Z(R^2)_n$ in which Z is O and n is 1. Where Z is O, preferably the adjacent moiety Y is Py.

As used herein with reference to groups $R^2$ and $R^3$, "substituted or unsubstituted ($C_1$-$C_{12}$)alkyl group, or a substituted or unsubstituted ($C_1$-$C_{12}$)heteroalkyl group" includes not only conventional alkyl or cycloalkyl groups such as methyl, ethyl, propyl, isopropyl, butyl, s-butyl, isobutyl, t-butyl, cyclopentyl, cyclohexyl, and pentyl, but also unsaturated $C_1$ to $C_{12}$ groups, having for example aromatic, alkenyl, or alkynyl groups (e.g., phenyl, benzyl, vinyl, cyclohexenyl, etc.). One or more backbone carbons can be replaced by heteroatoms. There may be present functionalities such as hydroxy; oxo (=O); primary, secondary, or tertiary amine (e.g., —$NH_2$, —$NH(CH_3)$, —$N(CH_3)_2$); quaternary ammonium (e.g.,—$N(CH_3)_3^+$); alkoxy (e.g., methoxy, ethoxy); acyl (e.g., —C(=O)$CH_3$); amide (e.g., —NHC(=O)$CH_3$); thiol; thioether (e.g., —$SCH_3$); sulfoxide; sulfonamide (e.g., —$SO_2NHCH_3$); halogen (e.g., F, Cl); nitro; and the like. Exemplary specific $R^1$ and $R^2$ groups include methyl, trifluoromethyl, ethyl, acetyl, methoxy, methoxyethyl, ethoxyethyl, aminoethyl, hydroxyethyl, propyl, hydroxypropyl, cyclopropyl, isopropyl, 3-(dimethylamino)propyl, butyl, s-butyl, isobutyl, t-butyl, pentyl, cyclopentyl, vinyl, allyl, ethynyl, propynyl, and the like.

Compound (I) has a basic group having a $pK_b$ of 12 or less or a quaternized nitrogen group. (Or, stated conversely, the conjugate acid of the basic group has a $pK_a$ greater than 2 ($pK_a$=14−$pK_b$).) Preferably, the $pK_b$ is less than 10, more preferably less than 5. A $pK_b$ of less than 12 ensures that compound (I) is protonated under the conditions in which it interacts with a nucleic acid. Preferably the basic group is a nitrogenous group, for example an amine, an amidine, a guanidine, a pyridine, a pyridazine, a pyrazine, a pyrimidine, an imidazole, or an aniline. Primary, secondary, or tertiary aliphatic amines are preferred. Exemplary quaternized nitrogen groups include alkyl pyridinium and tetraalkyl ammonium groups such as:

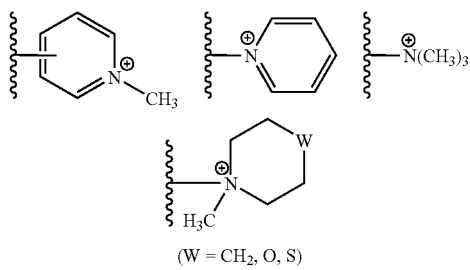

(W = $CH_2$, O, S)

A basic/quaternized nitrogen group may improve the transport of the compounds of this invention across cellular and nuclear membranes, to reach dsDNA in the nucleus. See Rothbard et al., WO 98/52614 (1998), which discloses that guanidine or amidino side chain moieties enhance transport across biological membranes. Another possible benefit is improved binding affinity to the nucleic acid, via ionic interactions with backbone phosphate groups. See Baird and Dervan, WO 98/37087 (1998) and Bruice et al., U.S. Pat. No. 5,698,674 (1997). Lastly, the protonated basic or quaternized nitrogen group increases solubility.

Preferably, the basic or quaternized nitrogen group is present within the C-terminal group $Z(R^2)_n$, but it may be present elsewhere in the molecule, for example as part of a group $R^1$ or $R^2$ in $M^1$ or $M^4$. Or, multiple basic or quaternized nitrogen groups may be present, at different locations on compound (I).

In a preferred embodiment, compound (I) is according to formula (Ia):

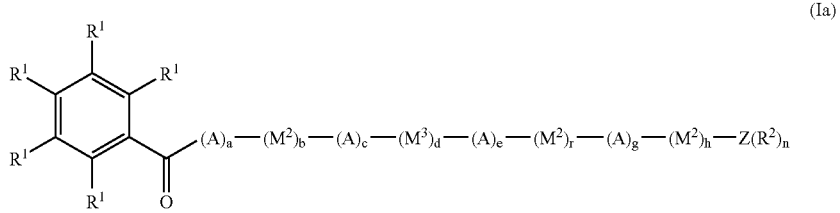

wherein $M_2$, $M^3$, $R^1$, $R^2$, Z and n have the same meanings as previously assigned; each A is independently $M^1$ or $M^4$; each of a, c, e, g and h is an integer independently from 0 to 4, inclusive; and each of b, d, and f is independently 0 or 1, with the proviso that at least one A is $M^1$. The sum of a, c, e, and g is preferably at least 2, more preferably at least 3. In another preferred embodiment, each of b, d, and f is 0.

In another preferred embodiment, compound (I) is according to formula (Ib):

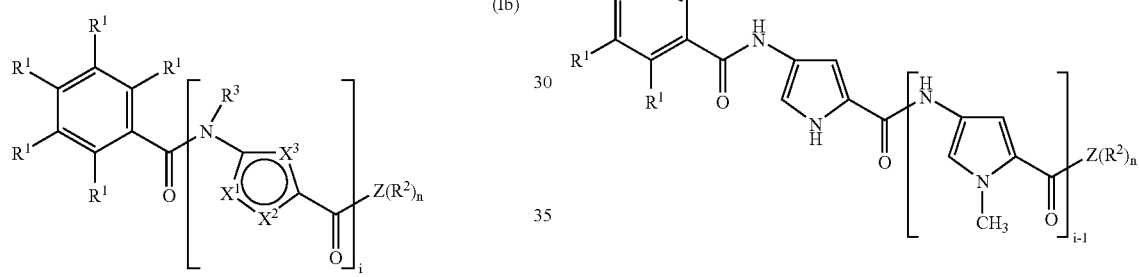

wherein $X^1$, $X^2$, $X^3$, $R^1$, $R^2$, $R^3$, Z, and n have the meanings previously assigned and i is an integer from 1 to 4, inclusive (preferably 2 or 3). In a preferred subgenus, the first 5-member heterocyclic ring (reading from left to right) is an unsubstituted pyrrole while subsequent 5-member heterocyclic rings are N-methylpyrroles, i.e., according to formula (Ic):

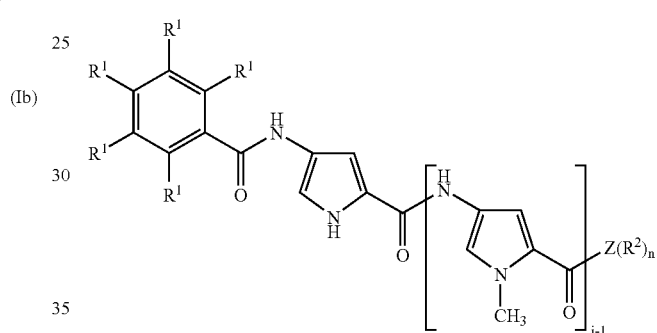

$R^1$, $R^2$, i, Z and n have the meanings assigned previously. Examples of compounds according to formula (Ic) are provided in Table A:

TABLE A

Illustrative Compounds (Ic)

| Compound Ref. | 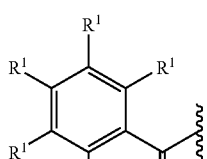 | i |  |
|---|---|---|---|
| A-1 | 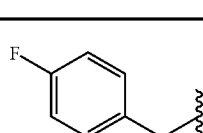 | 3 | 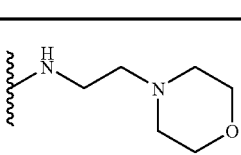 |
| A-2 | Same | 4 | Same |

TABLE A-continued

Illustrative Compounds (Ic)

| Compound Ref. | [aryl ketone structure with R¹ groups] | i | —Z(R²)ₙ |
|---|---|---|---|
| A-3 | 4-Cl, 2-F substituted phenyl ketone | 3 | Same |
| A-4 | Same | 3 | —NH—CH₂CH₂—N(piperidine) |
| A-5 | Same | 3 | —NH—CH₂CH₂—N(2,6-dimethylmorpholine) |
| A-6 | Same | 3 | —NH—CH₂CH₂—N(thiomorpholine) |
| A-7 | Same | 3 | —NH—CH₂CH₂—(4-pyridyl) |
| A-8 | Same | 3 | —NH—CH₂CH₂—N(4-hydroxypiperidine) |
| A-9 | Same | 3 | —NH—CH₂CH₂—N(pyrrolidine) |
| A-10 | Same | 3 | —NH—CH₂CH₂—N(2,6-dimethylpiperidine) |
| A-11 | Same | 3 | —NH—CH₂CH₂CH₂—N(4-hydroxypiperidine) |

TABLE A-continued

Illustrative Compounds (Ic)

| Compound Ref. | R¹-substituted phenyl ketone | i | $-Z(R^2)_n$ |
|---|---|---|---|
| A-12 | Same | 3 | –NH–CH₂CH₂–N(piperidine-4,4-diF) |
| A-13 | 4-Cl, 2-F phenyl ketone | 3 | –NH–(CH₂)₃–N(CH₃)₂ |
| A-14 | Same | 3 | –NH–CH₂–C(Me)₂–CH₂–N(Me)₂ |
| A-15 | Same | 3 | –NH–(CH₂)₄–N(CH₃)₂ |
| A-16 | Same | 3 | –NH–CH₂CH₂–N(C₂H₅)₂ |
| A-17 | Same | 2 | –NH–CH₂CH₂–morpholine |
| A-18 | Same | 2 | –NH–CH₂CH₂–piperidine |
| A-19 | Same | 2 | –NH–CH₂CH₂–pyrrolidine |
| A-20 | Same | 2 | –NH–CH₂CH₂–N(C₂H₅)₂ |
| A-21 | Same | 2 | –NH–CH₂CH₂–thiomorpholine |

TABLE A-continued

Illustrative Compounds (Ic)

| Compound Ref. | Ar(R¹)₄-C(O)- | i | -Z(R²)ₙ |
|---|---|---|---|
| A-22 | Same | 2 | -NH-CH₂CH₂-N(4,4-difluoropiperidin-1-yl) |
| A-23 | Same | 2 | -NH-CH₂CH₂-N(4-hydroxypiperidin-1-yl) |
| A-24 | Same | 3 | -NH-CH₂CH₂-(pyridin-3-yl) |
| A-25 | Same | 2 | -NH-CH₂CH₂-(pyridin-4-yl) |
| A-26 | 4-chloro-2-fluorophenyl-C(O)- | 3 | -NH-CH₂CH₂-N(4-fluoropiperidin-1-yl) |
| A-27 | Same | 4 | -NH-CH₂CH₂-(morpholin-4-yl) |
| A-28 | Same | 3 | -NH-CH₂CH₂-N⁺(CH₃)(morpholin-4-yl) |
| A-29 | Same | 3 | -NH-CH₂CH₂-(thiazolidin-3-yl) |
| A-30 | 3,4-dichlorophenyl-C(O)- | 3 | -NH-CH₂CH₂-(morpholin-4-yl) |

TABLE A-continued
Illustrative Compounds (Ic)
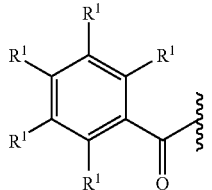
| Compound Ref. | | i | |
|---|---|---|---|
| A-31 | 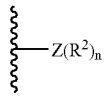 | 3 | Same |
| A-32 | 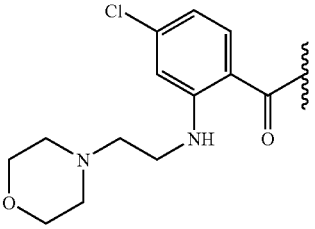 | 3 | Same |
| A-33 | 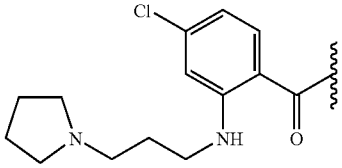 | 3 | Same |
| A-34 | 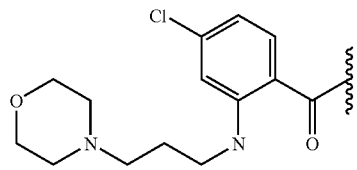 | 3 | Same |
| A-35 | 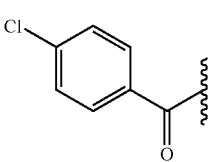 | 3 | Same |
In another preferred subgenus of compounds according to formula (Ib), each of the 5-member heterocylic rings is N-methyl pyrrole, i.e., according to formula (Id):
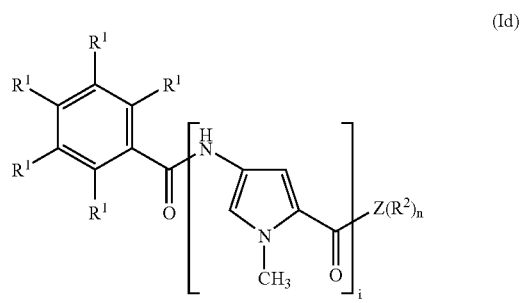
(Id)

$R^1$, $R^2$, i, Z and n have the meanings assigned previously. Examples of compounds according to formula Id are provided in Table B
TABLE B
Illustrative Compounds (Id)
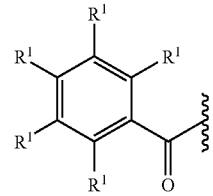
| Compound Ref. | | i | $-Z(R^2)_n$ |
|---|---|---|---|
| B-1 | 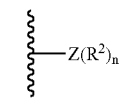 | 3 | 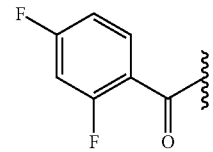 |
| B-2 | Same | 2 | Same |
| B-3 | Same | 3 | 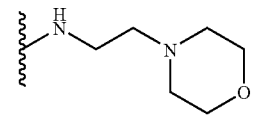 |
| B-4 | Same | 3 | 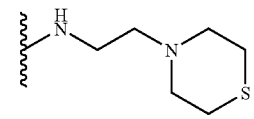 |
| B-5 | Same | 3 | 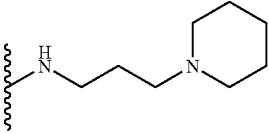 |
| B-6 | Same | 3 | 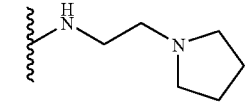 |
| B-7 | Same | 3 | 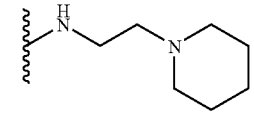 |
| B-8 | Same | 3 | 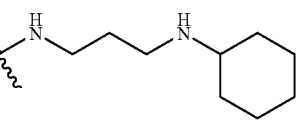 |
| B-9 | Same | 3 | 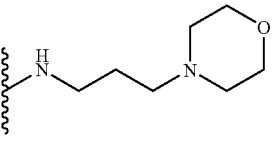 |
| B-10 | Same | 3 | 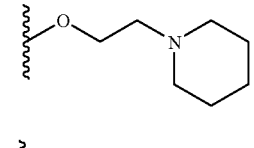 |

TABLE B-continued

Illustrative Compounds (Id)

| Compound Ref. | [R¹-substituted phenyl ketone] | i | —Z(R²)ₙ |
|---|---|---|---|
| B-11 | Same | 2 | —NH—CH₂CH₂—(thiomorpholin-4-yl) |
| B-12 | Same | 2 | —NH—CH₂CH₂—N(2,6-dimethylmorpholin-4-yl) |
| B-13 | Same | 2 | —NH—CH₂CH₂—N(CH₂CH₃)₂ |
| B-14 | Same | 2 | —NH—CH₂CH₂—(piperidin-1-yl) |
| B-15 | 2,4-difluorophenyl ketone | 2 | —NH—CH₂—C(Me)₂—CH₂—N(Me)₂ |
| B-16 | Same | 2 | —NH—CH₂CH₂—(pyrrolidin-1-yl) |
| B-17 | Same | 3 | —NH—CH₂CH₂—(1-methylpyridinium-2-yl) |
| B-18 | Same | 3 | —NH—CH₂CH₂—(azepan-1-yl) |
| B-19 | Same | 3 | —NH—CH₂CH₂—(4-hydroxypiperidin-1-yl) |

TABLE B-continued

Illustrative Compounds (Id)

| Compound Ref. | R¹-substituted phenyl ketone | i | —Z(R²)ₙ |
|---|---|---|---|
| B-20 | Same | 3 | —NH-CH₂CH₂-N(2,6-dimethylpiperidinyl) |
| B-21 | Same | 3 | —NH-CH₂CH₂-NH₂ |
| B-22 | Same | 3 | —NH-CH₂CH₂-(4-pyridyl) |
| B-23 | Same | 3 | —NH-CH₂CH₂-NH-C(=NH)NH₂ |
| B-24 | Same | 3 | —NH-CH₂CH₂-(3-pyridyl) |
| B-25 | Same | 3 | —NH-CH₂CH₂-N(CH₂CH₂OH)₂ |
| B-26 | Same | 3 | —N(4-hydroxypiperidinyl) |
| B-27 | Same | 3 | —NH-CH₂CH₂-N(4,4-difluoropiperidinyl) |
| B-28 | Same | 3 | —NH-CH₂CH₂-N(piperazinyl)NH |
| B-29 | 2,4-difluorophenyl ketone | 3 | —NH-CH₂CH₂-N(4-fluoropiperidinyl) |

TABLE B-continued

Illustrative Compounds (Id)

| Compound Ref. | (R¹ substituted phenyl ketone) | i | —Z(R²)ₙ |
|---|---|---|---|
| B-30 | Same | 3 | NH-CH₂CH₂-N⁺(CH₃)(morpholine) |
| B-31 | 3,4-difluorophenyl ketone | 3 | NH-CH₂CH₂-morpholine |
| B-32 | 4-fluorophenyl ketone | 3 | Same |
| B-33 | Same | 2 | NH-CH₂CH₂-thiomorpholine |
| B-34 | Same | 3 | Same |
| B-35 | Same | 4 | Same |
| B-36 | Same | 2 | NH-CH₂CH₂-morpholine |
| B-37 | Same | 4 | Same |
| B-38 | 3-fluorophenyl ketone | 3 | Same |
| B-39 | 2-fluorophenyl ketone | 3 | Same |
| B-40 | Same | 2 | NH-CH₂CH₂-thiomorpholine |
| B-41 | Same | 3 | Same |
| B-42 | Same | 4 | Same |

TABLE B-continued
Illustrative Compounds (Id)
| Compound Ref. | (aryl group) | i | Z(R²)ₙ |
|---|---|---|---|
| B-43 | Same | 2 |  —NH—CH₂CH₂—morpholine |
| B-44 | Same | 4 | 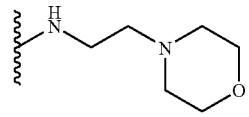 —NH—CH₂CH₂—morpholine |
| B-45 | 4-F, 2-Cl phenyl C(O)- | 3 | 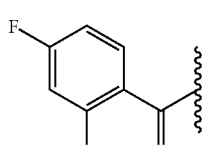 —NH—CH₂CH₂—morpholine |
| B-46 | 4-F, 3-Cl phenyl C(O)- | 3 | Same |
| B-47 | 4-Cl, 2-F phenyl C(O)- | 3 | Same |
| B-48 | Same | 2 | Same |
| B-49 | Same | 3 | 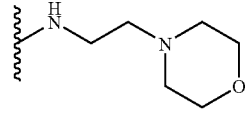 —NH—CH₂CH₂—thiomorpholine |
| B-50 | Same | 3 | 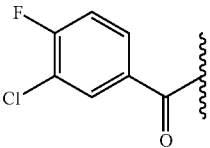 —NH—CH₂CH₂CH₂—N(CH₃)₂ |
| B-51 | 4-F, 2-(NH-CH₂CH₂CH₂-NH-cyclohexyl) phenyl C(O)- | 3 | —NH₂ |

TABLE B-continued

Illustrative Compounds (Id)

| Compound Ref. | R¹ substituted benzoyl group | i | —Z(R²)ₙ |
|---|---|---|---|
| B-52 | 2,6-dichlorobenzoyl | 3 | —NH-CH₂CH₂-morpholinyl |
| B-53 | 3,4-dichlorobenzoyl | 3 | Same |
| B-54 | Same | 2 | Same |
| B-55 | 2,4-dichlorobenzoyl | 3 | Same |
| B-56 | 4-chlorobenzoyl | 3 | Same |
| B-57 | Same | 2 | Same |
| B-58 | Same | 3 | —NH-CH₂CH₂-thiomorpholinyl |
| B-59 | 3-chlorobenzoyl | 3 | —NH-CH₂CH₂-morpholinyl |
| B-60 | 2-chlorobenzoyl | 3 | Same |
| B-61 | 4-hydroxy-2-chlorobenzoyl | 3 | Same |

TABLE B-continued

Illustrative Compounds (Id)

| Compound Ref. | (structure with R¹ substituted benzoyl) | i | —Z(R²)ₙ |
|---|---|---|---|
| B-62 | 4-chloro-2-hydroxybenzoyl 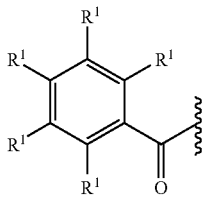 | 3 | Same |
| B-63 | 4-chloro-2-[(3-cyclohexylaminopropyl)amino]benzoyl 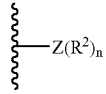 | 3 | —NH₂ 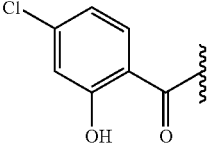 |
| B-64 | 4-chloro-2-[(2-piperidin-1-ylethyl)amino]benzoyl 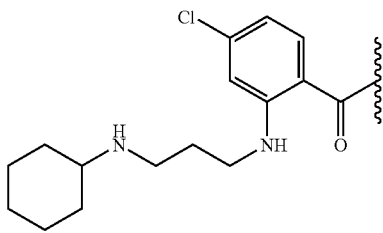 | 3 | —NH-CH₂CH₂-piperidinyl 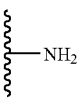 |
| B-65 | Same | 3 | —NH₂ 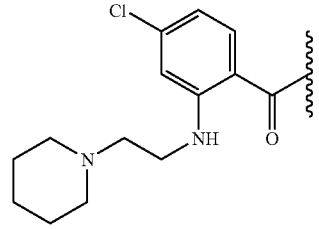 |
| B-66 | 4-chloro-2-[(2-morpholin-4-ylethyl)amino]benzoyl 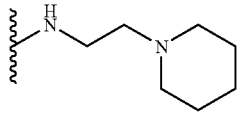 | 3 | Same |
| B-67 | 4-cyanobenzoyl 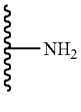 | 3 | —NH-CH₂CH₂-morpholinyl 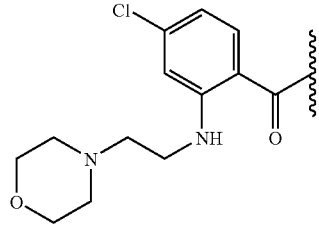 |
| B-68 | Same | 3 | —NH-CH₂CH₂-thiomorpholinyl 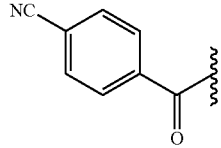 |

TABLE B-continued
Illustrative Compounds (Id)
| Compound Ref. | (aryl-C(O)-) | i | -Z(R²)ₙ |
|---|---|---|---|
| B-69 | Same | 2 | 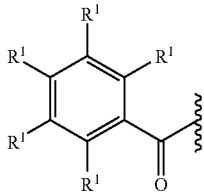 -NH-CH₂CH₂-morpholine |
| B-70 | 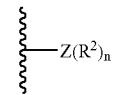 3-F₃C-C₆H₄-C(O)- | 3 | Same |
| B-71 | 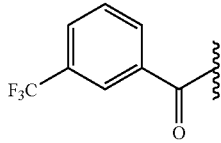 4-F₃C-C₆H₄-C(O)- | 3 | 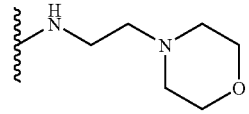 -NH-CH₂CH₂-morpholine |
| B-72 | 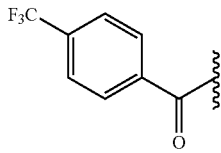 4-F₃CO-C₆H₄-C(O)- | 3 | Same |
| B-73 | 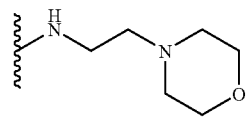 4-H₃CO-3-Cl-C₆H₃-C(O)- | 3 | Same |
| B-74 | 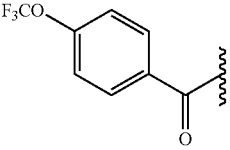 4-Cl-2-CH₃O-C₆H₃-C(O)- | 3 | Same |
| B-75 | 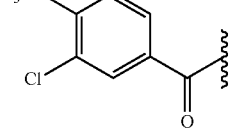 3-F₃CO-C₆H₄-C(O)- | 3 | Same |
| B-76 | 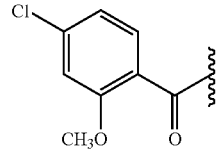 3,6-diCl-2-CH₃O-C₆H₂-C(O)- | 3 | Same |

TABLE B-continued
Illustrative Compounds (Id)
| Compound Ref. | 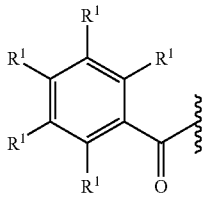 | i | —Z(R²)ₙ |
|---|---|---|---|
| B-77 | 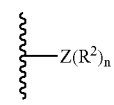 | 3 | Same |
| B-78 | 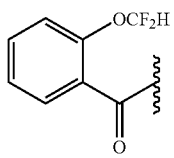 | 3 | Same |
| B-79 | 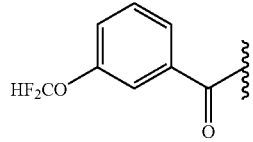 | 3 | Same |
| B-80 | 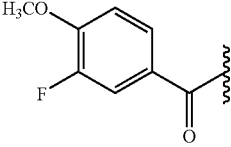 | 3 | Same |
| B-81 | 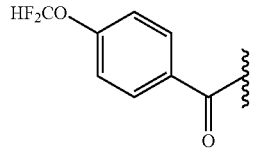 | 3 | Same |
| B-82 | 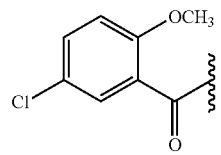 | 3 | 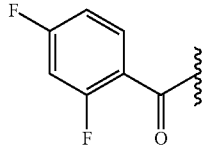 |
| B-83 | 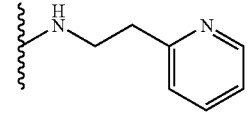 | 3 | 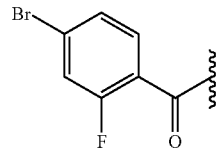 |

TABLE B-continued

Illustrative Compounds (Id)

| Compound Ref. | R¹ substituted phenyl-C(O)- | i | -Z(R²)ₙ |
|---|---|---|---|
| B-84 | 4-HF₂CO-C₆H₄-C(O)- | 3 | -NH-CH₂CH₂-(pyrrolidin-1-yl) |
| B-85 | Same | 3 | -NH-CH₂CH₂-(piperidin-1-yl) |
| B-86 | Same | 3 | -NH-CH₂CH₂-(thiomorpholin-4-yl) |

In another preferred subgenus of compounds within formula (Ib), each of the 5-member heterocycles is a pyrrole, as given by formula (Ie)

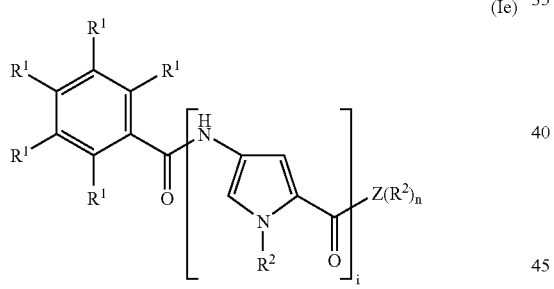

(Ie)

where $R^1$, $R^2$, i, Z, and n are as previously defined, with the proviso that at least one $R^2$ bonded to a pyrrole nitrogen is other than $CH_3$. Exemplary such compounds are shown in Table C. (In the column headed "$R^{2a}$, $R^{2b}$, $R^{2c}$, and $R^{2d}$," $R^{2a}$ represents the group $R^2$ attached to the first pyrrole ring (reading from left to right), $R^{2b}$ represents the group $R^2$ attached to the second pyrrole ring, and so forth. To illustrate, the first compound listed in Table C (C-1) is

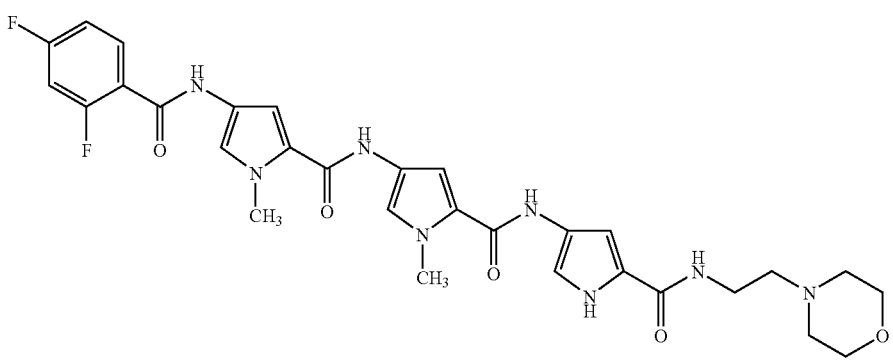

($R^{2d}$ is "n/a" for "not applicable," because there is no fourth pyrrole ring in this instance.)

TABLE C

Illustrative Compounds Ie

| Compound Ref. | (Ar group with R¹ substituents) | i | $R^{2a}$, $R^{2b}$, $R^{2c}$, and $R^{2d}$ | $Z(R^2)_n$ |
|---|---|---|---|---|
| C-1 | 2,4-difluorophenyl C(=O)– | 3 | $R^{2a} = R^{2b} = CH_3$, $R^{2c} = H$, $R^{2d} = n/a$ | –NH–CH$_2$CH$_2$–morpholinyl |
| C-2 | Same | 3 | $R^{2a} = CH_3$, $R^{2b} = H$, $R^{2c} = CH_3$, $R^{2d} = n/a$ | Same |
| C-3 | Same | 3 | $R^{2a} = R^{2b} = H$, $R^{2c} = CH_3$, $R^{2d} = n/a$ | Same |
| C-4 | Same | 3 | $R^{2a} = CH_3$, $R^{2b} = (CH_2)_3OH$, $R^{2c} = CH_3$, $R^{2d} = n/a$ | Same |
| C-5 | Same | 3 | $R^{2a} = H$, $R^{2b} = (CH_2)_3OH$, $R^{2c} = CH_3$, $R^{2d} = n/a$ | Same |
| C-6 | Same | 3 | $R^{2a} = (CH_2)_3OH$, $R^{2b} = R^{2c} = CH_3$, $R^{2d} = n/a$ | Same |
| C-7 | Same | 3 | $R^{2a} = CH_2OCH_3$, $R^{2b} = R^{2c} = CH_3$, $R^{2d} = n/a$ | Same |
| C-8 | 4-chloro-2-fluorophenyl C(=O)– | 3 | $R^{2a} = H$, $R^{2b} = CH_3$, $R^{2c} = H$, $R^{2d} = n/a$ | Same |
| C-9 | Same | 3 | $R^{2a} = H$, $R^{2b} = CH_3$, $R^{2c} = (CH_2)_3OH$, $R^{2d} = n/a$ | –NH–CH$_2$CH$_2$–piperidinyl |
| C-10 | Same | 3 | $R^{2a} = CH_3$, $R^{2b} = H$, $R^{2c} = CH_3$, $R^{2d} = n/a$ | –NH–CH$_2$CH$_2$–morpholinyl |
| C-11 | Same | 3 | $R^{2a} = CH_3$, $R^{2b} = H$, $R^{2c} = CH_3$, $R^{2d} = n/a$ | Same |
| C-12 | Same | 3 | $R^{2a} = H$, $R^{2b} = CH_2CH_3$, $R^{2c} = CH_3$, $R^{2d} = n/a$ | Same |
| C-13 | Same | 3 | $R^{2a} = H$, $R^{2b} = CH_2$–cyclopropyl, $R^{2c} = CH_3$, $R^{2d} = n/a$ | Same |
| C-14 | 4-chloro-2-fluorophenyl C(=O)– | 3 | $R^{2a} = H$, $R^{2b} = (CH_2)_3OH$, $R^{2c} = CH_3$, $R^{2d} = n/a$ | –NH–CH$_2$CH$_2$–morpholinyl |
| C-15 | Same | 3 | $R^{2a} = H$, $R^{2b} = (CH_2)_3OH$, $R^{2c} = CH_3$, $R^{2d} = n/a$ | Same |
| C-16 | Same | 3 | $R^{2a} = (CH_2)_3OH$, $R^{2b} = R^{2c} = CH_3$, $R^{2d} = n/a$ | Same |

TABLE C-continued

Illustrative Compounds Ie

| Compound Ref. | (R¹ substituted phenyl ketone) | i | R²ᵃ, R²ᵇ, R²ᶜ, and R²ᵈ | Z(R²)ₙ |
|---|---|---|---|---|
| C-17 | Same | 3 | $R^{2a}$ = CH$_2$OCH$_3$, $R^{2b}$ = $R^{2c}$ = CH$_3$, $R^{2d}$ = n/a | Same |
| C-18 | Same | 3 | $R^{2a}$ = CH$_3$, $R^{2b}$ = (CH$_2$)$_3$Cl, $R^{2c}$ = CH$_3$, $R^{2d}$ = n/a | Same |
| C-19 | Same | 3 | $R^{2a}$ = H, $R^{2b}$ = (CH$_2$)$_3$Cl, $R^{2c}$ = CH$_3$, $R^{2d}$ = n/a | Same |
| C-20 | 4-Cl, 2-(SCH$_2$CH$_3$) phenyl ketone | 4 | $R^{2a}$ = CH$_3$, $R^{2b}$ = (CH$_2$)$_3$SCH$_2$CH$_3$, $R^{2c}$ = $R^{2d}$ = CH$_3$ | Same |
| C-21 | 4-Cl, 2-(NH-CH$_2$CH$_2$-morpholino) phenyl ketone | 2 | $R^{2a}$ = CH$_3$, $R^{2b}$ = H, $R^{2c}$ = $R^{2d}$ = n/a | NH-(3-methylisothiazol-5-yl) |
| C-22 | 4-Cl, 2-(NH-CH$_2$CH$_2$-piperidino) phenyl ketone | 2 | $R^{2a}$ = CH$_3$, $R^{2b}$ = H, $R^{2c}$ = $R^{2d}$ = n/a | Same |
| C-23 | 4-Cl, 2-(NH-CH$_2$CH$_2$-pyrrolidino) phenyl ketone | 2 | $R^{2a}$ = CH$_3$, $R^{2b}$ = H, $R^{2c}$ = $R^{2d}$ = n/a | Same |

TABLE C-continued

Illustrative Compounds Ie

| Compound Ref. | (structure) | i | $R^{2a}$, $R^{2b}$, $R^{2c}$, and $R^{2d}$ | $Z(R^2)_n$ |
|---|---|---|---|---|
| C-24 | 4-Cl, 2-(HN-CH₂CH₂-thiomorpholinyl)phenyl ketone | 2 | $R^{2a} = CH_3$<br>$R^{2b} = H$<br>$R^{2c} = R^{2d} = n/a$ | Same |
| C-25 | 4-Cl, 2-(HN-CH₂CH₂CH₂-morpholinyl)phenyl ketone | 2 | $R^{2a} = CH_3$<br>$R^{2b} = H$<br>$R^{2c} = R^{2d} = n/a$ | Same |

In a preferred type of compounds (Ie), at least one $R^2$ bonded to a pyrrole ring has a basic group having a $pK_b$ of 12 or less or a quaternized nitrogen group. Exemplary such compounds are shown in Table D, with the column headed "$R^{2a}$, $R^{2b}$, $R^{2c}$, and $R^{2d}$" construed in the same manner as in Table C.

TABLE D

Illustrative Compounds Ie

| Compound Ref. | (structure) | i | $R^{2a}$, $R^{2b}$, $R^{2c}$, and $R^{2d}$ | $Z(R^2)_n$ |
|---|---|---|---|---|
| D-1 | 2,4-difluorophenyl ketone | 2 | $R^{2a} = CH_3$,<br>$R^{2b} = $ (CH₂)₃-morpholinyl<br>$R^{2c} = R^{2d} = n/a$ | NH-(3-methylisothiazol-5-yl) |
| D-2 | Same | 3 | $R^{2a} = R^{2b} = CH_3$,<br>$R^{2c} = (CH_2)_3N(CH_3)_2$, $R^{2d} = n/a$ | NH-CH₂CH₂-piperidinyl |

TABLE D-continued

Illustrative Compounds Ie

| Compound Ref. | 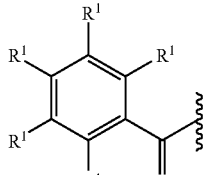 | i | $R^{2a}$, $R^{2b}$, $R^{2c}$, and $R^{2d}$ |  |
|---|---|---|---|---|
| D-3 | Same | 2 | $R^{2a} = CH_3$, $R^{2b} = (CH_2)_3N(CH_3)_2$, $R^{2c} = R^{2d} = n/a$ | 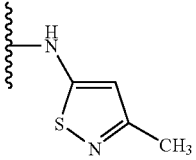 |
| D-4 | Same | 2 | $R^{2a} = H$<br>$R^{2b} =$ 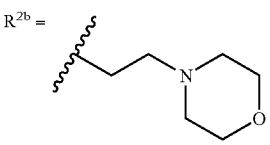<br>$R^{2c} = R^{2d} = n/a$ | Same |
| D-5 | Same | 3 | $R^{2a} = R^{2b} = CH_3$,<br>$R^{2c} =$ 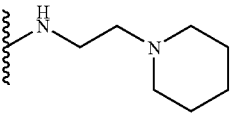<br>$R^{2d} = n/a$ | 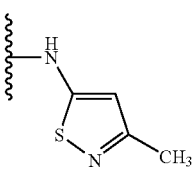 |
| D-6 | Same | 2 | $R^{2a} = CH_3$,<br>$R^{2b} = (CH_2)_3N^+(CH_3)_3$,<br>$R^{2c} = R^{2d} = n/a$ | 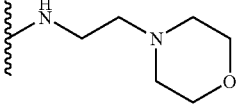 |
| D-7 | Same | 3 | $R^{2a} = —CH_3$, $R^{2b} = (CH_2)_3N(CH_3)_2$, $R^{2c} = CH_3$, $R^{2d} = n/a$ | 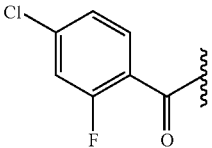 |
| D-8 | 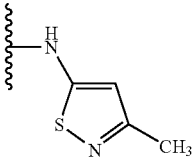 | 2 | $R^{2a} = CH_3$,<br>$R^{2b} =$ 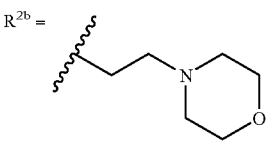<br>$R^{2c} = R^{2d} = n/a$ | |
| D-9 | Same | 2 | $R^{2a} = H$,<br>$R^{2b} =$ <br>$R^{2c} = R^{2d} = n/a$ | Same |
| D-10 | Same | 2 | $R^{2a} = H$, | Same |

TABLE D-continued

Illustrative Compounds Ie

| Compound Ref. | [R¹-phenyl-C(O)-] structure | i | $R^{2a}$, $R^{2b}$, $R^{2c}$, and $R^{2d}$ | $-Z(R^2)_n$ |
|---|---|---|---|---|
| | | | $R^{2b}$ = [CH₂CH₂CH₂-pyrrolidinyl] $R^{2c} = R^{2d}$ = n/a | |
| D-11 | 4-Cl, 2-F benzoyl | 2 | $R^{2a}$ = H, $R^{2b}$ = (CH₂)₃N(CH₃)₂, $R^{2c} = R^{2d}$ = n/a | -NH-(3-methylisothiazol-5-yl) |
| D-12 | Same | 2 | $R^{2a}$ = CH₃, $R^{2b}$ = (CH₂)₃N(CH₃)₂, $R^{2c} = R^{2d}$ = n/a | Same |
| D-13 | Same | 3 | $R^{2a}$ = H, $R^{2b}$ = CH₃, $R^{2c}$ = [CH₂CH₂CH₂-morpholinyl] $R^{2d}$ = n/a | -NH-CH₂CH₂-piperidinyl |
| D-14 | Same | 3 | $R^{2a}$ = H, $R^{2b}$ = CH₃, $R^{2c}$ = [CH₂CH₂CH₂-piperidinyl] $R^{2d}$ = n/a | Same |
| D-15 | Same | 2 | $R^{2a}$ = [CH₂CH₂CH₂N(CH₃)₂], $R^{2b}$ = H, $R^{2c} = R^{2d}$ = n/a | -NH-(3-methylisothiazol-5-yl) |
| D-16 | Same | 2 | $R^{2a}$ = [CH₂CH₂CH₂-pyrrolidinyl], $R^{2b}$ = H, $R^{2c} = R^{2d}$ = n/a | Same |
| D-17 | Same | 2 | $R^{2a}$ = [CH₂CH₂CH₂-piperidinyl], $R^{2b}$ = H, $R^{2c} = R^{2d}$ = n/a | Same |

TABLE D-continued

Illustrative Compounds Ie

| Compound Ref. | 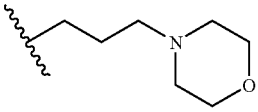 | i | $R^{2a}$, $R^{2b}$, $R^{2c}$, and $R^{2d}$ | 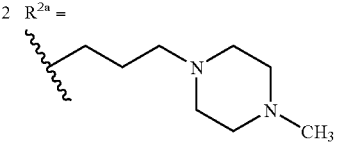 |
|---|---|---|---|---|
| D-18 | Same | 2 | $R^{2a}$ = 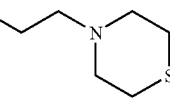<br><br>$R^{2b}$ = H, $R^{2c}$ = $R^{2d}$ = n/a | Same |
| D-19 | Same | 2 | $R^{2a}$ = 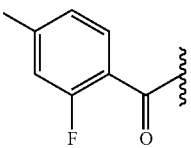<br><br>$R^{2b}$ = H, $R^{2c}$ = $R^{2d}$ = n/a | Same |
| D-20 | Same | 2 | $R^{2a}$ = 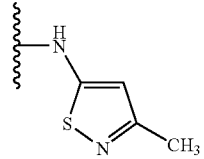<br><br>$R^{2b}$ = H, $R^{2c}$ = $R^{2d}$ = n/a | Same |
| D-21 | Same | 2 | $R^{2a}$ = $(CH_2)_3N(CH_2CH_2OH)_2$, $R^{2b}$ = H, $R^{2c}$ = $R^{2d}$ = n/a | Same |
| D-22 | Same | 2 | $R^{2a}$ = $CH_3$, $R^{2b}$ = $(CH_2)_3N^+(CH_3)_3$, $R^{2c}$ = $R^{2d}$ = n/a | Same |
| D-23 | 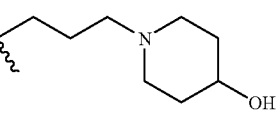 | 2 | $R^{2a}$ = H, $R^{2b}$ = $(CH_2)_3N^+(CH_3)_3$, $R^{2c}$ = $R^{2d}$ = n/a | 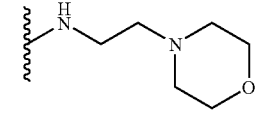 |
| D-24 | Same | 2 | $R^{2a}$ = 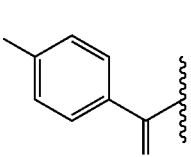<br><br>$R^{2b}$ = H, $R^{2c}$ = $R^{2d}$ = n/a | Same |
| D-25 | Same | 3 | $R^{2a}$ = $CH_3$, $R^{2b}$ = $(CH_2)_3N(CH_3)_2$, $R^{2c}$ = $CH_3$, $R^{2d}$ = n/a | 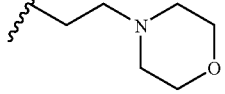 |
| D-26 | Same | 3 | $R^{2a}$ = H, $R^{2b}$ = $(CH_2)_3N(CH_3)_2$, $R^{2c}$ = $CH_3$, $R^{2d}$ = n/a | Same |
| D-27 | 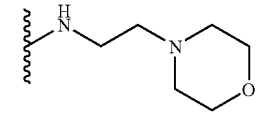 | 3 | $R^{2a}$ = $CH_3$,<br>$R^{2b}$ = (see structure)<br><br>$R^{2c}$ = $CH_3$, $R^{2d}$ = n/a | (same as D-25) |

TABLE D-continued

Illustrative Compounds Ie

| Compound Ref. | [aryl with R¹ groups and C=O] | i | R²ᵃ, R²ᵇ, R²ᶜ, and R²ᵈ | Z(R²)ₙ |
|---|---|---|---|---|
| D-28 | Same | 2 | R²ᵃ = CH₃, R²ᵇ = [propyl-morpholine], R²ᶜ = R²ᵈ = n/a | [isothiazole-CH₃ with NH] |
| D-29 | NC-phenyl-C(=O) | 2 | R²ᵃ = CH₃, R²ᵇ = [propyl-morpholine], R²ᶜ = R²ᵈ = n/a | Same |

However, the moieties

Figure 1B:
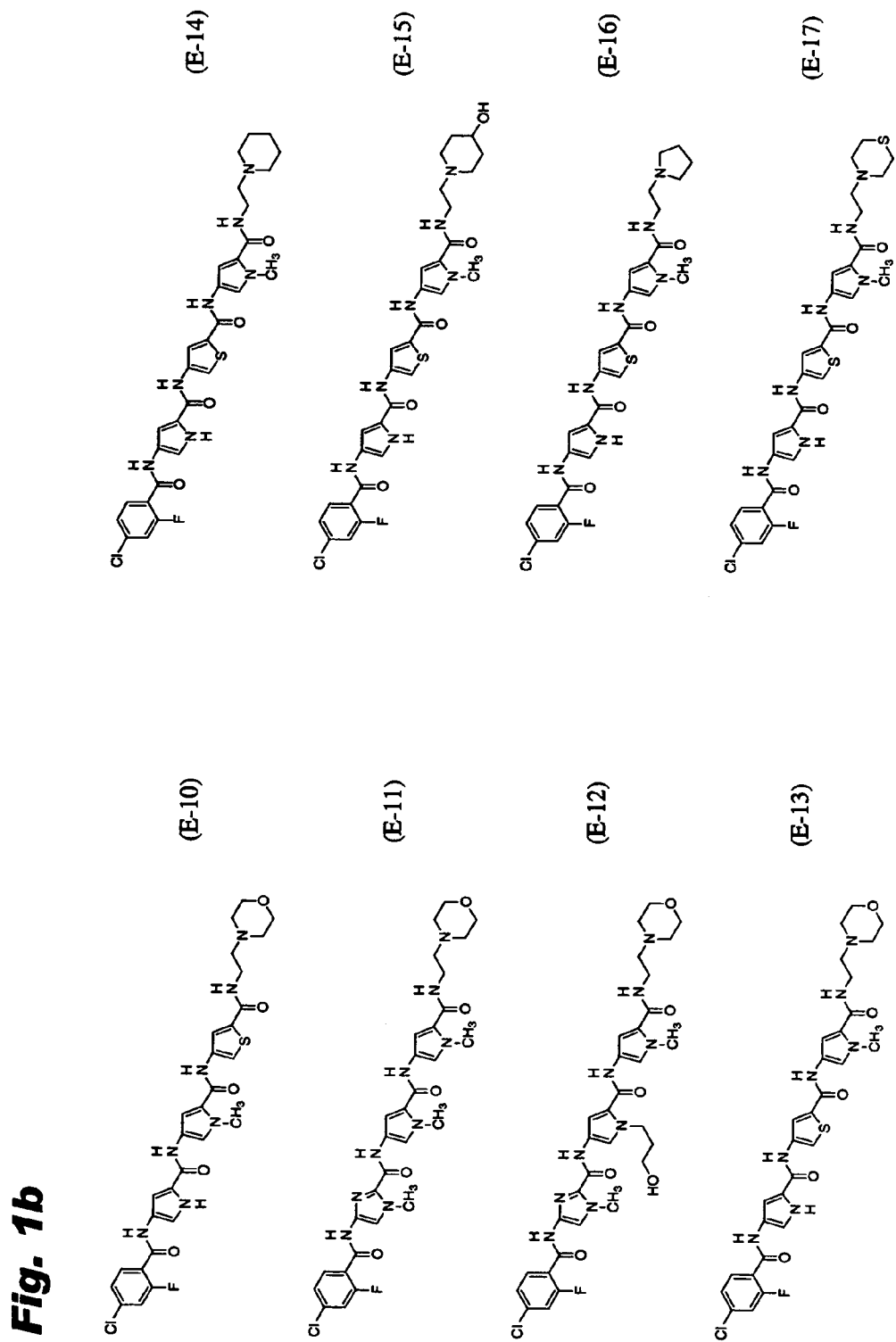

[structure with X¹, X², X³ heterocycle]

in formula (Ib) need not all be pyrrole carboxamides, as was in the instance of formulae (Ic), (Id), and (Ie). They can be other other than pyrrole, as illustrated in FIGS. 1a to 1c.

Preferred non-pyrrole 5-member ring heterocycles include:

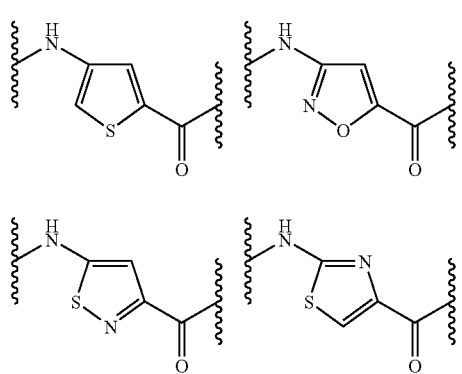

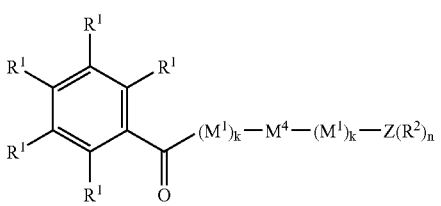

and

[imidazole structure]

(R² as defined above)

In yet another preferred embodiment, compounds (I) of this invention are according to formula (If):

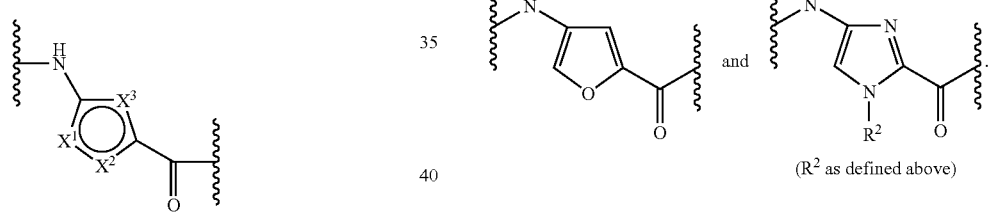

Figure 2A:
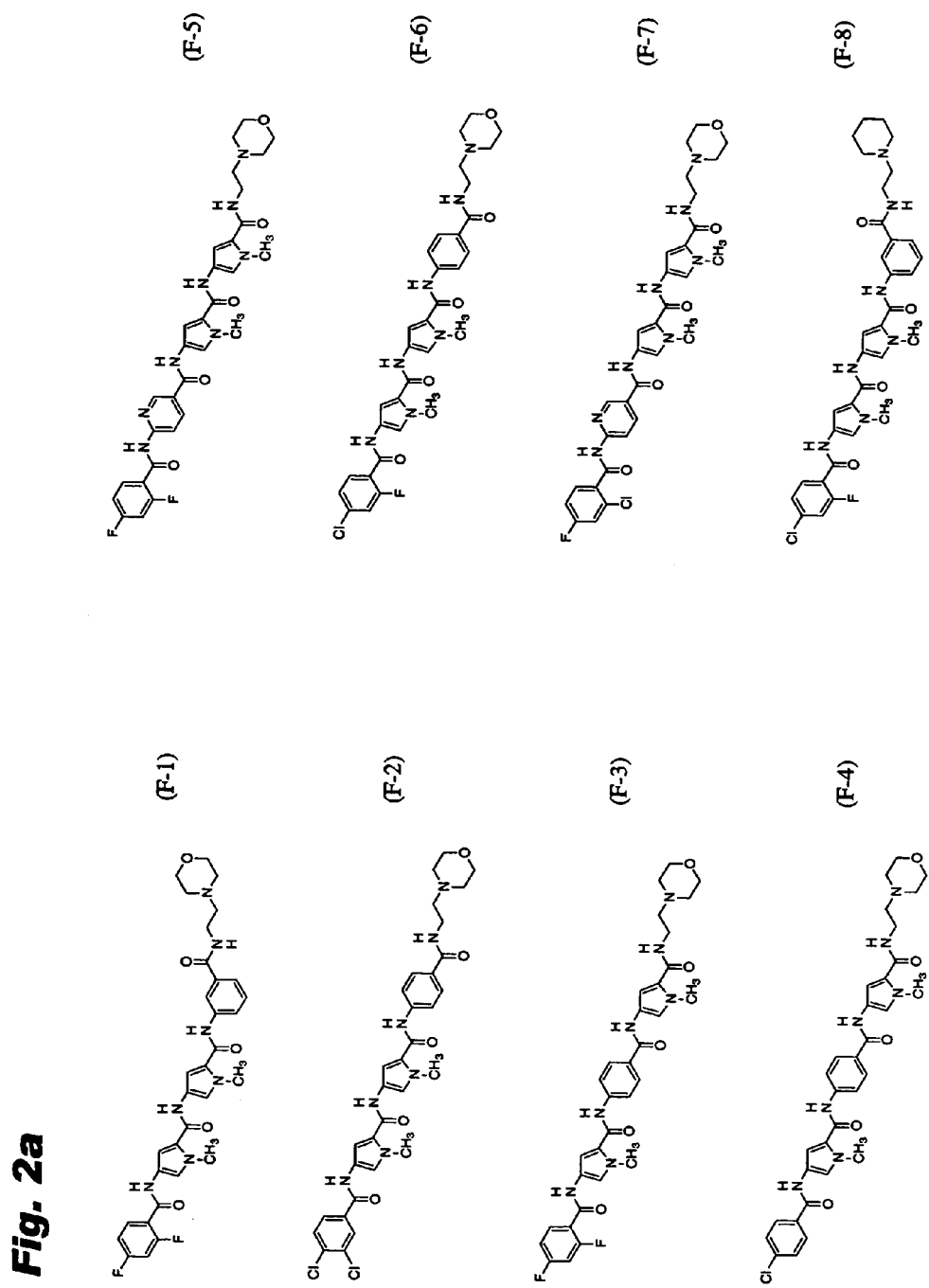

(If)

wherein M¹, M⁴, R¹, R², Z, and n are as previously defined and each k is independently an integer from 0 to 4, inclusive, with the proviso that at least one k is not 0. Illustrative compounds (If) are shown in FIGS. 2a through 2b.

Compounds (Ia), (Ib), (Ic), (Id), (Ie), and (If) have a basic group having a $pK_b$ of 12 or less or a quaternized nitrogen group.

Figure 3:
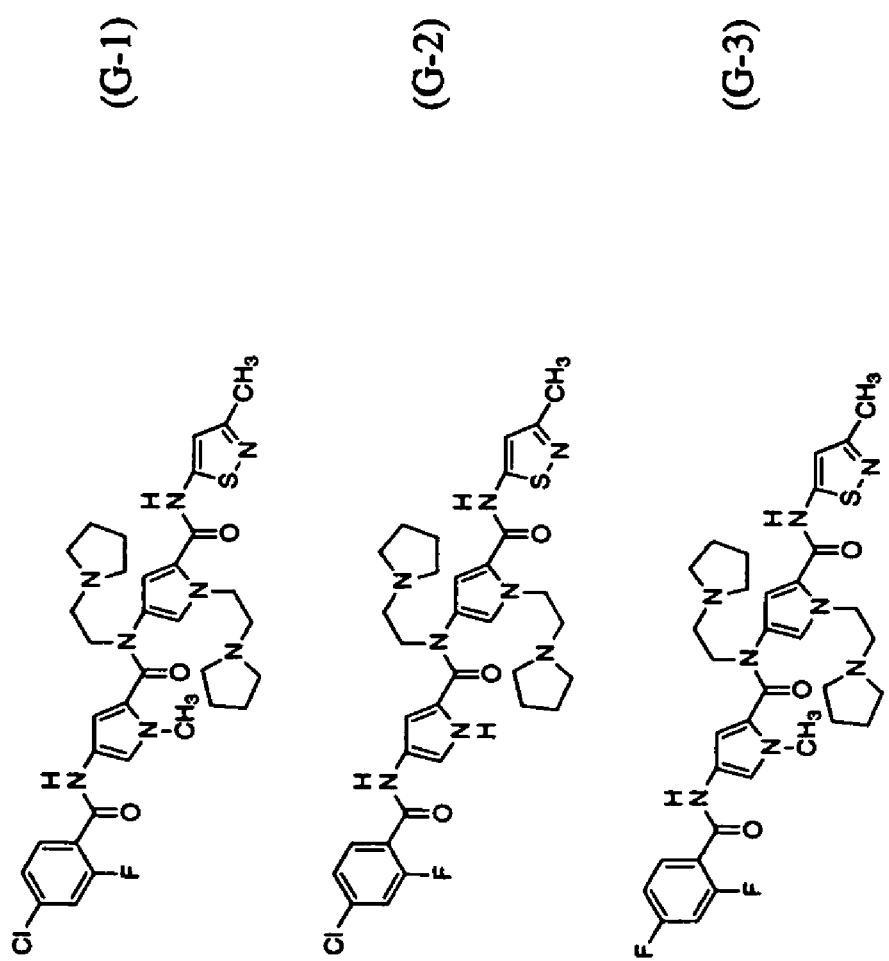

While it is normally preferred that the group R³ in —(NR³—Y—CO)— is H, such need not invariably be the case. R³ can be alkyl or alkylamino or alkylanmmonium, i.e., possessing a basic group having a $pK_b$ of 12 or less or a quaternary nitrogen group. Examples of such compounds are shown in FIG. 3.

Compounds (I) can be conjugated or linked to another nucleic acid binding compound. The conjugated nucleic acid binding compounds can be two identical or different compounds (I), or one compound (I) and a different class of nucleic acid binder, for example an intercalator, a triple helix former, a binder to the phosphate backbone, a major groove binder, another type of minor groove binder, and the like. A preferred site for forming the conjugating link is an amino, hydroxy, or thiol functionality in a group L in moiety $M^2$, which can be acylated or alkylated. The preparation of tandem linked nucleic acid binding polyamides in this manner is disclosed in Baird et al., WO 98/45284 (1998), the disclosure of which is incorporated herein by reference.

Compounds (I) also can be conjugated to other moieties, such as, peptides, proteins, transport agents, fluorophores or other reporter groups, and the like.

Compounds (I) preferably bind to dsDNA with high affinity, meaning an equilibrium association constant of at least $10^3$ $M^{-1}$, more preferably at least $10^6$ $M^{-1}$, and most preferably at least $10^9$ $M^{-1}$. The measurement of binding affinities by quantitative DNase I footprinting is disclosed in Dervan, WO 98/50582 (1998), and Trauger et al., Nature 382, 559 (8 Aug. 1996); the disclosures of which are incorporated herein by reference.

Compounds of this invention can be used to form complexes with dsDNA, for the purpose of recognizing and/or isolating dsDNA strands containing particular base-pair sequences, for example for analytical or diagnostic purposes. Thus, in another aspect of this invention there is provided a complex between dsDNA and compound of this invention. In cellular systems or in living organisms, they can modulate the expression of a gene by binding to the gene or a promoter or repressor region thereof. Such modulation may be useful for therapeutic or research purposes.

Additionally, compounds of this invention have been found to have anti-bacterial and/or antifungal properties and therefore may be used for combating (i.e., preventing and/or treating) infections in eukaryotic organisms. Other pathogens against which compounds of this invention can be useful include protozoa and viruses. For human anti-infective applications, an effective amount of a compound of this invention is used, optionally in combination with a pharmaceutically acceptable carrier. The composition may be dry, or it may be a solution. Treatment may be reactive, for combating an existing infection, or prophylactic, for preventing infection in an organism susceptible to infection. Preferably, compounds of this invention are used to treat infections by drug-resistant strains of bacteria, for example MRSA (methycillin resistant S. aureus), MRSE (methycillin resistant S. epidermidis), PRSP (penicillin resistant S. pneumoniae) or VRE (vancomycin resistant Enterococci). By "drug-resistant" it is meant that the bacteria are resistant to treatment with conventional antibiotics.

Host organisms that can be treated include eukaryotic organisms, in particular plants and animals. The plant may be an agriculturally important crop, such as wheat, rice, corn, soybean, sorghum, and alfalfa. Animals of interest include mammals such as bovines, canines, equines, felines, ovines, porcines, and primates (including humans). Thusly, in another aspect of this invention, there is provided a method for treating a bacterial infection—particularly an infection by Gram-positive bacteria—comprising administering to a patient in need of such treatment an effective amount of compound (I). Compounds of this invention can be used in the preparation of a medicament for treating a bacterial infection in a mammal. The compounds may be administered orally, topically, or parenterally (e.g., intravenously, subcutaneously, intraperitoneally, transdermally).

While not wishing to be bound by any particular theory, it is believed that the compounds of this invention derive their biological activity from their ability to bind to dsDNA.

Compounds I can be synthesized by solid phase techniques from the corresponding amino acids or their derivatives, for instance IIc', IId', and IIe' for the synthesis of the Py, Hp, and Im building blocks, respectively.

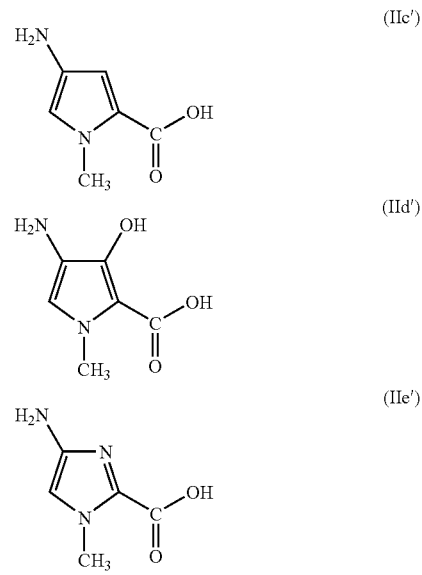

In solid phase synthesis, a polyamide is synthesized on a resin such as Boc-glycine-PAM-resin or Boc-β-alanine-PAM-resin, with moieties Y being added in series of steps involving amino-protected and carboxy-activated monomers, as taught in Dervan et al., U.S. Pat. No. 6,090,947 (2000) (the "'947 patent"); Baird et al., WO 98/37066 (1998); Baird et al., WO 98/37067 (1998); and Dervan et al., WO 98/49142 (1998); Baird et al., U.S. Provisional Appl'n No. 60/286,454, filed Apr. 26, 2001 (the "'454 application"); McMinn, U.S. Provisional Appl'n No. 60/298,206, filed Jun. 13, 2001 (the "'206 application"); Ge et al., U.S. Appl'n No. 09/808,729, filed Mar. 14, 2001 (the "'729 application"); Kelly et al., Proc. Nat'l Acad. Sci. USA, July 1996, 93, 6981 ("Kelly"); and Wade et al., J. Am. Chem. Soc., 1992, 114, 8783 ("Wade"); the disclosures of which are incorporated herein by reference.

The practice of this invention may be further understood by reference to the following examples, which are provided by way of illustration and not of limitation.

In Vitro Biolopical Activity

In vitro biological activity data were collected for a variety of microorganisms, including Bacillus cereus (ATCC 11778), Staphylococcus aureus (ATCC 27660, a methicillin resistant strain (MRSA); ATCC 13709, a methicillin sensitive strain (MSSA)); Streptococcus pneumoniae (ATCC 51422, a penicillin resistant strain (PRSP)), Enterococcus faecium (ATCC 51559, a vancomycin resistant strain (VRE)), and Staphylococcus epidermidis (ATCC 12228). Additionally, antifungal activity data were collected for Candida albicans (ATCC 38247).

Compounds according to this invention were screened for their in vitro activities against selected species of bacteria and fungi. The minimal inhibition concentration (MIC) of these compounds was determined using the National Committee for Clinical Laboratory Standards (NCCLS) broth microdilution assay in microtiter plates, as set forth in: (1) the guidelines of the National. Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifungal assays, the method recommended in Murray, P R., 1995 *Manual of Clinical Microbiology* (ASM Press, Washington, D.C.), was employed.

Preferably, compounds of this invention have an MIC of 4 or less against at least one strain of drug resistant bacteria. The results are presented in Table E below, which is keyed as follows:

TABLE E

In Vitro Biological Activity

| Cpd. Ref. | Organism (Minimum Inhibitory Concentration (MIC), µg/mL) | | | | | | | | |
|---|---|---|---|---|---|---|---|---|---|
| | A | B | C | D | E | F | G | H | I |
| A-1 | +++ | >32 | +++ | ND | +++ | ++ | ND | +++ | ND |
| A-2 | +++ | >32 | ++ | + | ND | + | + | ND | ND |
| A-3 | +++ | + | +++ | +++ | +++ | +++ | +++ | +++ | +++ |
| A-4 | +++ | ++ | + | +++ | +++ | +++ | +++ | +++ | +++ |
| A-5 | + | >32 | +++ | ND | +++ | +++ | ND | ++ | ND |
| A-6 | +++ | >32 | +++ | +++ | +++ | +++ | +++ | +++ | +++ |
| A-7 | +++ | >32 | +++ | +++ | +++ | +++ | +++ | +++ | +++ |
| A-8 | +++ | + | +++ | +++ | +++ | +++ | +++ | +++ | +++ |
| A-9 | +++ | + | +++ | +++ | +++ | +++ | +++ | + | +++ |
| A-10 | +++ | ++ | ++ | ND | +++ | +++ | ND | +++ | ND |
| A-11 | + | + | + | ND | ++ | + | ND | + | ND |
| A-12 | +++ | >32 | +++ | +++ | +++ | + | +++ | +++ | +++ |
| A-13 | +++ | +++ | ++ | + | +++ | +++ | +++ | +++ | +++ |
| A-14 | +++ | + | +++ | ND | +++ | +++ | ND | +++ | ND |
| A-15 | +++ | + | +++ | ND | +++ | +++ | ND | +++ | ND |
| A-16 | +++ | +++ | +++ | +++ | +++ | +++ | +++ | +++ | +++ |
| A-17 | + | >32 | +++ | ND | ++ | ++ | ND | +++ | ND |
| A-18 | +++ | >32 | +++ | +++ | +++ | +++ | +++ | +++ | +++ |
| A-19 | + | >32 | +++ | ND | ++ | +++ | ND | +++ | ND |
| A-20 | + | >32 | +++ | ND | ++ | ++ | ND | +++ | ND |
| A-21 | +++ | >32 | +++ | +++ | +++ | +++ | +++ | +++ | +++ |
| A-22 | +++ | >32 | +++ | +++ | +++ | +++ | +++ | +++ | +++ |
| A-23 | + | >32 | + | ND | + | + | ND | +++ | ND |
| A-24 | +++ | >32 | ++ | ND | >32 | +++ | ND | +++ | ND |
| A-25 | ++ | >32 | +++ | ND | +++ | +++ | ND | +++ | ND |
| A-26 | +++ | ++ | +++ | ND | +++ | +++ | ND | +++ | ND |
| A-27 | +++ | >32 | ++ | ND | + | + | ND | +++ | ND |
| A-28 | +++ | +++ | ++ | + | +++ | +++ | +++ | +++ | +++ |
| A-29 | +++ | >32 | + | ND | +++ | ++ | ND | +++ | ND |
| A-30 | +++ | >32 | +++ | ND | +++ | +++ | ND | +++ | ND |
| A-34 | +++ | + | ++ | ND | ND | ND | ND | + | ND |
| A-35 | +++ | >32 | +++ | ND | +++ | +++ | ND | +++ | ND |
| B-1 | +++ | >32 | +++ | +++ | +++ | +++ | +++ | +++ | +++ |
| B-2 | ++ | >32 | +++ | ND | ND | ND | ND | +++ | ND |
| B-3 | +++ | >32 | +++ | + | +++ | +++ | +++ | +++ | +++ |
| B-4 | ++ | >32 | ++ | ND | ++ | ++ | ND | ++ | ND |
| B-5 | +++ | >32 | +++ | ND | +++ | +++ | ND | +++ | ND |
| B-6 | +++ | >32 | +++ | +++ | +++ | +++ | +++ | +++ | +++ |
| B-7 | +++ | >32 | +++ | ND | +++ | +++ | ND | +++ | ND |
| B-8 | ++ | >32 | ++ | ND | ++ | ++ | ND | ++ | ND |
| B-9 | +++ | >32 | +++ | ND | +++ | +++ | ND | +++ | ND |
| B-10 | +++ | >32 | +++ | ND | + | + | ND | +++ | ND |
| B-11 | +++ | >32 | +++ | +++ | +++ | +++ | +++ | +++ | +++ |
| B-12 | +++ | >32 | +++ | ND | ++ | +++ | ND | +++ | ND |
| B-13 | + | >32 | ++ | ND | ++ | + | ND | +++ | ND |
| B-14 | ++ | >32 | +++ | ND | +++ | +++ | ND | +++ | ND |
| B-15 | >32 | >32 | >32 | ND | >32 | >32 | ND | + | ND |
| B-16 | ++ | >32 | +++ | ND | ++ | ++ | ND | +++ | ND |

TABLE E-continued

In Vitro Biological Activity

| Cpd. Ref. | Organism (Minimum Inhibitory Concentration (MIC), µg/mL) | | | | | | | | |
|---|---|---|---|---|---|---|---|---|---|
| | A | B | C | D | E | F | G | H | I |
| B-17 | +++ | >32 | + | ND | ++ | ++ | ND | ++ | ND |
| B-18 | +++ | ++ | +++ | +++ | +++ | +++ | +++ | +++ | +++ |
| B-19 | +++ | >32 | +++ | ND | +++ | +++ | ND | +++ | ND |
| B-20 | +++ | >32 | + | ND | +++ | ++ | ND | +++ | ND |
| B-21 | + | + | ++ | ND | + | ++ | ND | ++ | ND |
| B-22 | +++ | >32 | +++ | +++ | +++ | +++ | +++ | +++ | +++ |
| B-23 | +++ | ++ | +++ | ND | +++ | +++ | ND | +++ | ND |
| B-24 | +++ | >32 | +++ | +++ | +++ | +++ | +++ | +++ | +++ |
| B-25 | + | >32 | + | ND | + | + | ND | +++ | ND |
| B-26 | >32 | >32 | >32 | >32 | >32 | >32 | >32 | >32 | >32 |
| B-27 | +++ | >32 | +++ | +++ | +++ | +++ | +++ | +++ | +++ |
| B-28 | + | >32 | + | ND | + | + | ND | +++ | ND |
| B-29 | +++ | + | +++ | ND | +++ | +++ | ND | +++ | ND |
| B-30 | +++ | + | >32 | ND | +++ | +++ | ND | +++ | ND |
| B-31 | ++ | >32 | +++ | ND | ND | ND | ND | +++ | ND |
| B-32 | + | >32 | ++ | ND | ++ | + | ND | ++ | ND |
| B-33 | + | >32 | ++ | ND | ++ | + | ND | +++ | ND |
| B-34 | +++ | >32 | +++ | ND | +++ | +++ | ND | +++ | ND |
| B-35 | +++ | >32 | +++ | ND | +++ | +++ | ND | +++ | ND |
| B-36 | >32 | >32 | >32 | + | >32 | >32 | ND | + | >32 |
| B-37 | +++ | >32 | +++ | ND | +++ | >32 | ND | +++ | ND |
| B-38 | + | >32 | + | ND | ND | ND | ND | + | ND |
| B-39 | +++ | >32 | +++ | ND | +++ | ++ | ND | +++ | ND |
| B-40 | ++ | >32 | +++ | ND | ++ | ++ | ND | +++ | ND |
| B-41 | +++ | >32 | +++ | +++ | +++ | +++ | +++ | +++ | +++ |
| B-42 | +++ | >32 | +++ | ND | +++ | +++ | ND | +++ | ND |
| B-43 | + | >32 | + | ND | + | + | ND | + | ND |
| B-44 | +++ | >32 | ++ | ND | +++ | ++ | ND | +++ | ND |
| B-45 | ++ | >32 | ++ | ND | ND | ND | ND | +++ | ND |
| B-46 | +++ | >32 | +++ | ND | ND | ND | ND | +++ | ND |
| B-47 | +++ | >32 | +++ | +++ | ND | +++ | +++ | +++ | +++ |
| B-48 | +++ | >32 | +++ | +++ | ++ | +++ | +++ | +++ | +++ |
| B-49 | +++ | >32 | +++ | +++ | +++ | +++ | +++ | +++ | +++ |
| B-50 | +++ | +++ | +++ | ND | +++ | +++ | ND | +++ | ND |
| B-51 | + | >32 | +++ | ND | ++ | + | ND | + | ND |
| B-52 | >32 | >32 | >32 | ND | ND | ND | ND | >32 | ND |
| B-53 | +++ | >32 | +++ | +++ | +++ | +++ | +++ | +++ | +++ |
| B-54 | ++ | >32 | ++ | ND | +++ | ++ | ND | +++ | ND |
| B-55 | +++ | >32 | +++ | ND | ND | ND | ND | +++ | ND |
| B-56 | +++ | >32 | +++ | ND | +++ | +++ | ND | +++ | ND |
| B-57 | + | >32 | +++ | ND | ND | ND | ND | +++ | ND |
| B-58 | +++ | >32 | +++ | + | +++ | +++ | ++ | +++ | +++ |
| B-59 | + | >32 | ++ | ND | ND | ND | ND | ++ | ND |
| B-60 | + | >32 | + | ND | ND | ND | ND | + | ND |
| B-61 | ND | >32 | >32 | ND | >32 | ND | ND | ND | ND |
| B-62 | + | >32 | ++ | ND | +++ | +++ | ND | ++ | ND |
| B-63 | + | >32 | >32 | ND | +++ | +++ | ND | +++ | ND |
| B-64 | +++ | +++ | +++ | ND | +++ | +++ | ND | +++ | ND |
| B-65 | ++ | >32 | + | ND | + | ++ | ND | ++ | ND |
| B-66 | + | >32 | >32 | ND | >32 | >32 | ND | >32 | ND |
| B-67 | +++ | >32 | +++ | ND | ND | ND | ND | +++ | ND |
| B-68 | +++ | >32 | +++ | ND | +++ | +++ | ND | +++ | ND |
| B-69 | + | >32 | + | ND | + | >32 | ND | +++ | ND |
| B-70 | + | >32 | ++ | ND | ND | ND | ND | + | ND |
| B-71 | + | >32 | ++ | ND | ND | ND | ND | +++ | ND |
| B-73 | +++ | >32 | >32 | ND | ++ | ++ | ND | ND | ND |
| B-79 | >32 | >32 | >32 | ND | >32 | >32 | ND | ND | ND |
| B-80 | +++ | >32 | +++ | ND | +++ | +++ | ND | ND | ND |
| B-81 | >32 | >32 | >32 | ND | >32 | >32 | ND | ND | ND |
| B-82 | +++ | >32 | +++ | ND | +++ | +++ | ND | +++ | ND |
| B-83 | +++ | >32 | +++ | ND | +++ | +++ | ND | +++ | ND |
| B-84 | +++ | + | +++ | ND | +++ | +++ | ND | +++ | ND |
| B-85 | +++ | + | +++ | ND | +++ | +++ | ND | +++ | ND |
| B-86 | +++ | >32 | +++ | ND | +++ | +++ | ND | +++ | ND |
| C-1 | + | >32 | ++ | ND | ++ | + | ND | +++ | ND |
| C-2 | ++ | >32 | ++ | ND | ++ | ++ | ND | +++ | ND |
| C-3 | + | >32 | ++ | ND | + | + | ND | +++ | ND |
| C-4 | + | >32 | + | ND | + | + | ND | +++ | ND |
| C-5 | + | >32 | + | ND | + | + | ND | +++ | ND |
| C-6 | + | >32 | + | ND | + | + | ND | +++ | ND |
| C-7 | + | >32 | + | ND | ++ | + | ND | +++ | ND |
| C-8 | +++ | +++ | +++ | ND | +++ | +++ | ND | +++ | ND |
| C-9 | +++ | +++ | +++ | +++ | +++ | +++ | +++ | +++ | +++ |

TABLE E-continued

In Vitro Biological Activity

| Cpd. Ref. | Organism (Minimum Inhibitory Concentration (MIC), µg/mL) | | | | | | | | |
|---|---|---|---|---|---|---|---|---|---|
| | A | B | C | D | E | F | G | H | I |
| C-10 | +++ | + | +++ | ND | +++ | +++ | ND | +++ | ND |
| C-11 | +++ | >32 | ++ | ND | ++ | +++ | ND | +++ | ND |
| C-12 | +++ | >32 | +++ | ND | +++ | +++ | ND | +++ | ND |
| C-13 | +++ | >32 | +++ | ND | +++ | +++ | ND | +++ | ND |
| C-14 | +++ | >32 | ++ | ND | +++ | +++ | ND | +++ | ND |
| C-15 | ++ | >32 | + | ND | ++ | +++ | ND | +++ | ND |
| C-16 | +++ | >32 | +++ | ND | +++ | +++ | ND | +++ | ND |
| C-17 | +++ | >32 | +++ | ND | +++ | +++ | ND | +++ | ND |
| C-18 | +++ | >32 | +++ | ND | +++ | +++ | ND | +++ | ND |
| C-19 | +++ | >32 | +++ | ND | +++ | +++ | ND | +++ | ND |
| C-20 | >32 | >32 | >32 | ND | >32 | >32 | ND | +++ | ND |
| C-21 | ++ | >32 | ++ | ND | ++ | +++ | ND | +++ | ND |
| C-22 | +++ | + | +++ | ND | +++ | +++ | ND | +++ | ND |
| C-23 | +++ | >32 | ++ | ND | +++ | +++ | ND | +++ | ND |
| C-24 | ++ | >32 | ++ | ND | ++ | +++ | ND | +++ | ND |
| C-25 | >32 | >32 | >32 | ND | >32 | >32 | ND | +++ | ND |
| D-1 | +++ | >32 | +++ | ND | +++ | +++ | ND | +++ | ND |
| D-2 | +++ | + | +++ | +++ | + | +++ | +++ | +++ | +++ |
| D-3 | +++ | +++ | +++ | + | +++ | +++ | +++ | +++ | +++ |
| D-4 | >32 | >32 | >32 | ND | >32 | >32 | ND | >32 | +++ |
| D-5 | +++ | >32 | +++ | ND | +++ | +++ | ND | +++ | ND |
| D-6 | + | >32 | + | ND | >32 | + | ND | +++ | ND |
| D-7 | +++ | + | +++ | ND | +++ | +++ | ND | +++ | ND |
| D-8 | +++ | >32 | +++ | +++ | +++ | +++ | +++ | +++ | +++ |
| D-9 | +++ | >32 | +++ | +++ | +++ | +++ | +++ | +++ | +++ |
| D-10 | +++ | ++ | +++ | +++ | +++ | + | +++ | +++ | +++ |
| D-11 | +++ | +++ | +++ | +++ | +++ | +++ | +++ | +++ | +++ |
| D-12 | +++ | +++ | +++ | ++ | +++ | +++ | +++ | +++ | +++ |
| D-13 | +++ | + | +++ | ++ | +++ | +++ | +++ | +++ | +++ |
| D-14 | +++ | >32 | +++ | ND | +++ | +++ | ND | +++ | ND |
| D-15 | +++ | +++ | +++ | ND | +++ | +++ | ND | +++ | ND |
| D-16 | +++ | +++ | +++ | ND | +++ | +++ | ND | +++ | ND |
| D-17 | +++ | +++ | +++ | ND | +++ | +++ | ND | +++ | ND |
| D-18 | +++ | + | +++ | ND | +++ | +++ | ND | +++ | ND |
| D-19 | +++ | ++ | +++ | ND | +++ | +++ | ND | +++ | ND |
| D-20 | +++ | ++ | +++ | ND | +++ | +++ | ND | +++ | ND |
| D-21 | ++ | ++ | +++ | ND | +++ | +++ | ND | +++ | ND |
| D-22 | +++ | ++ | +++ | ND | +++ | +++ | ND | +++ | ND |
| D-23 | +++ | ++ | +++ | ND | +++ | +++ | ND | +++ | ND |
| D-24 | +++ | +++ | +++ | ND | +++ | +++ | ND | +++ | ND |
| D-25 | +++ | + | +++ | ND | +++ | +++ | ND | +++ | ND |
| D-26 | +++ | + | +++ | ND | +++ | +++ | ND | +++ | ND |
| D-27 | ++ | >32 | +++ | ND | + | + | ND | +++ | ND |
| D-28 | + | >32 | + | ND | + | + | ND | +++ | ND |
| D-29 | ++ | >32 | ++ | ND | + | + | ND | +++ | ND |
| E-1 | + | >32 | + | ND | ++ | ++ | ND | +++ | ND |
| E-2 | +++ | >32 | +++ | +++ | +++ | +++ | +++ | +++ | +++ |
| E-3 | + | >32 | + | ND | >32 | + | ND | + | ND |
| E-4 | >32 | >32 | >32 | ND | + | + | ND | ++ | ND |
| E-5 | >32 | >32 | >32 | ND | + | + | ND | >32 | ND |
| E-6 | + | >32 | >32 | ND | ++ | ++ | ND | ++ | ND |
| E-7 | +++ | >32 | +++ | +++ | +++ | +++ | +++ | +++ | +++ |
| E-8 | + | >32 | +++ | ND | +++ | +++ | ND | +++ | ND |
| E-9 | >32 | >32 | + | ND | >32 | >32 | ND | + | ND |
| E-10 | +++ | >32 | +++ | ND | +++ | +++ | ND | +++ | ND |
| E-11 | +++ | >32 | +++ | ND | +++ | +++ | ND | +++ | ND |
| E-12 | ++ | >32 | ++ | ND | ++ | ++ | ND | +++ | ND |
| E-13 | >32 | + | >32 | ND | + | ++ | ND | +++ | ND |
| E-14 | +++ | ++ | +++ | ND | +++ | +++ | ND | +++ | ND |
| E-15 | ++ | ++ | ++ | ND | +++ | +++ | ND | +++ | ND |
| E-16 | +++ | +++ | >32 | ND | +++ | +++ | ND | +++ | ND |
| E-17 | +++ | >32 | >32 | ND | +++ | +++ | ND | +++ | ND |
| E-18 | +++ | >32 | +++ | ND | +++ | +++ | ND | +++ | ND |
| E-19 | +++ | >32 | +++ | ND | +++ | +++ | ND | +++ | ND |
| F-1 | +++ | >32 | +++ | ND | +++ | +++ | ND | +++ | ND |
| F-2 | + | ND | + | ND | + | >32 | ND | >32 | ND |
| F-3 | + | >32 | ++ | ND | + | + | ND | +++ | ND |
| F-5 | >32 | >32 | >32 | ND | >32 | >32 | ND | +++ | >32 |
| F-6 | >32 | >32 | + | ND | >32 | >32 | ND | +++ | ND |
| F-7 | >32 | >32 | + | ND | + | + | ND | +++ | ND |
| F-8 | ++ | + | + | ND | ++ | ++ | ND | +++ | ND |
| F-9 | >32 | >32 | >32 | ND | + | + | ND | + | ND |
| F-10 | ++ | + | ++ | ND | ++ | ++ | ND | + | ND |
| G-1 | +++ | +++ | +++ | ND | +++ | +++ | ND | +++ | ND |
| G-2 | +++ | +++ | +++ | ND | +++ | +++ | ND | +++ | ND |
| G-3 | ++ | + | + | ND | + | ++ | ND | ++ | ND |

Key to organisms tested against:
A = *B. cereus* ATCC 11778
B = *C. albicans* ATCC 38247
C = *E. faecalis* ATCC 29212
D = *E. faecium* ATCC 51559
E = *S. aureus* ATCC 13709
F = *S. aureus* ATCC 27660
G = *S. epidermidis* ATCC 12228
H = *S. pneumoniae* ATCC 49619
I = *S. pneumoniae* ATCC 51422
Key to activity:
+++ = MIC ≤ 4
++ = 4 < MIC < 12
+ = 12 ≤ MIC ≤ 32
ND = not determined
>32 = preliminary data indicates MIC greater than 32

In Vivo Biological Data

This example demonstrates in vivo efficacy against infection by methicillin resistant *Staphylococcus aureus* ATCC 33591, using a murine neutropenic thigh model.

A *S. aureus* ATCC 33591 culture was grown to log phase overnight and diluted in phosphate buffered saline (pH 7.2) to an optical density of about 0.1 at 600 nm, giving an approximate concentration of $10^8$ cfu/mL. The suspension was diluted 1:100 in phosphate buffered saline (pH 7.2) for a final concentration of $10^6$ cfu/mL.

Outbred female CF1 mice (approx. 20 gram body weight) were rendered neutropenic by treatment with cyclophosphamide (200 mg/kg body weight, intraperitoneal injection) at 2 and 4 days prior to inoculation. Groups of 5 mice were inoculated with 0.05 mL of the bacteria (approx. $10^6$ cfu/mL) into the anterior thigh. Each group was treated intravenously two hours post infection with vehicle (phosphate buffered saline) or test compound. The mice were sacrificed at either 6 or 24 hrs after treatment and thighs were collected aseptically. Each thigh was weighed, placed into sterile saline, and homogenized. The tissue homogenates were diluted appropriately for plating on agar plates. Colony counts were recorded (cfu/gram) and compared to control groups. The data are presented in Table F below:

TABLE F

Murine Neutropenic Thigh Model

| Compound No. (Time) | Dose (mg/kg) | Colony Count (log cfu/gram) | |
|---|---|---|---|
| | | Compound | Vehicle |
| A-4 (6 hr) | 50 | 4.99 | 8.02 |
| A-4 (6 hr) | 25 | 5.75 | 7.99 |
| A-6 (6 hr) | 50 | 6.65 | 8.02 |
| A-8 (6 hr) | 50 | 4.45 | 8.12 |
| A-8 (6 hr) | 25 | 5.85 | 8.12 |
| A-9 (6 hr) | 50 | 5.11 | 8.02 |
| A-9 (6 hr) | 25 | 7.11 | 8.67 |
| A-26 (6 hr) | 50 | 5.34 | 7.74 |
| A-26 (6 hr) | 25 | 6.37 | 8.04 |
| B-6 (6 hr) | 50 | 6.37 | 8.17 |
| B-47 (6 hr) | 50 | 7.53 | 8.54 |
| B-50 (6 hr) | 50 | 6.58 | 8.76 |

TABLE F-continued

Murine Neutropenic Thigh Model

| Compound No. | Dose | Colony Count (log cfu/gram) | |
|---|---|---|---|
| (Time) | (mg/kg) | Compound | Vehicle |
| B-56 (6 hr) | 50 | 6.38 | 7.65 |
| B-67 (6 hr) | 50 | 7.73 | 8.76 |
| C-12 (6 hr) | 50 | 5.93 | 7.88 |
| D-3 (6 hr) | 50 | 6.28 | 7.99 |
| D-11 (6 hr) | 50 | 6.25 | 7.99 |
| E-15 (6 hr) | 50 | 5.77 | 7.95 |

In vivo efficacy was shown by a decrease in colony count (log cfu/gram of tissue) in the compound-treated animals when compared against the colony count in animals given only the vehicle.

DNA Binding

This example illustrates the DNA binding properties of compounds of this invention using a DNase I footprinting technique. Generally, the procedure described in Dervan, WO 98/50582 (1998), was followed.

Double stranded circular plasmids A and B were used to prepare double stranded DNA-binding probes containing the target sequences for the DNase I footprint titration experiments.

Plasmid A was prepared by hybridizing two sets of 5'-phosphorylated complementary oligonucleotides, the first set being
5'-CTAGATGCCGCTAAGTACTATGC-
CGCTAACTACTATGCCGCTAATTACTATGCCGC-3'
and
5'-CATAGTAATTAGCGGCATAGTAGT-
TAGCGGCATAGTACTTAGCGGCAT-3';

and the second set being
5'-TAAATACTATGCCGCTAACTAGTATGC-
CGCTATGCA-3',
and
5'-TAGCGGCATACTAGTTAGCGGCATAG-
TATTTAGCGG-3', and ligating the resulting duplexes to the large pUC19 XbaI/PstI restriction fragment.

Plasmid B was the plasmid pTrc99a, obtained from Amersham Pharmacia Biotech, Inc.

The 3'-$^{32}$P end-labeled EcoRI/PvuII fragments from each plasmid were prepared by digesting the plasmids with EcoRI and PvuII with simultaneous fill-in using Sequenase v. 2.0, [$\alpha$-$^{32}$P]-deoxyadenosine-5'-triphosphate, and [$\alpha$-$^{32}$P]-thymidine-5'-triphosphate, and isolating the cloned fragments by nondenaturing gel electrophoresis. A and G sequencing reactions were carried out as described (See Maxam and Gilbert, *Methods Enzymol.*, 1980, 65, 499-560; Iverson and Dervan, *Methods Enzymol.*, 1987, 15, 7823-7830; Sambrook et al., 1989, *Molecular Cloning*, 2$^{nd}$ ed., Cold Spring Harbor Laboratory Press: Cold Spring Harbor, N.Y.) Standard methods were used for all DNA manipulations (Sambrook et al., ibid.)

The 310 base pair dsDNA restriction fragment (SEQ ID NO. I) of Plasmid A contained a target sequence AGTACT. The 352 base pair dsDNA restriction fragment (SEQ ID NO. II) of Plasmid B contained target sequences ACAATTAT and AATTAATCAT. These fragments were used for quantitative DNase I footprinting experiments. The target sequences were selected for their identity with, or similarity to, promoter sites for bacterial genes.

Quantitative DNase I footprint titration experiments were carried out as described previously (Dervan, WO 98/50582, 1998) with the following changes. All reactions were carried out in a total volume of 400 µL, with compound stock solution or water added to 15,000 cpm radiolabeled restriction fragment affording final solution conditions of 10 mM TrisHCl, 10 mM KCl, 10 mM MgCl$_2$, 5 mM CaCl$_2$, pH 7.0 and 0.01 nM, 0.1 nM, 1.0 nM, 10.0 nM compound or no compound for reference lanes. The compounds were allowed to equilibrate at 22° C. for 16 hr. Footprinting reactions were initiated with addition of 10 µL of a DNase I stock solution (at the appropriate concentration to give ~50% intact DNA) containing 1 mM DTT and allowed to proceed for 7 min at 22° C. The reactions were stopped, ethanol precipitated, resuspended in loading buffer, heat denatured, and placed on ice as described previously (Dervan WO 98/50582, 1998). The reaction products were separated on a precast 8% polyacrylamide denaturing sequencing Castaway gel with 32 preformed wells from Stratagene in 1X TBE at 2000 V. Gels were dried according to the manufacturer and exposed to a storage phosphor screen (Molecular Dynamics). Quantitation and data analysis were carried out as described in Dervan, WO 98/50582, 1998.

dsDNA binding results are provided in Table G:

TABLE G dsDNA Binding

| Compound | Target Sequence | Dissociation Constant K$_d$ (nM) | Target Location (Fragment/Plasmid). |
|---|---|---|---|
| A-3 | AATACT | 5 | 310 bp/A |
| A-3 | AATTAATCAT | 1 | 352 bp/B |
| B-18 | AGTACT | 50 | 310 bp/A |
| B-18 | AATTAATCAT | 2 | 352 bp/B |

SEQUENCE LISTINGS (310 bp EdoRI/PvuII restriction fragment from
Plasmid A; only one strand shown)
                                       SEQ ID NO. I
AATTCGAGCTCGGTACCCGGGGATCCTCTAGATGCCGCTAAGTACTATGC

CGCTAACTACTATGCCGCTAATTACTATGCCGCTAAATACTATGCCGCTA

ACTAGTATGCCGCTATGCAGGCATGCAAGCTTGGCGTAATCATGGTCATA

GCTGTTTCCTGTGTGAAATTGTTATCCGCTCACAATTCCACACAACATAC

GAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCT

GTCGTGCCAG (352 bp EdoRI/PvuII restriction fragment from
Plasmid B; only one strand shown)
                                      SEQ ID NO. II
CTGGCACGACAGGTTTCCCGACTGGAAAGCGGGCAGTGAGCGCAACGCAA

TTAATGTGAGTTAGCGCGAATTGATCTGGTTTGACAGCTTATCATCGACT

GCACGGTGCACCAATGCTTCTGGCGTCAGGCAGCCATCGGAAGCTGTGGT

```
-continued

ATGGCTGTGCAGGTCGTAAATCACTGCATAATTCGTGTCGCTCAAGGCGC

ACTCCCGTTCTGGATAATGTTTTTTGCGCCGACATCATAACGGTTCTGGC

AAATATTCTGAAATGAGCTGTTGACAATTAATCATCCGGCTCGTATAATG

TGTGGAATTGTGAGCGGATAACAATTTCACACAGGAAACAGACCATGGA

ATT
```

Synthesis of Compounds

General

Typically, compound structures were confirmed by $^1$H-NMR and/or mass spectrometry. Where a parenthetical remark such as "$^1$H-NMR" or "mass spectrum" follows without elaboration a reference to a compound, it means that such spectrum was taken, was consistent with the assigned structure, and did not indicate the presence of significant impurities.

Abbreviations or acronyms in common usage are employed for various solvents, catalysts and reagents, including: TFA for trifluoroacetic acid, NMP for N-methylpyrrolidone, DMF for N,N-dimethylformamide, MsCl for methanesulfonyl chloride, triflate for trifluoromethanesulfonate, HBTU for 2-(1H-benzotriazole-1-yl)-1,1,3,3-tetramethyluronium hexafluorophosphate; DIEA for diisopropylethylamine; HOBt for hydroxybenzotriazole; DCC for dicyclohexylcarbodiimide; BOPCl for bis(2-oxo-3-oxazolidinyl)-phosphinic chloride; HATU for O-(7-azabenzotriazol-1-yl)-N,N,N',N'-tetramethyluronium hexafluorophosphate; Boc$_2$O for Boc anhydride; and MOMCl for methoxymethyl chloride.

The skilled artisan will understand that: (a) an intermediate or synthetic route described in the context of the synthesis of a particular compound of this invention can also be used to make other compounds of this invention, mutatis mutandis; (b) in certain experimental sections only the preparation of an intermediate compound is described, because its incorporation into a compound of this invention straightforwardly follows synthetic methodology described elsewhere herein; and (c) for some routine reactions that recur herein, a detailed description of each set of reaction and work-up conditions may be replaced by a reference to a general procedure in the interest of brevity, the conditions described in the general procedure being adaptable to the instance at hand without undue experimentation.

General Procedures

Procedure A: activation of a heterocyclic carboxylic acid with HBTU (or HATU) and coupling to a heterocyclic amine.

The acid (1.2 equiv.) and HBTU (or HATU, for less reactive amines) (1.14 equiv.) were dissolved in NMP (or DMF, dilution: ca. 1 g/10 mL) and DIEA (ca. 1/10 of the volume of NMP/DMF), stirred for 30-60 min at 25-40° C. and added to a solution of the amine (1 equiv.) in NMP (or DMF, dilution: ca. 1 g/5 mL) and DIEA (ca. 1/10 of the volume of NMP/DMF). The mixture was stirred for 12 to 16 h at 25-40° C.

Procedure B: activation of a heterocyclic carboxylic acid with HBTU and coupling to an aliphatic amine.

A heterocyclic acid (1 equiv.) and HBTU (1.1 to 1.2 equiv.) were dissolved in NMP (or DMF, dilution: ca. 1 g/10 mL) and DIEA (ca. 1/10 of the volume of NMP/DMF), stirred for 30-60 min at 25-40° C. and treated with the aliphatic amine (excess, ca. 2 to 50 equiv.). The mixture was stirred for 12 to 16 h at 2540° C.

Procedure C: activation of a heterocyclic carboxylic acid with BOPCl and coupling to an aliphatic amine.

A heterocyclic acid (1 equiv.) and BOPCl (1.2 equiv.) were dissolved in NMP (or DMF, dilution: ca. 1 g/10 mL) and DIEA (ca. 1/10 of the volume of NMP/DMF), stirred for 30-60 min at 25-40° C. and treated with the aliphatic amine (excess, ca. 2 to 50 equiv.). The mixture was stirred for 12 to 16 h at 25-40° C.

Procedure D: coupling of a heterocyclic acyl chloride to a heterocyclic amine.

A mixture of the heterocyclic acid chloride (1.0 to 1.2 equiv.) and the heterocyclic amine in NMP (or DMF, dilution: ca. 1 g/10 mL) and DIEA (ca. 1/10 of the volume of NMP/DMF) was stirred at 25-60° C. for 12 to 16 h.

Procedure E: workup and purification by HPLC.

The crude product was diluted with an approximately 3× volume of a mixture of AcOH/H$_2$O (1:1) and purified by preparative HPLC. The product was characterized by $^1$H-NMR (d$_6$-DMSO) and ESI-MS.

Procedure F: workup and purification by HPLC.

The crude product was diluted with an approximately 7× volume of a mixture of AcOH/H$_2$O (1:1) and washed with Et$_2$O (1 to 3 times). The aqueous layer was purified by preparative HPLC. The product was characterized by $^1$H-NMR (d$_6$-DMSO) and ESI-MS.

Procedure G: precipitation and filtration.

The reaction mixture was added dropwise to ice-water (ca. 10 to 15 times the volume of the reaction mixture). The resulting precipitate was collected by filtration and dried to give the crude product as a solid.

Procedure H: saponification of a heterolcclic carboxylic acid ester.

A mixture of the ester and NaOH or KOH (ca. 0.5 g base per g ester) in H$_2$O (ca. 1 g ester per 40 mL) and MeOH or EtOH (1 g ester per 20 mL) was stirred at 40-70° C. for 3 to 12 h. The reaction mixture was diluted with H$_2$O (ca. twice the volume of the reaction mixture), washed with AcOEt (1×) and acidified to pH=2-3 using ca. 6M aqueous HCl. The resulting precipitate was collected by filtration and dried.

Procedure I: hydrogenation of an aryl nitro group to an aryl: amine and isolation of the amine as the hydrochloride.

A suspension of the nitro compound and 10% Pd-C (5-10 wt % with respect to the nitro compound) in a mixture of MeOH/AcOEt (ca. 1:10 to 1:1) was stirred at room temperature (RT) under H$_2$ atmosphere (1 atm to 150 psi) for 10-20 hr and filtered through Celite. The filtrate was concentrated in vacuo, diluted with Et$_2$O, and treated with HCl (g). The resulting precipitate was collected by filtration and dried, or in case no precipitate was formed, the crude reaction mixture was evaporated to dryness.

EXAMPLE A

This example relates to the synthesis of compounds according to formula (Ic), such as compounds A-3 to A-16, A-24, A-26, A-29 (Scheme 1) and A-17 to A-23, A-25 (Scheme 2). Schemes 1 and 2 illustrate the synthesis of compounds A-3 and A-17, respectively.

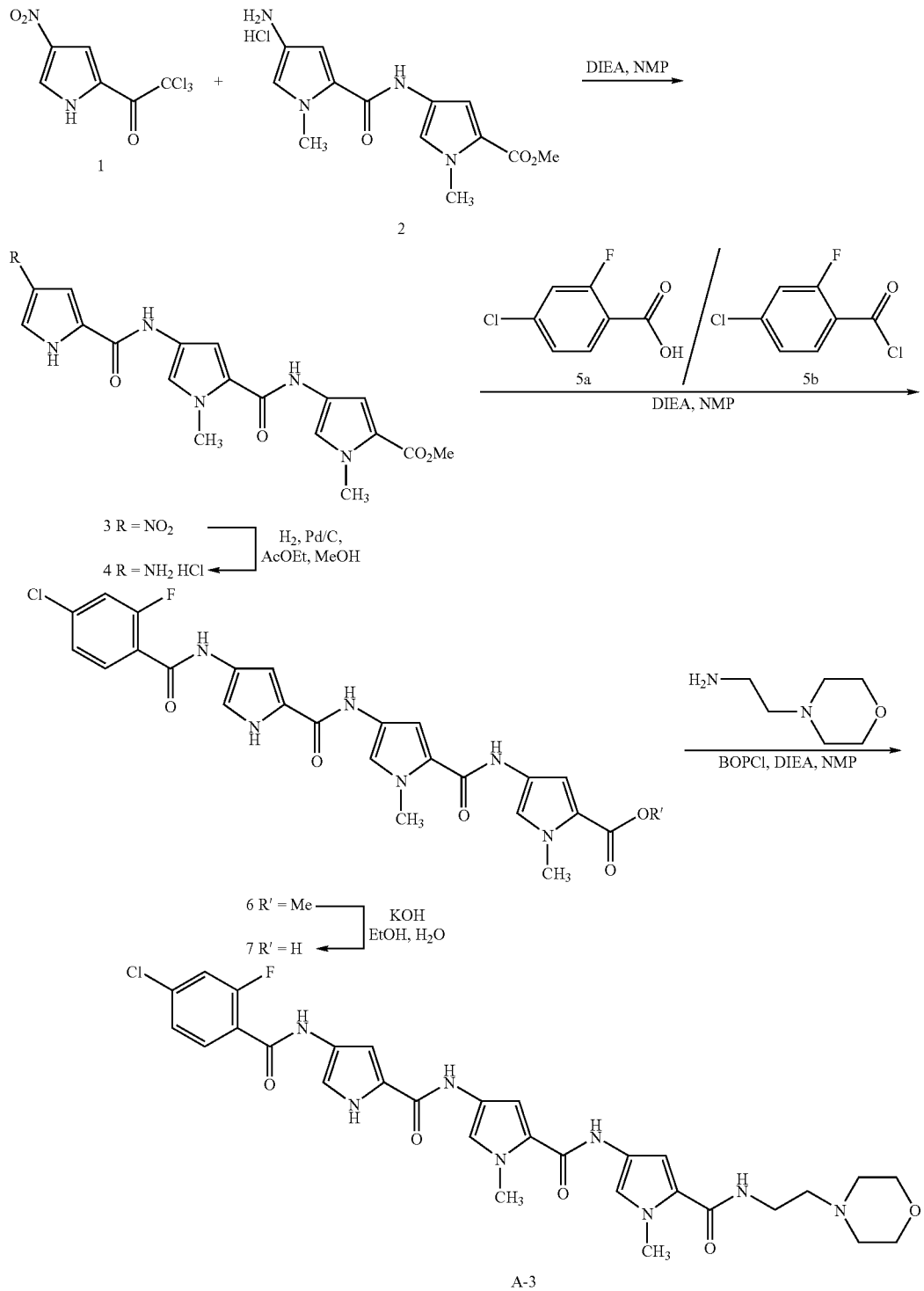
Scheme 1
Trimer 3
A solution of ketone 1 (60.0 g, 1.0 equiv.) and amine 2 (72.7 g, 1.0 equiv.) in NMP (500 mL) and DIEA (95 mL) was stirred for 2 h at RT (slight exotherm). The reaction mixture was added dropwise to ice-water (1.5 L), the resulting precipitate collected by filtration and dried to give trimer 3 (89 g, 92%, dark powder).
Amine 4
Trimer 3 (11.0 g, 1 equiv.) was hydrogenated using Procedure I to give amine 4 (8.75 g, 78%).

Tetramer 6

Carboxylic acid 5a (1.45 g, 1.2 equiv.) and amine 4 (2.9 g, 1. equiv.) were coupled using Procedure A to give tetramer 6 as a dark powder (2.77 g, 74%, ¹H-NMR). (4-Chloro-2-fluoro-benzoyl chloride (5b) can be used instead of acid (5a)/HBTU.)

Acid 7

Tetramer 6 (2.77 g, 1 equiv.) was saponified using Procedure H to give acid 7 (2.06 g, 76%).

Compound A-3

Acid 7 (0.62 g, 1 equiv.) and 4-(2-aminoethyl)-morpholine (5 mL) were coupled according to Procedure B using HBTU (490 mg, 1.1 equiv.). Purification according to Procedure F gave compound A-3 (290 mg).

EXAMPLE B

Scheme 2 describes the preparation of additional compounds (Ic), where the subscript i is 2. Intermediates 9 to 12 were prepared similarly to intermediates 3, 4, 6 and 7, respectively (Scheme 1). Similarly to the synthesis of compound A-3, compounds such as A-17 to A-23 and A-25 were prepared using Procedures B and F or Procedures C and E.

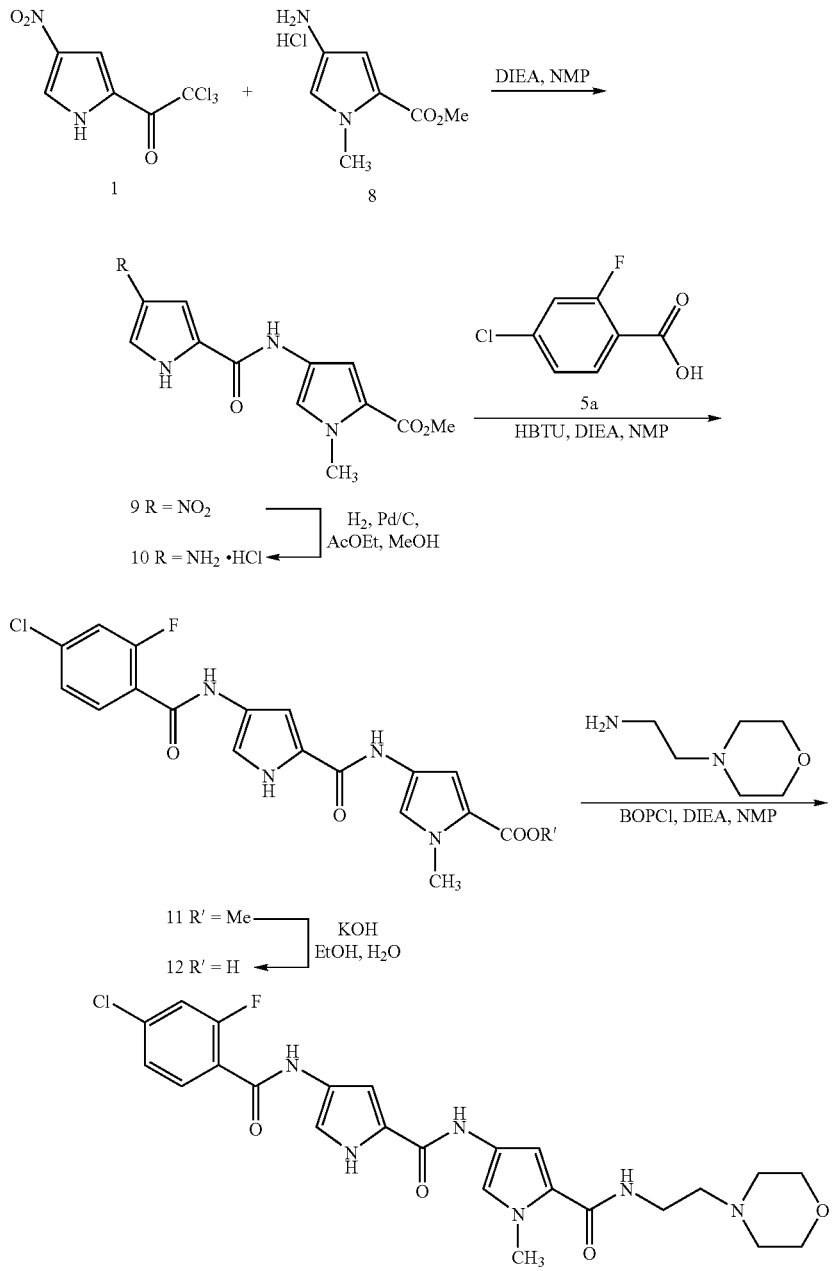

EXAMPLE C

Scheme 3 illustrates an alternative synthesis of compounds (Ic). The final step is the coupling of trimeric amine 15 with various benzoic acids (e.g., 16 to 19) according to the Procedures A and F to yield the final products A-1, A-30, A-34 and A-35, respectively.

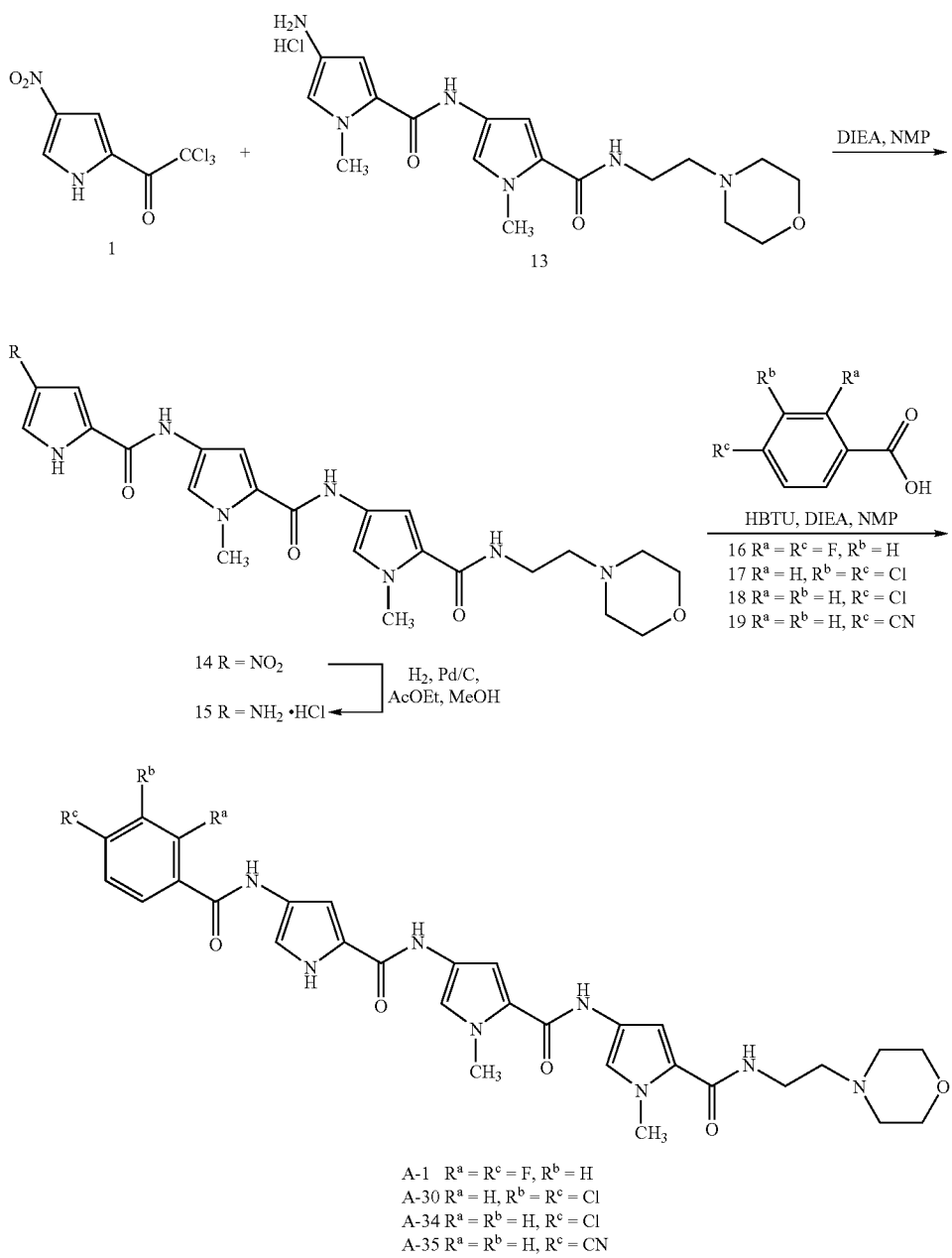

EXAMPLE D

The synthesis of compounds bearing a quaternized methyl morpholinium moiety at the C-terminus is illustrated in Scheme 4 with specific reference to compound A-28. Compound B-30 was prepared analogously.

Scheme 4

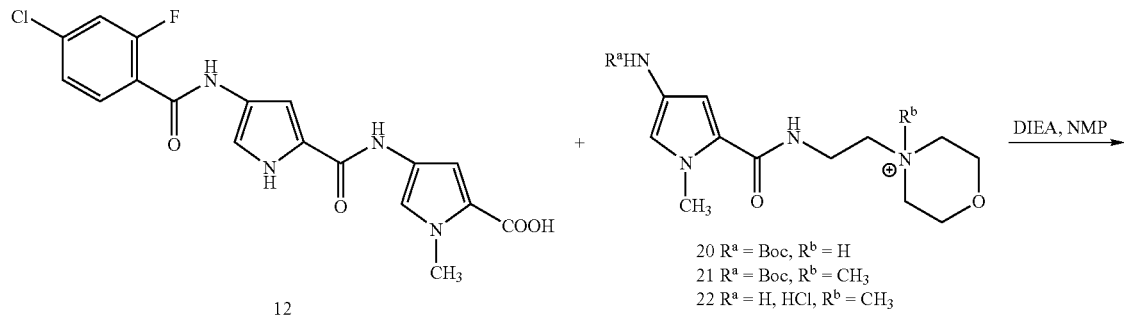

20 $R^a$ = Boc, $R^b$ = H
21 $R^a$ = Boc, $R^b$ = $CH_3$
22 $R^a$ = H, HCl, $R^b$ = $CH_3$

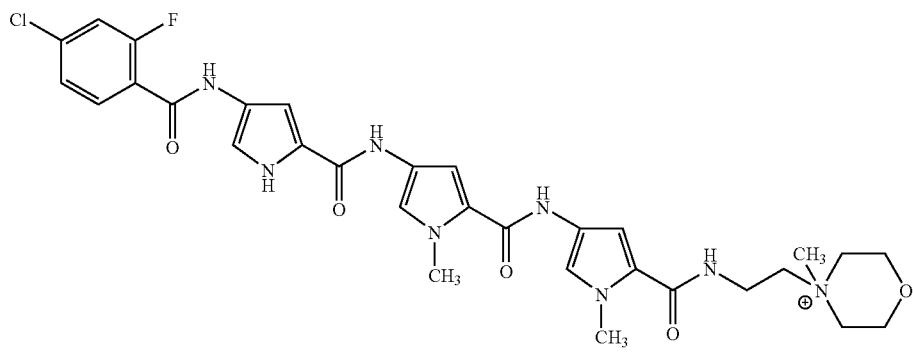

A-28

Compound 21

A solution of morpholino compound 20(1.00 g, 1.0 equiv.) in $CH_2Cl_2$ (10 mL) was treated at RT with methyl triflate (0.337 mL, 1.05 equiv.) and stirred for 2 h. The mixture was treated with DIEA (0.5 mL) and additional methyl triflate (0.3 mL). Stirring was continued for 1½h and the solvent was evaporated. The $^1$H-NMR spectrum of the crude product was in agreement with the structure of compound 21, but showed minor impurities. The material was used without further purification.

Compound 22

A solution of crude compound 21 in MeOH (ca. 40 mL) was saturated with HCl (g) for about 20 seconds and stirred at RT for 1 h. Evaporation of the solvent gave compound 22 ($^1$H-NMR, mass spectrum).

Compound A-28

Trimeric acid 12 (79.9 mg, 1.2 equiv.) and compound 22(60 mg, 1.0 equiv.) were coupled according to Procedure A using HBTU (76.3 mg, 1.14 equiv.) and purified according to Procedure F to give compound A-28.

EXAMPLE E

Scheme 5 shows an efficient synthetic approach for compounds (Id), with specific reference to compound B-11. The scheme is applicable to other compounds such as B-3 to B-22, B-24 to B-29, B-31 to B-34 to B-38 to B-50, B-52 to B-62, B-65, and B-67 to B-71.

Scheme 5

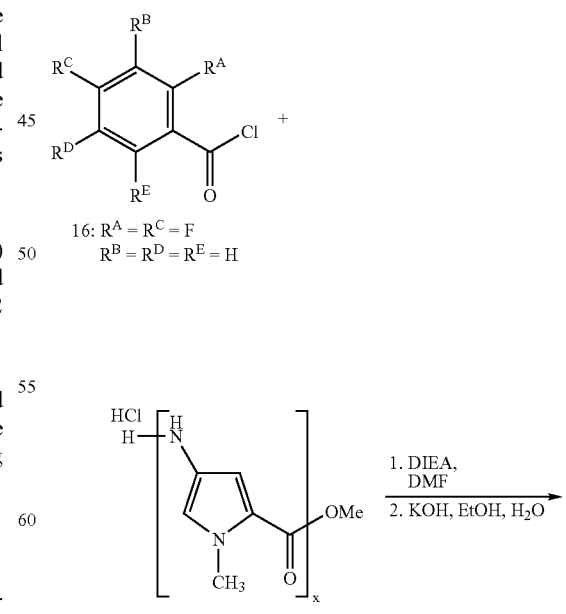

16: $R^A$ = $R^C$ = F
$R^B$ = $R^D$ = $R^E$ = H x = 1 to 4
2: x = 2
30: x = 3

EXAMPLE F

Compounds bearing a guanidinium group at the C-terminus were prepared from the corresponding primary amine according to Scheme 6 (exemplified with compound B-23).

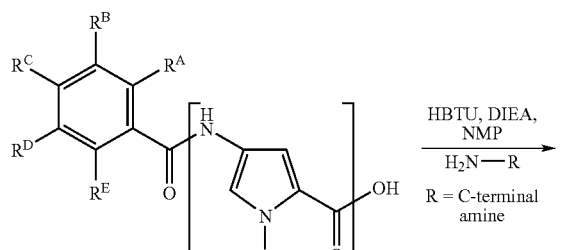

x = 1 to 4

32: x = 2; $R^A = R^C = F$
$R^B = R^D = R^E = H$
31: corresponding Me ester

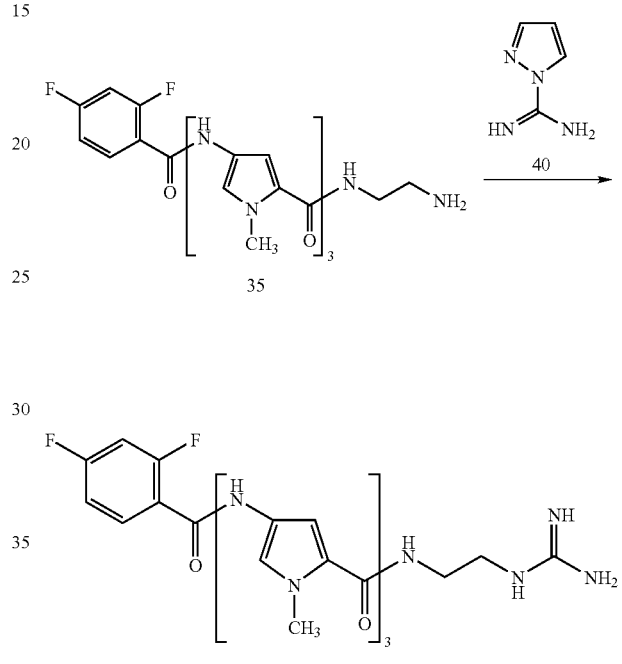

Scheme 6

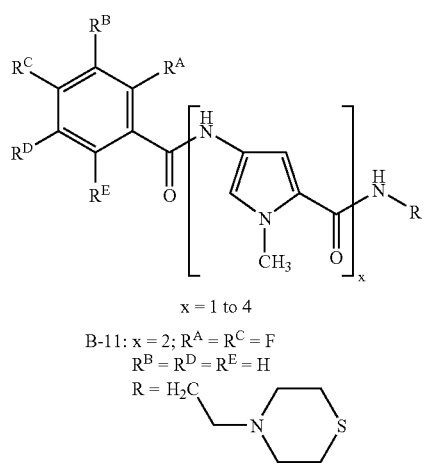

x = 1 to 4

B-11: x = 2; $R^A = R^C = F$
$R^B = R^D = R^E = H$
R = $H_2C$—[thiomorpholine]

Ester 31

2,4-Difluorobenzoyl chloride(2.16mL, 1.1 equiv.)and amino ester 2 (5.00 g, 1.0 equiv.) were coupled according to Procedure D. Workup according to Procedure G gave ester 31 as a white solid (4.94 g, 74%, $^1$H-NMR).

Acid 32

Ester 31 (4.94 g, 1.0 equiv.) was saponified according to Procedure H to give acid 32 (4.44 g, 92%, $^1$H-NMR) as a white solid.

Compound B-11

Acid 32 (100 mg, 1.05 equiv.) and 4(2-aminoethyl)-thiomorpholine (300 µl) were coupled according to Procedure B using HBTU (90 mg, 1.0 equiv.). Purification according to Procedure F gave compound B-11.

Compound B-23

A solution ofthe primary amine 35 (10 mg, ca. 1 equiv.) and pyrazole 40 (ca. 4.5 mg, ca. 6 equiv.) in DMF (0.3 mL) and DIEA (0.03 mL) was stirred at RT for 12 h. Workup according to Procedure E yielded compound B-23.

EXAMPLE G

Scheme 8 describes another synthetic approach to compounds according to formula (Id) (i=3). Either an in situ activated benzoic ester (OBt ester) or an acid chloride can be used as a coupling partner for amine 54. Compounds B-72 to B-80 were analogously synthesized.

Scheme 8

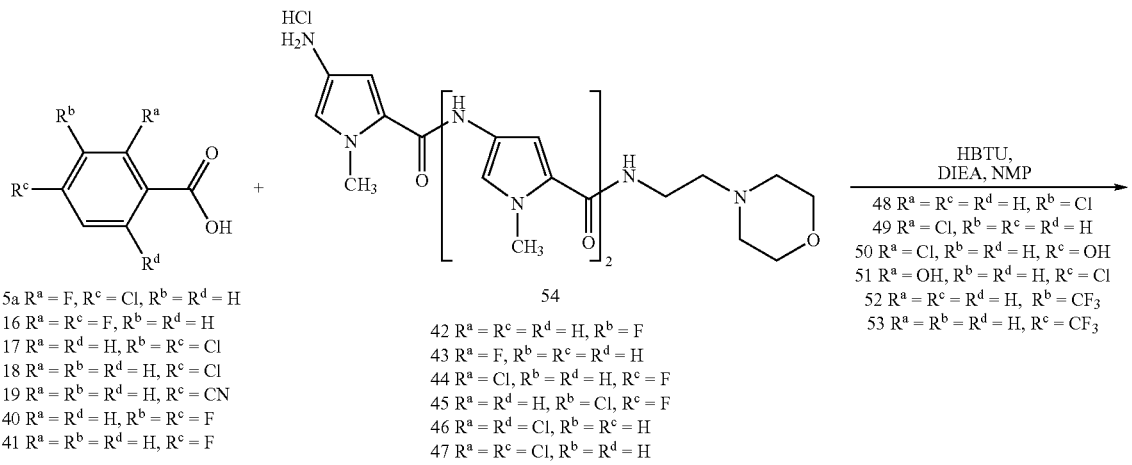

Compound B-47

Benzoic acid 5 (46 mg, 1.2 equiv.) and amine 54 (110 mg, 1.0 equiv.) were coupled according to Procedure A using HBTU (96 mg, 1.14 equiv.). Purification according to Procedure F gave compound B-47.

EXAMPLE H

Scheme 9 illustrates the synthesis of compounds (Id) (i=2), using an approach analogous to that of Scheme 8: either a benzoic acid (e.g. 5a) was coupled to the amine 13 according to Procedure A and worked up according to Procedure F or a benzoyl chloride was coupled to 13 according to Procedure D and worked up according to Procedure E.

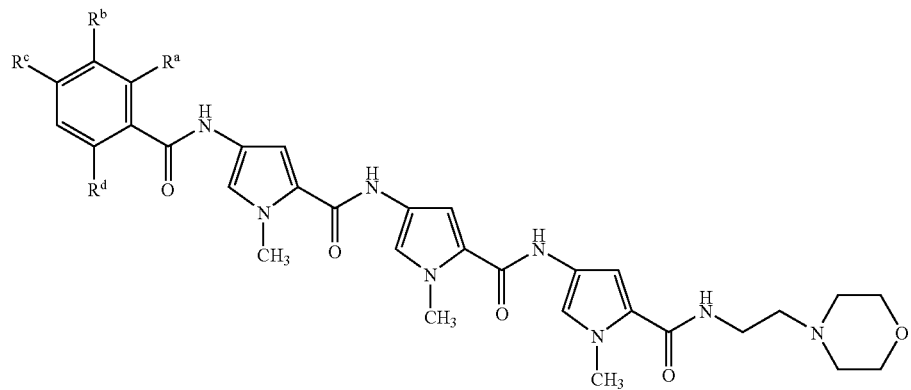

Scheme 9

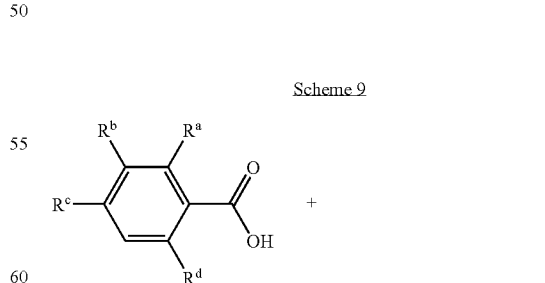

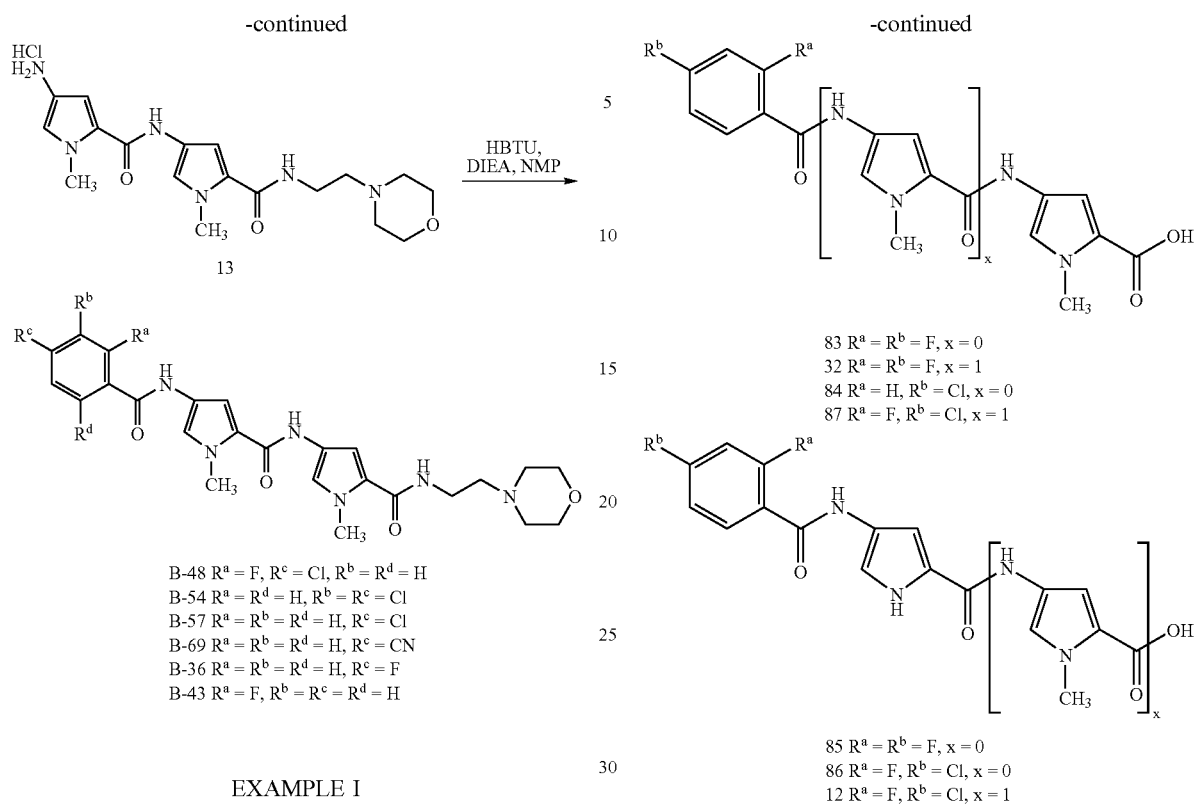

83 $R^a = R^b = F$, x = 0
32 $R^a = R^b = F$, x = 1
84 $R^a = H$, $R^b = Cl$, x = 0
87 $R^a = F$, $R^b = Cl$, x = 1

85 $R^a = R^b = F$, x = 0
86 $R^a = F$, $R^b = Cl$, x = 0
12 $R^a = F$, $R^b = Cl$, x = 1

B-48 $R^a = F$, $R^c = Cl$, $R^b = R^d = H$
B-54 $R^a = R^d = H$, $R^b = R^c = Cl$
B-57 $R^a = R^b = R^d = H$, $R^c = Cl$
B-69 $R^a = R^b = R^d = H$, $R^c = CN$
B-36 $R^a = R^b = R^d = H$, $R^c = F$
B-43 $R^a = F$, $R^b = R^c = R^d = H$

EXAMPLE I

Scheme 11 depicts the synthesis of carboxylic acid intermediates that can be coupled with an amine to make compounds of this invention, as described later herein.

Scheme 11

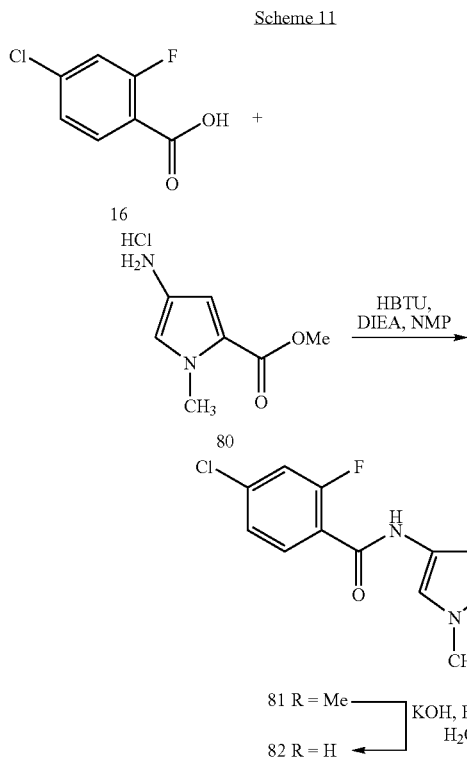

Specific procedures are given below for carboxylic acid 82, but acids 12, 32, and 83-87 were prepared analogously.

Ester 81

4-Chloro-2-fluorobenzoic acid 16 (3.77 g, 1.2 equiv.) and amino ester 80 (3.42 g, 1.0 equiv.) were coupled according to Procedure A using HBTU (7.77 g, 1.14 equiv.). Workup according to Procedure G yielded ester 81, which was used for the next step without further purification.

Compound 82

Crude ester 81 was saponified according to Procedure H to yield carboxylic acid 82 (4.72 g, 88% over two steps, $^1$H-NMR).

EXAMPLE J

Scheme 12 describes the synthesis of carboxylic acid building blocks containing a pyrrole unit that bears a 3-hydroxypropyl, an ethyl or a cyclopropylmethyl group at the ring nitrogen. Experimental details are given for the synthesis of compounds 101, 102, 113 and 114, other building blocks being prepared analogously.

Scheme 12

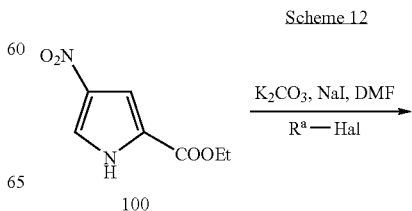

-continued

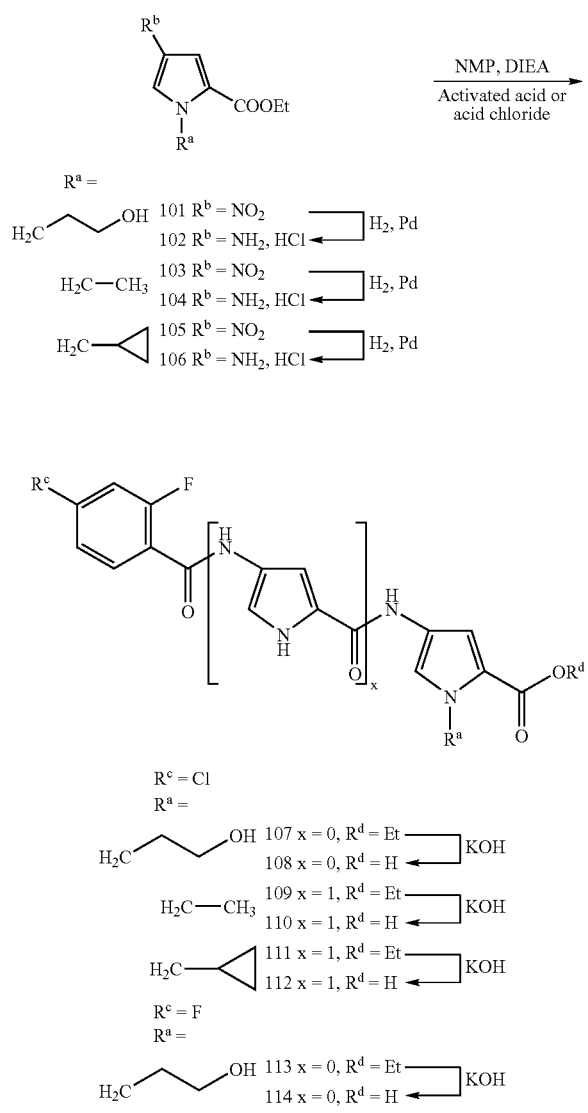

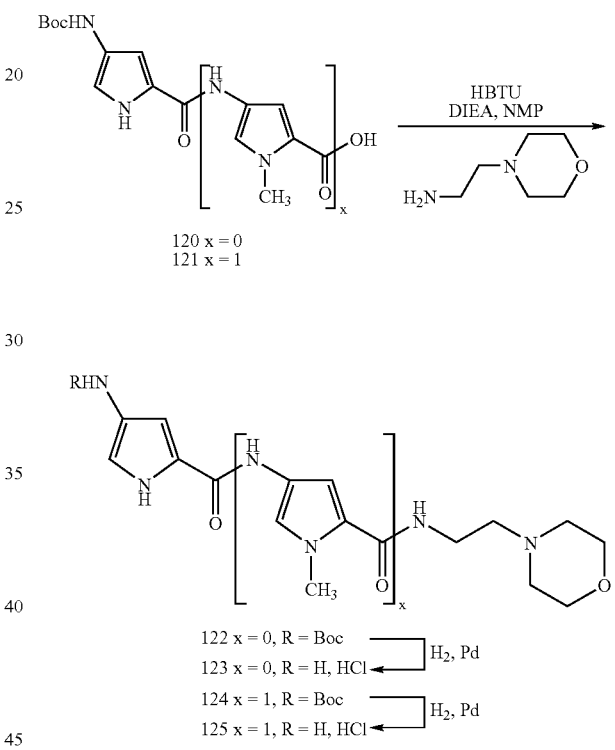

evaporated to give compound 113 as an orange oil that was used without further purification.

Compound 114

Crude compound 113 was saponified according to Procedure H to give compound 114 as pale yellow solid ($^1$H-NMR).

EXAMPLE K

Scheme 13 describes the synthesis of the heterocyclic amines containing an unsubstituted pyrrole carboxamide unit. These amines can be coupled with carboxylic acids to make compounds of this invention, as described later herein.

Compound 101

A suspension of pyrrole 100 (20.0 g, 1.0 equiv.), 3-bromopropanol (13.75 mL, 1.4 equiv.), NaI (16.28 g, 1.0 equiv.) and $K_2CO_3$ (30.0 g, 2.0 equiv.) in DMF (200 mL) was stirred at 65° C. for 2 h. The mixture was poured into $H_2O$ (700 mL) and extracted with $Et_2O$ (3×). The combined organic layers were dried ($MgSO_4$) and evaporated to give compound 101 (27.2 g, $^1$H-NMR).

Compound 102

Compound 101(18 g) was hydrogenated according to Procedure I to give compound 102 (16.6 g, 92%, $^1$H-NMR).

Compound 113

2,4-Difluorobenzoyl chloride (3.12 g, 1.1 equiv.) and amine 102 (4.00 g, 1.0 equiv.) were coupled according to Procedure D. The mixture was treated with $H_2O$ (300 mL) and sat. aqueous $K_2CO_3$ (25 mL) and extracted with AcOEt (2×). The combined organic layers were dried ($MgSO_4$) and Compounds 122/123

Carboxylic acid 120 (5.00 g, 1.0 equiv.) and 4-(2-aminoethyl)morpholine (4.35 mL, 1.5 equiv.) were coupled according to Procedure B using HBTU (9.22 g, 1.1 equiv.). The reaction mixture was poured into ice-water (ca. 300 mL) and sat. aqueous $K_2CO_3$ (20 mL) and extracted with $Et_2O$ (4×). The combined organic layers were dried ($MgSO_4$) and evaporated. Flash chromatography (1% $Et_3N$ in $CH_2Cl_2$/0 to 10% MeOH) gave compound 122 (760 mg). A solution of compound 122 (760 mg) in AcOEt (20 mL) was treated with HCl-saturated AcOEt (75 mL) and stirred is for 3 h at 0° C. The solids were collected by filtration and dried to give compound 123 (615 mg, $^1$H-NMR).

EXAMPLE L

Scheme 14 depicts the synthesis of heterocyclic amine building blocks containing a hydroxypropyl substituent at a pyrrole nitrogen.

Scheme 14

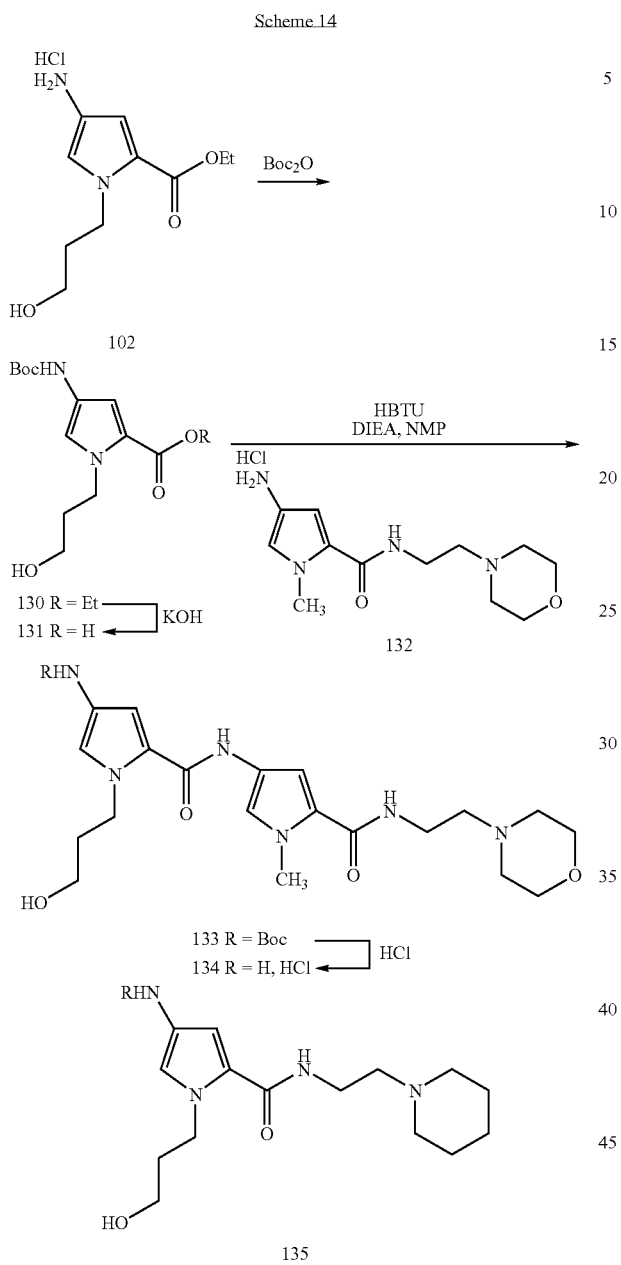

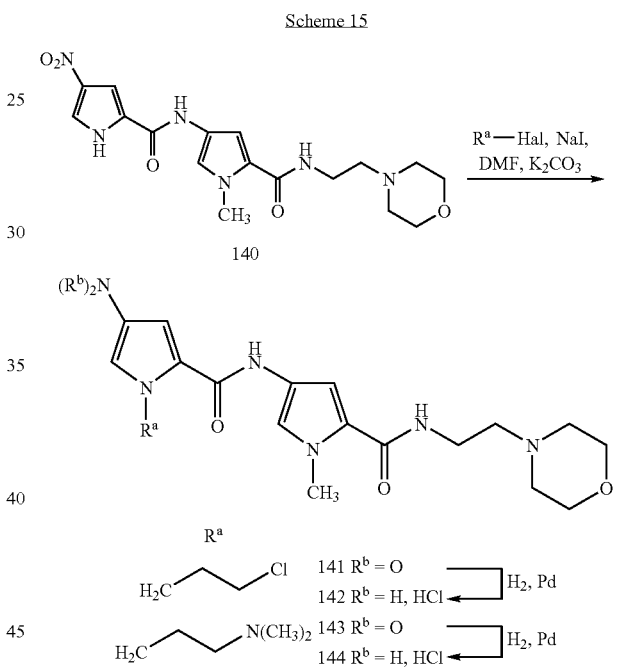

(MgSO$_4$) and evaporated to give compound 133 as an orange tar that was used without further purification. A solution of the crude compound 133 in AcOEt (ca. 60 mL) was treated with HCl (g), stirred for 2.5 h at RT and evaporated to give amine 134 (1.06 g) as a hygroscopic brown solid.

Compound 135

Amine 135 was prepared by coupling (Procedure A) acid 131 and 1-(2-aminoethyl)piperidine followed by cleavage of the Boc-group using HCl.

EXAMPLE M

Scheme 15 illustrates the synthesis of more intermediate amines having a pyrrole bearing a substituent other than methyl on the ring nitrogen, with compound 142 as an example.

Compound 130

A solution of amine 102 (31.75 g, 1.0 equiv.) and Boc$_2$O (26.87 g, 1.2 equiv.) in dioxane (100 mL) was treated with a sat. aq. Na$_2$CO$_3$ (12 g), stirred at RT for 24 h, diluted with H$_2$O, and extracted with AcOEt (4×). The combined organic layers were dried (MgSO$_4$) and evaporated to give compound 130 as a red tar ($^1$H-NMR).

Acid 131

Compound 130 (ca. 34 g) was saponified using Procedure H to give acid 131 as a sticky solid ($^1$H-NMR).

Compounds 133/134

Acid 131 (1.54 g, 1.1 equiv.) and amine 132 (1.60 g, 1.0 equiv.) were coupled according to Procedure A using HBTU (1.96 g, 1.05 equiv.). The reaction mixture was poured into H$_2$O (150 mL) and sat. aqueous K$_2$CO$_3$ (20 mL) and extracted with AcOEt (4×). The organic layers were dried Nitro compound 141

A mixture of dimer 140 (1.00 g, 1.0 equiv.), K$_2$CO$_3$ (885 mg, 2.5 equiv.) and 1-chloro-3-iodopropane (0.44 mL, 1.6 equiv.) in DMF (10 mL) was stirred at 65° C. for 3 h, poured into H$_2$O (135 niL) and sat. aqueous K$_2$CO$_3$ (20 mL) and extracted with AcOEt (3×). The organic layers were dried (MgSO$_4$) and evaporated to give nitro compound 141 (0.86 g, 72%, $^1$H-NMR, mass spectrum).

Amine 142

Nitro compound 141 (0.86 g) was hydrogenated using Procedure I to give amine 142 as a brown solid (0.923 g, >95%).

EXAMPLE N

Scheme 16 describes an alternative synthesis of intermediate amines having a substituent on a pyrrole nitrogen.

Scheme 16

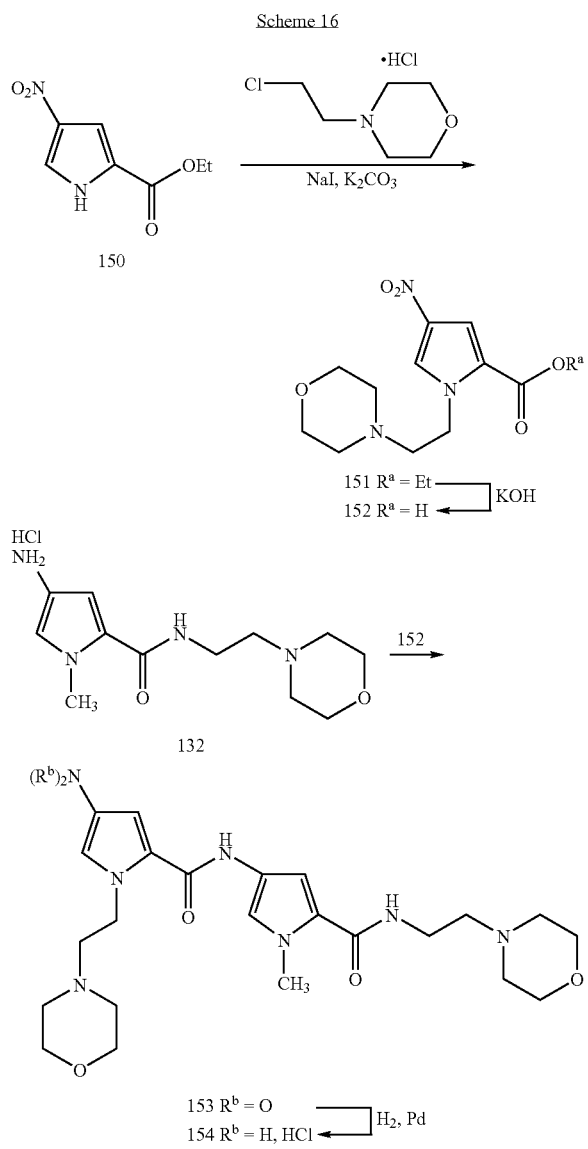

were dried (MgSO₄) and evaporated to give compound 153, which was then hydrogenated using Procedure I to give compound 154, which was used without further purification.

EXAMPLE O

Scheme 17 describes the synthesis of additional building blocks having a substituent on a pyrrole ring nitrogen. Intermediates 160 to 163 were made by analogy to intermediates 151 and 152 (vide supra). Compounds 164, 166 and 168 were prepared by coupling 1-(2-aminoethyl)piperidine to the corresponding acids 161, 152, and 162 using Procedure B. Intermediates 165, 167 and 169 were prepared by hydrogenation of the corresponding nitro-pyrroles 164, 166, and 168, respectively.

Scheme 17

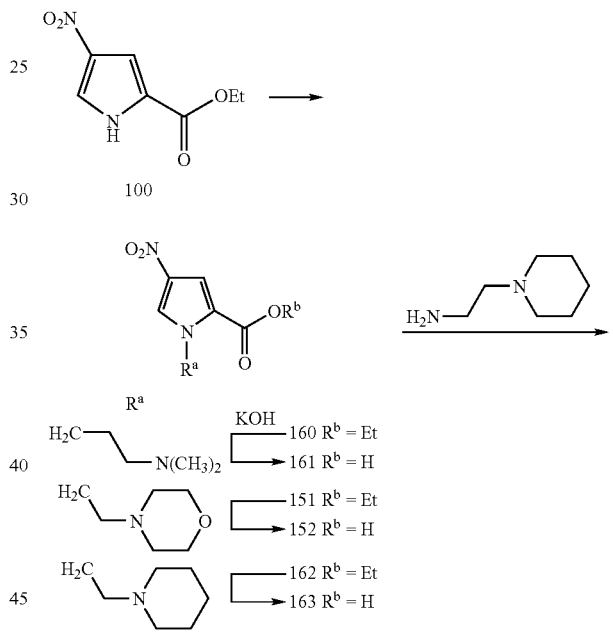

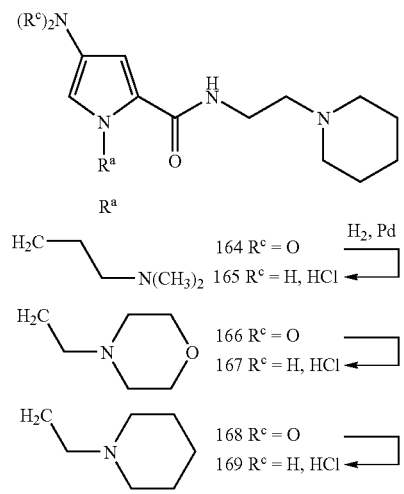

Ester 151

A mixture of ethyl 4-nitropyrrole-2-carboxylate 150 (20.00 g, 1.0 equiv.), 4-(2-chloroethyl)morpholine hydrochloride (28.28 g, 1.4 equiv.), NaI (16.28 g, 1.0 equiv.) and K₂CO₃ (28.78 g, 1.92 equiv.) in DMF (200 mL) was stirred at 60° C. for 10.5 h and poured into a mixture of H₂O and saturated aq. K₂CO₃ (550/50 mL). The resulting solution was extracted with AcOEt (4×, each 200 mL). The combined organic layers were dried (MgSO₄) and evaporated to give ester 151 as pale yellow crystals (31.4 g, 97%, ¹H-NMR).

Acid 152

Ester 151 (31.4 g, 1.0 equiv.) was saponified using Procedure H to give acid 152 as a white solid (23.0 g, 81%, ¹H-NMR).

Compounds 153/154

Acid 152 (1.04 g, 1.1 equiv.) and amine 132 (1.00 g, 1.0 equiv.) were coupled according to Procedure A using HBTU (1.22 g, 1.05 equiv.). The reaction mixture was poured into H₂O (150 mL) and sat. aqueous K₂CO₃ (20 mL) and extracted with AcOEt (5×). The combined organic layers

EXAMPLE P

Scheme 18 describes the synthesis of a building block having a methoxy-methyl substituent on a pyrrole ring nitrogen.

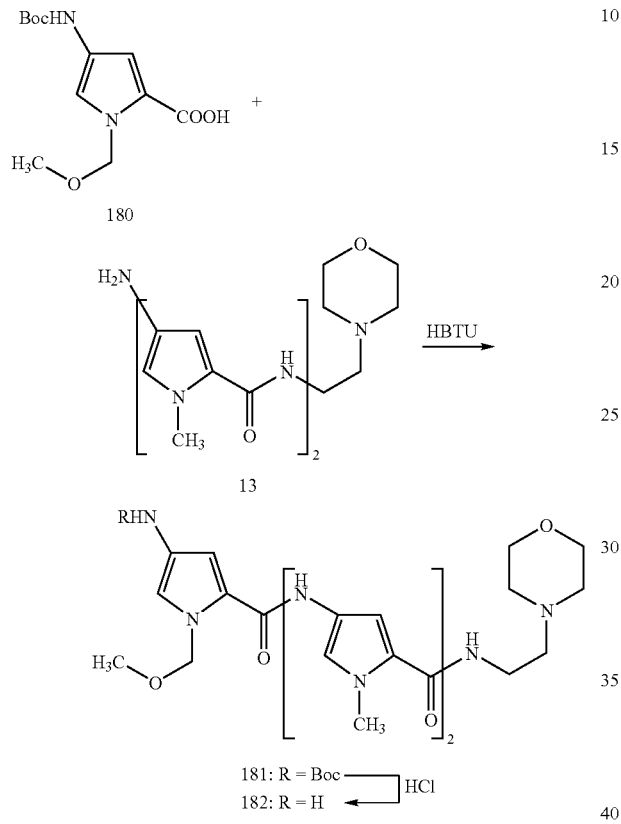

Compounds 181/182

Carboxylic acid 180 (1.66 g, 1.1 equiv.) and amine 13 (2.50 g, 1.0 equiv.) were coupled according to Procedure A using HBTU (2.22 g, 1.05 equiv.). The crude product was poured into H$_2$O (300 mL) and extracted with AcOEt (4×). The combined organic layers were dried (MgSO$_4$) and evaporated to give a brown oil. Flash chromatography (CH$_2$Cl$_2$ and 0→15% MeOH gradient) gave 181 (1.7 g) as a glassy solid. The material was dissolved in AcOEt (50 mL), treated with HCl-saturated AcOEt (50 mL) and stirred at RT for 1½h. Evaporation of the solvent gave amine 182 (1.49 g) as a tan solid. The $^1$H-NMR spectrum and the mass spectrum were consistent with the structure of amine 182. However, the $^1$H-NMR spectrum showed signals of minor impurities that were not further characterized.

EXAMPLE Q

Applying convergent synthesis principles to the amine and acid building blocks whose syntheses were described in preceding Examples I through P above and to building blocks 190 through 192 shown below, compounds of this invention were made as tabulated in Table H.

TABLE H

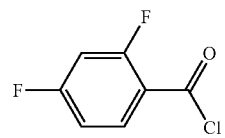

190

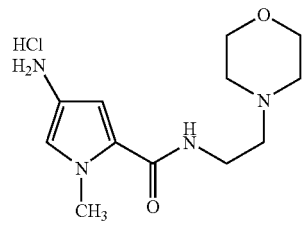

191

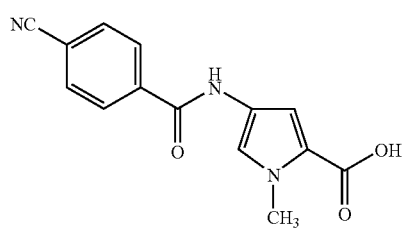

192

| Carboxylic acid | Amine | Procedure (coupling) | Procedure (purification) | Product |
|---|---|---|---|---|
| 32 | 123 | A | F | C-1 |
| 83 | 125 | A | F | C-2 |
| 85 | 125 | A | F | C-3 |
| 83 | 133 | A | F | C-4 |
| 85 | 133 | A | F | C-5 |
| 114 | 13 | A | F | C-6 |
| 190 | 182 | D | E | C-7 |
| 12 | 123 | A | F | C-8 |
| 12 | 134 | A | F | C-9 |
| 82 | 125 | A | F | C-10 |
| 86 | 125 | A | F | C-11 |
| 110 | 191 | A | F | C-12 |
| 112 | 191 | A | F | C-13 |
| 82 | 133 | A | F | C-14 |
| 86 | 133 | A | F | C-15 |
| 108 | 13 | A | F | C-16 |
| 5b | 182 | D | E | C-17 |
| 82 | 142 | A | F | C-18 |
| 86 | 142 | A | F | C-19 |
| 32 | 165 | A | F | D-2 |
| 32 | 169 | A | F | D-5 |
| 83 | 144 | A | F | D-7 |
| 12 | 167 | A | F | D-13 |
| 12 | 169 | A | F | D-14 |
| 82 | 144 | A | F | D-25 |
| 86 | 144 | A | F | D-26 |
| 84 | 155 | A | F | D-27 |

EXAMPLE R

This example illustrates the synthesis of compounds having a C-terminal 3-methyl-isothiazole moeity. Also illustrated is the introduction of a pendant charged side chain by mesylation of a pendant alcohol, followed by substitution using an amine.

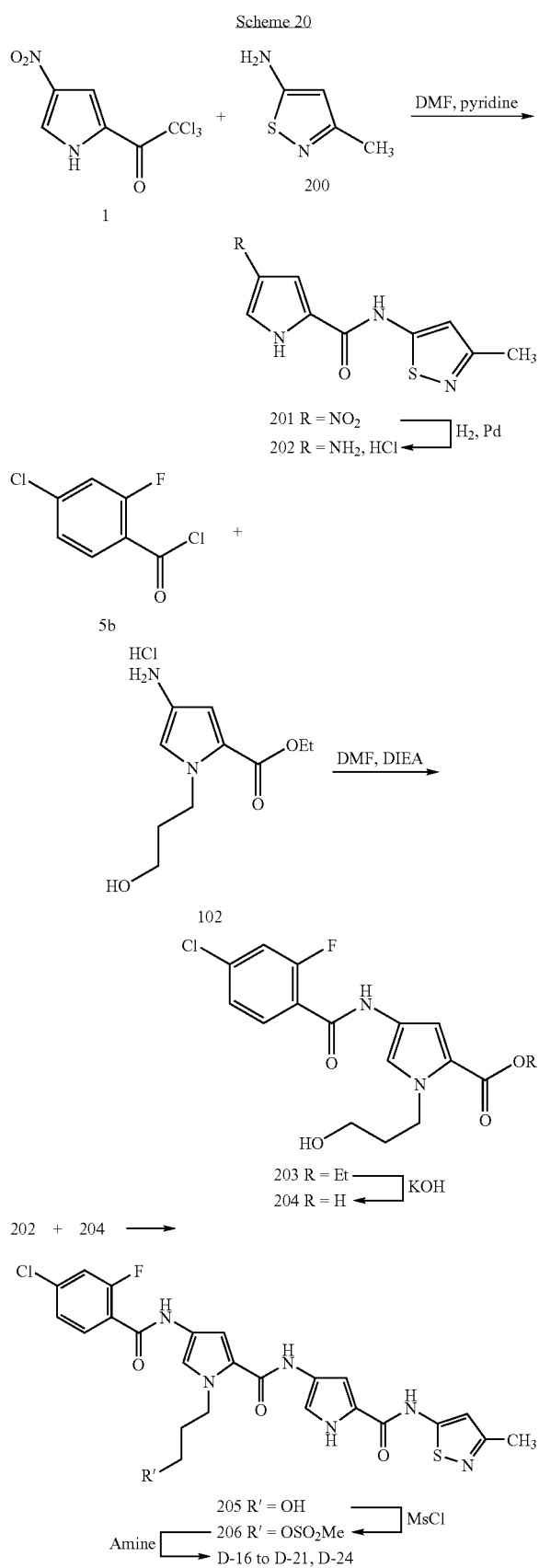

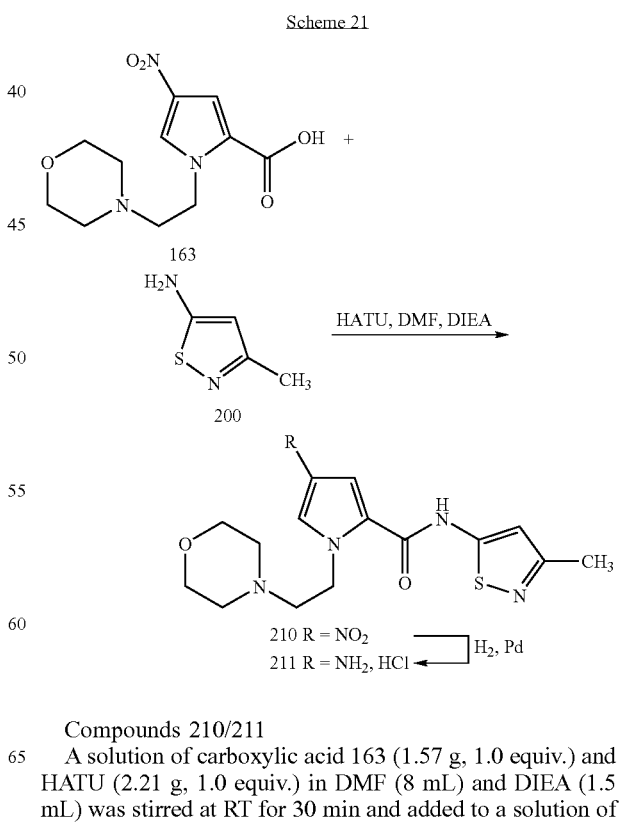

Compound 201

A solution of ketone 1 (50.00 g, 1.05 equiv.) and amine 200 (29.15 g, 1.0 equiv.) in DMF (300 mL) and pyridine (75 mL) was stirred at 65° C. for 22 h. Workup according to Procedure G gave dimer 201 (48.9 g, >95%, $^1$H-NMR).

Compound 202

Dimer 201(5.0 g) was hydrogenated using Procedure I to give compound 202 ($^1$H-NMR).

Ester 203 and acid 204

Acid chloride 5b (3.41 g, 1.1 equiv.) and amino ester 102 (4.00 g, 1.0 equiv.) were coupled according to Procedure D. The reaction mixture was diluted with $H_2O$ (300 mL) and sat. aqueous $K_2CO_3$ (25 mL), extracted with AcOEt (2×), dried ($MgSO_4$) and evaporated to give ester 203 as an orange oil. Saponification of crude ester 203 according to Procedure H gave acid 204 as a white solid ($^1$H-NMR).

Alcohol 205

Acid 204 (722 mg, 1.1 equiv.) and amine 202 (0.50 g, 1.0 equiv.) were coupled according to Procedure A using HBTU (0.77 g, 1.05 equiv.). The reaction mixture was poured into $H_2O$ (150 mL) and extracted with AcOEt (7×). The combined organic layers were dried ($MgSO_4$) and evaporated. Flash chromatography ($CH_2Cl_2$/0%→15% MeOH gradient) gave alcohol 205 (358 mg, 34%, $^1$H-NMR, mass spectrum).

Compounds 206/D-16

A solution of alcohol 205(25 mg, 1.0 equiv.) in DMF (1 mL) and DIEA (0.1 mL) was treated at RT with MsCl (15.8 mg, 3 equiv.), stirred for 70 min, treated with pyrrolidine (0.5 mL) and stirred at 55° C. for 16 h to give compound D-16 after purification according to procedure E.

EXAMPLE S

Schemes 21 and 22 describe the synthesis of C-terminal building blocks containing a 3-methyl-isothiazole unit.

Compounds 210/211

A solution of carboxylic acid 163 (1.57 g, 1.0 equiv.) and HATU (2.21 g, 1.0 equiv.) in DMF (8 mL) and DIEA (1.5 mL) was stirred at RT for 30 min and added to a solution of isothiazole 200 (0.88 g, 1.0 equiv.) in DMF (5 mL) and DIEA (1 mL). The mixture was stirred at 60° C. for 8 h, treated with H₂O and extracted (AcOEt, 3×). The combined organic layers were dried (MgSO₄) and evaporated to give crude compound 210, which was hydrogenated using Procedure H to give compound 211, used without further purification.

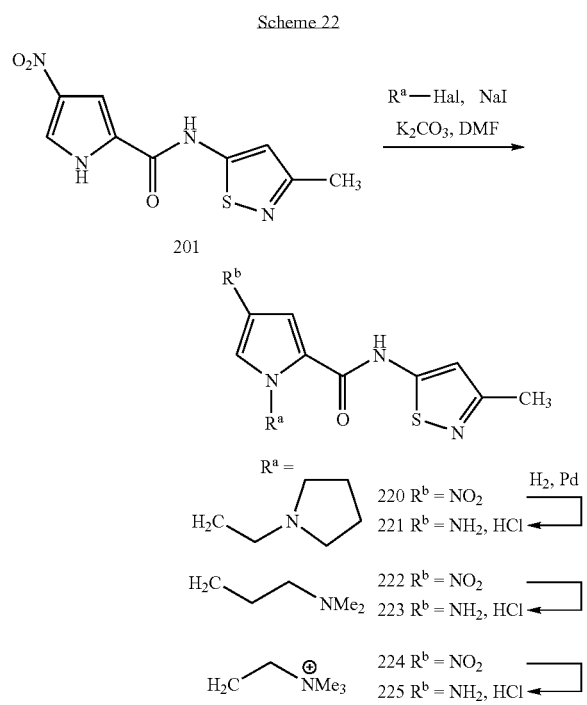

Compounds 220/221

A suspension of dimer 201 (3.0 g, 1.0 equiv.), 1-(2-chloroethyl)pyrrolidine (HCl, 2.83 g, 1.4 equiv.), NaI (1.96 g, 1.1 equiv.) and K₂CO₃ (3.29 g, 2.0 equiv.) in DMF (30 mL) was stirred at 65° C. for 7 h, treated with additional 1-(2-chloroethyl)pyrrolidine (.HCl, 3.0 g) and stirred for 30 h at 65° C. The reaction mixture was diluted with H₂O (150 mL) and sat. aqueous K₂CO₃ (10 mL) and extracted with AcOEt (5×). The combined organic layers were dried (MgSO₄) and evaporated to give crude product 220 (3.36 g). The ¹H-NMR indicated that product 220 was a mixture of two compounds. The crude product 220 (3.36 g) was hydrogenated using Procedure I to give compound 221 plus at least one unidentified by-product, which was used without further purification. Compounds 222 to 225 were prepared in a similar fashion.

The building blocks described above were coupled under standard coupling conditions as summarized in the following Table I.

TABLE I

| Carboxylic acid | Amine | Procedure (coupling) | Procedure (purification) | Product |
|---|---|---|---|---|
| 83 | 211 | A | F | D-1 |
| 85 | 211 | A | F | D-4 |
| 82 | 211 | A | F | D-8 |
| 86 | 211 | A | F | D-9 |
| 84 | 211 | A | F | D-28 |
| 192 | 211 | A | F | D-29 |

TABLE I-continued

| Carboxylic acid | Amine | Procedure (coupling) | Procedure (purification) | Product |
|---|---|---|---|---|
| 83 | 223 | A | F | D-3 |
| 83 | 225 | A | F | D-6 |
| 86 | 221 | A | F | D-10 |
| 86 | 223 | A | F | D-11 |
| 82 | 223 | A | F | D-12 |
| 82 | 225 | A | F | D-22 |
| 86 | 225 | A | F | D-23 |

Compound G-2 was obtained as a by-product of the synthesis of compound D-10, indicating that the unidentified by-product in the synthesis of compound 221 was a doubly alkylated bis-ethylpyrrolidine.

EXAMPLE T

This example illustrates the synthesis of compounds having a C-terminal 3-othiazole moiety and an N-terminal benzamide unit that contains a halogen (F, Cl) at position 4 and a NHR or a SR substituent at position 2, using compound C-24 as a model. Generally, the compounds were prepared from precursors having an N-terminal 2,4-difluorobenzamide or a 4-chloro-2-fluorobenzamide unit. In the presence of an appropriate nucleophile (e.g., amine, thiolate), these N-terminal units undergo a nucleophilic aromatic substitution replacing the fluoride at position 2 of the benzene ring.

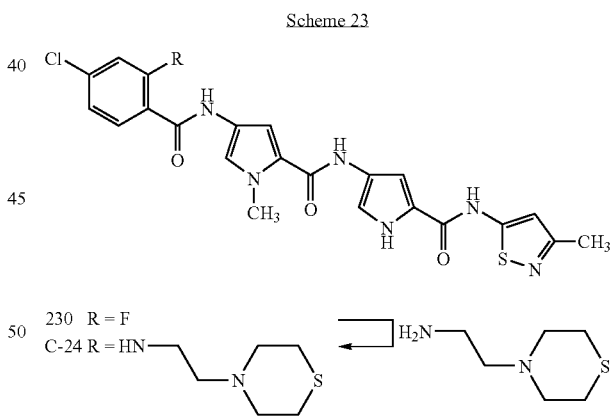

Compound C-24

A mixture of tetramer 230 (prepared from the intermediates 82 and 202, respectively: 100 mg, 1.0 equiv.) and 4-(2-aminoethyl)thiomorpholine (0.3 mL) in NMP (0.7 mL) was stirred at 55° C. for 17 h. Purification according to Procedure E gave compound C-24.

EXAMPLE U

This example illustrates the synthesis of a building block having a 2,4-disubstituted thiophene ring.

Scheme 24

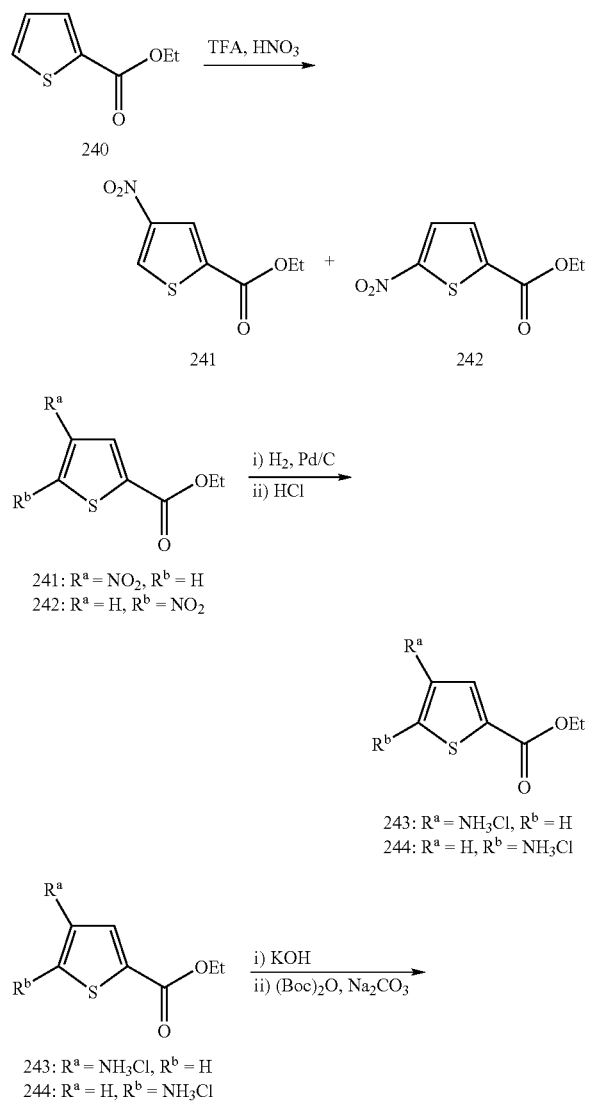

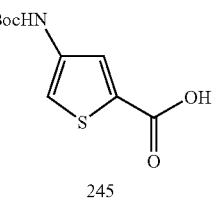

Compounds 241/242

A solution of ethyl-2-thiophene carboxylate 240 (200 g, 1 mol) in TFA (200 mL) was slowly added to a mixture of TFA (900 mL) and fuming nitric acid (200 mL) at 5° C. The cooling was removed and the reaction mixture stirred at 45° C. for ca. 14 h, cooled to ca. 10° C., and poured into vigorously stirred ice water (4 L). The resulting precipitate was collected by filtration and washed with ice water (2×). Lyophilization gave a mixture of compounds 241/242 (2:3 by $^1$H-NMR, 194.2 g, 79%)

Compounds 243/244

The mixture of compounds 241/242 (2:3, 20 g) was hydrogenated using Procedure I to give a mixture of compounds 243/244 (0.9:1 as evidenced by $^1$H-NMR, 19.02 g, 93%).

Acid 245

Compound 243 was selectively saponified by treating a mixture of compounds 243/244 (0.9/1, 15 g) in methanol (500 mL) at 0° C. with a solution of KOH (9 g) in H$_2$O (75 mL) and stirring for 3 h. The reaction mixture was then diluted with H$_2$O (400 mL) and washed with EtOAc (3×, 200 mL). The aqueous layer was neutralized to pH=6.5 with 1 M aq. HCl, treated with Na$_2$CO$_3$ (15 g) and a solution of Boc anhydride (15 g) in dioxane (150 mL) and stirred for 24 h at RT. The reaction mixture was washed with EtOAc (3×, 200 mL), cooled to 0° C., acidified to pH=2.8 with aqueous HCl (50%), and extracted with EtOAc (3×, 200 mL). The combined organic layers were dried (MgSO$_4$) and evaporated. The remaining oil was dissolved in methanol and treated with activated carbon (5 g). The mixture was filtered through Celite and the filtrate evaporated to yield acid 245.

EXAMPLE V

Scheme 25 illustrates the synthesis of compounds incorporating a thiophene moiety from building block acid 245, compound E-14 as an exemplar.

Scheme 25

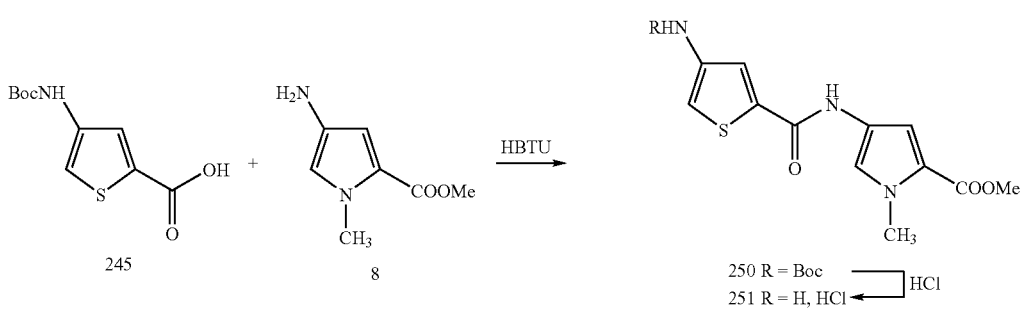

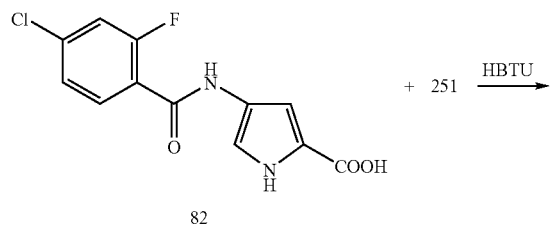

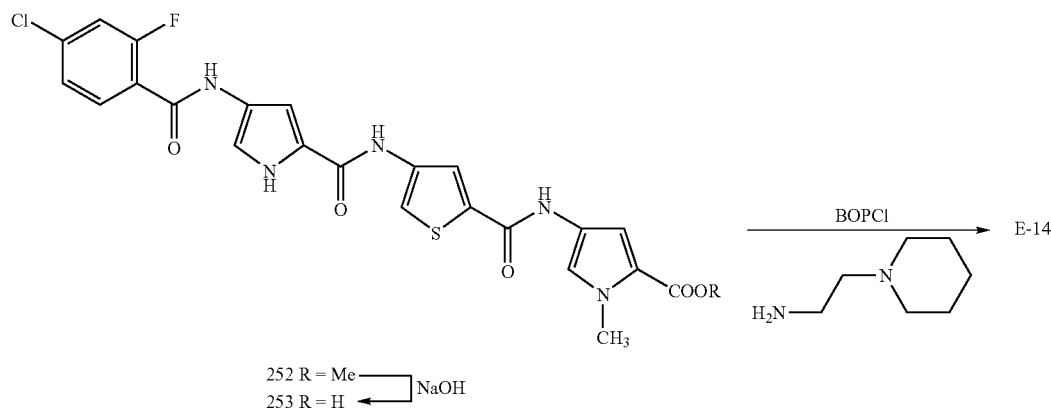

Compounds 250/251

Acid 245 (4.93 g, 1.2 equiv.) and amino ester 8 (3.22 g, 1.0 equiv.) were coupled according to Procedure A using HBTU (7.29 g, 1.14 equiv.). Workup according to Procedure G gave compound 250, which was then dissolved in AcOEt (200 mL) at 0° C., treated with HCl (g) and stirred for 2 h at RT. The solids were collected by filtration to give amino ester 251 (4.92 g, 92% two steps, $^1$H-NMR).

Compounds 252/253

Acid 82 (1.07 g, 1.2 equiv.) and amino ester 251 (1.00 g, 1.0 equiv.) were coupled according to Procedure A using HBTU (1.36 g, 1.14 equiv.). Workup according to Procedure G gave tetramer 252 (1.86 g). According to the $^1$H-NMR spectrum, this material contained minor impurities. Tetramer 252 (1.86 g, 1.0 equiv.) was saponified using Procedure H to give acid 253 (0.75 g).

Compound E-14

Acid 253 (80 mg, 1.0 equiv.) and 1-(2-aminoethyl)piperidine (0.5 mL) were coupled according to Procedure C using BOPCl (46 mg, 1.2 equiv.). Purification according to Procedure E gave compound E-14.

EXAMPLE W

Other compounds containing a thiophene-2-carboxamide moiety (such as compounds E-1 or E-10) can be made by a convergent synthesis using the appropriate building blocks. The synthesis of compound E-10 is shown in Scheme 26 as a representative example.

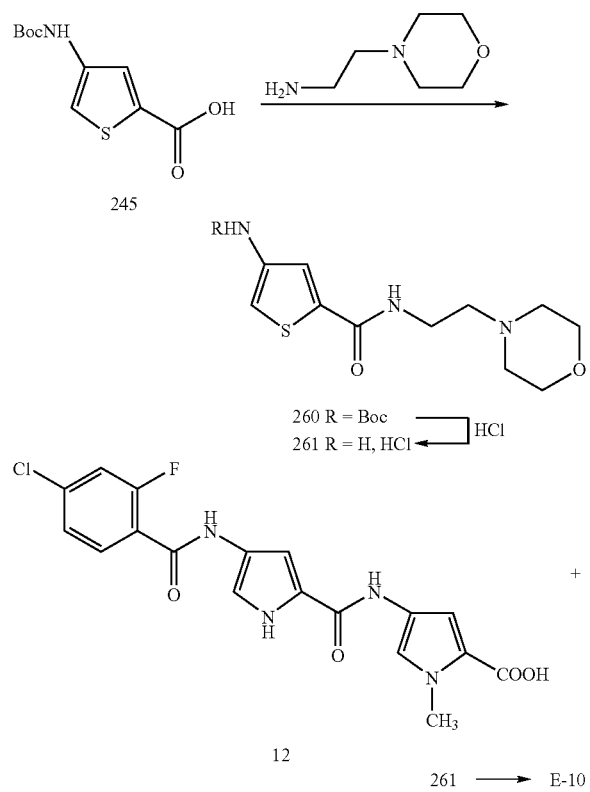

Scheme 26

Compounds 260/261

Acid 245 (4.00 g, 1.0 equiv.) and 4-2- aminoethyl)morpholine (6.5 mL, 2.5 equiv.) were coupled according to Procedure B using HBTU (6.85 g, 1.1 equiv.). The reaction mixture was poured into H$_2$O (300 mL) and extracted with Et$_2$O (4×). The combined organic layers were dried (MgSO$_4$) and evaporated to give compound 260 as a brown liquid. The material was treated with HCl-sat. AcOEt (200 mL), stirred at 0° C. for 1 h and treated with Et$_2$O (400 mL). The solvent was decanted and the remaining solids dried to give amine 261, which was used without further purification.

Compound E-10

Trimer 12 (100 mg, 1.2 equiv.) and amine 261(67.6 mg, 1.0 equiv.) were coupled according to Procedure A using HBTU (89 mg, 1.14 equiv.). Purification according to Procedure F gave compound E-10.

EXAMPLE X

This example describes the synthesis of compounds containing an imidazole moiety. The preparation of the dimeric imidazole intermediates 274 and 276 is illustrated in Scheme 27.

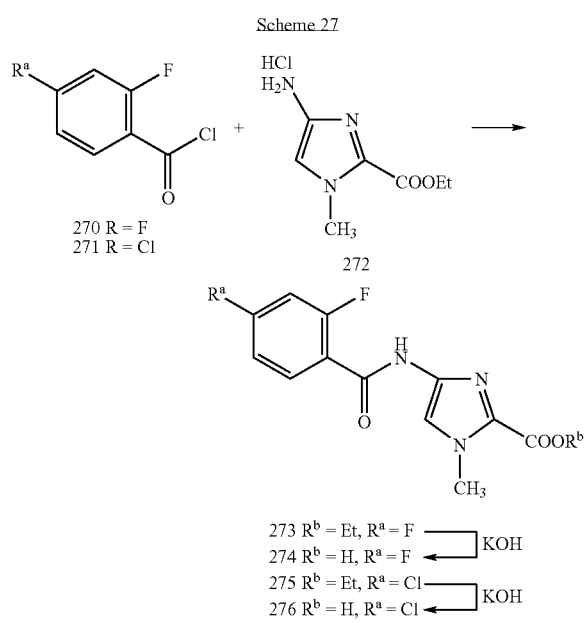

Compounds 273/274. Acid chloride 270 (1.12 mL, 1.3 equiv.) and amine 272 (1.50 g, 1.0 equiv.) were coupled according to Procedure D and purified according to Procedure G to give compound 273. Crude compound 273 was saponified using Procedure H to give compound 274 ($^1$H-NMR). Compound 276 was analogously prepared.

Compounds E-7, E-18, E-11, and E-12

Compound 274 was coupled to dimer 211 to give compound E-7 and to dimer 13 to yield compound E-18, using Procedure A and workup F. Similarly, compound 276 was coupled to the dimer 13 to yield compound E-11 and to the dimer 134 to yield compound E-12, using Procedures A and F.

EXAMPLE Y

This example describes the synthesis of compounds containing an isothiazole carboxamide moiety. The synthesis of compound E-2 is given in Scheme 28 as a representative example.

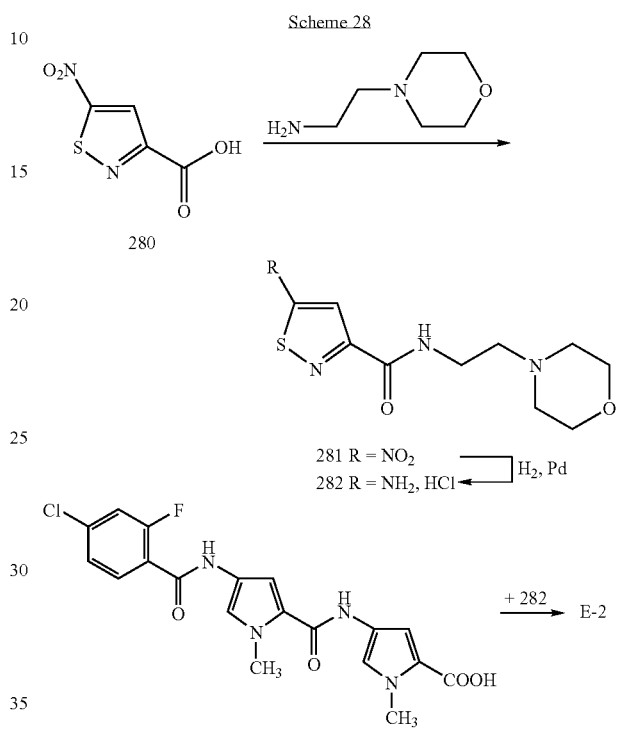

Compound 281

Nitro acid 280(300 mg, 1.2 equiv., Heindl et al., Eur. J. Med. Chem.—Chimica Therapeutica, 1975, 10, 591-593) and 4-(2-aminoethyl)morpholine (0.188 mL, 1.0 equiv.) were coupled according to Procedure B. The mixture was diluted with H$_2$O (ca. 40 mL) and extracted with AcOEt (3×). The combined organic layers were dried (MgSO$_4$) and evaporated to give compound 281 (450 mg, $^1$H-NMR).

Compound 282

Compound 281(450 mg, crude product from above procedure) was hydrogenated using Procedure I to give compound 282 as a light yellow powder (250 mg, ca. 90 to 95% pure by $^1$H-NMR). This material was subsequently used for the synthesis of compound E-2 without further purification.

Compound E-2

Trimeric acid 87 (99 mg, 1.2 equiv.) and amine 282 (60 mg, 1.0 equiv.) were coupled according to Procedure A using HATU (89 mg, 1.14 equiv.). Workup according to Procedure F gave compound E-2.

EXAMPLE Z

This example illustrates the synthesis of compounds containing an ester functionality at the C-terminus. Scheme 29 depicts the synthetic methodology for building blocks 292 and 294. Experimental details are given for building block 292, with building block 294 being prepared analogously.

Trimeric carboxylic acid 32 was subsequently coupled to the esters 292 and 294 using Procedure A to give compounds B-9 and B-10, respectively.

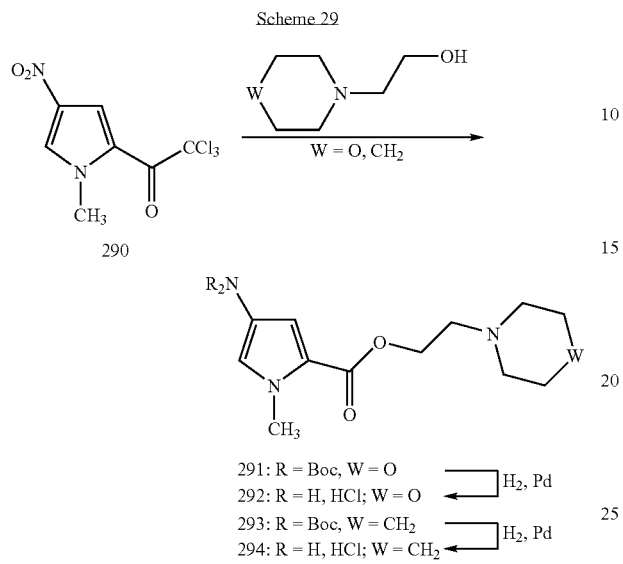

Compounds 291/292

A solution of 4-(2-hydroxyethyl)morpholine (3.4 mL, 3.0 equiv.) in THF (20 mL) was treated at 0° C. portionwise with NaH (0.37 g, 1.0 equiv., 60% dispersion in mineral oil). The mixture was stirred for 20 min until a clear solution was observed and treated with a solution of the ketone 290 (2.52 g, 1.0 equiv.) in THF (10 mL). The mixture was stirred for 3 h at 0° C., carefully diluted with sat. aqueous $K_2CO_3$ and AcOEt. The layers were separated and the aqueous phase extracted with AcOEt (3×). The combined organic layers were dried (MgSO$_4$) and evaporated to give compound 291 ($^1$H-NMR, mass spectrum). Crude compound 291 was hydrogenated using Procedure I to give compound 292, used without further purification.

EXAMPLE AA

This example illustrates the synthesis of compounds containing a 3-amino-5-carboxy isoxazole moiety, compounds E-3 to E-6, E-8 and E-19 being representative. Schemes 30 and 31 detail the preparation of compounds E-3 and E-8 as models.

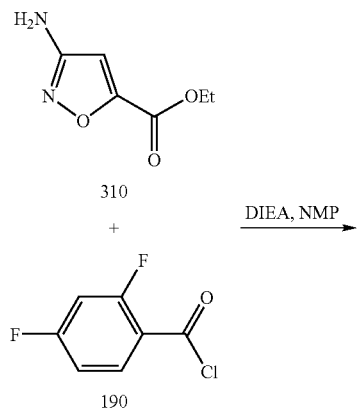

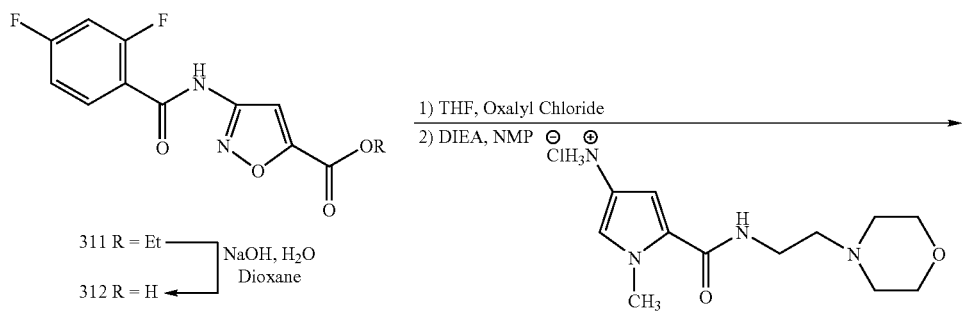

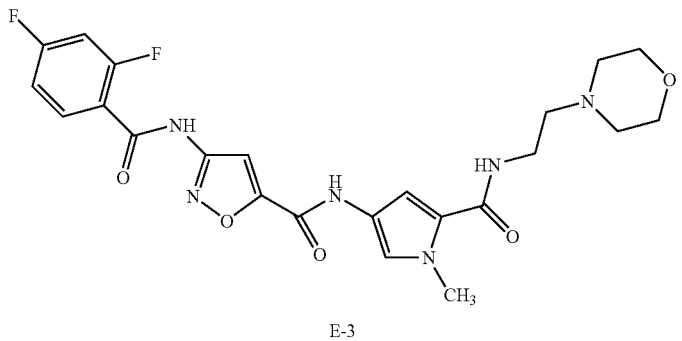

E-3

Compounds 311/312

Amine 310 [Lepage et aL, FR 2,750,425 (1998)] (294 mg, 1.88 mmol) and acid chloride 190 (231 µl, 1.88 mmol) were coupled according to Procedures D and G to give amide-ester 311 (550 mg). Amide-ester 311 (550 mg) was converted into acid 312 (500 mg) by saponification according to Procedure I, except that the organic solvent used was dioxane.

Compound E-3

Oxalyl chloride (131 µl, 1.5 mmol) was added to a suspension of acid 312 (31 mg, 0.12 mmol) in THF (I mL). The reaction mixture was heated at 80° C. for 2 hours. All volatile components were then removed under vacuum. A solution of amine 191(162 µl, 1.2 M solution in NMP, 0.194 mmol) in DMF (2 mL) and DIEA (0.5 mL) was then added and the reaction mixture was heated at 70° C. for 4 hours. Purification via Procedure E gave compound E-3.

Scheme 31

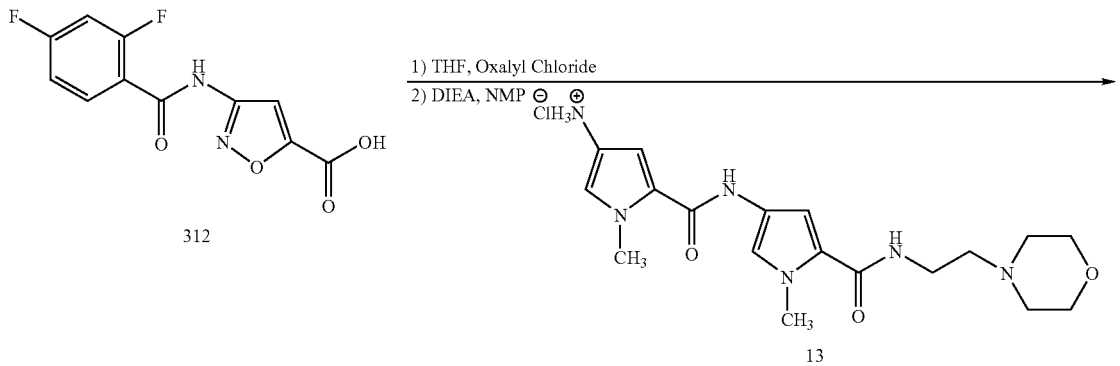

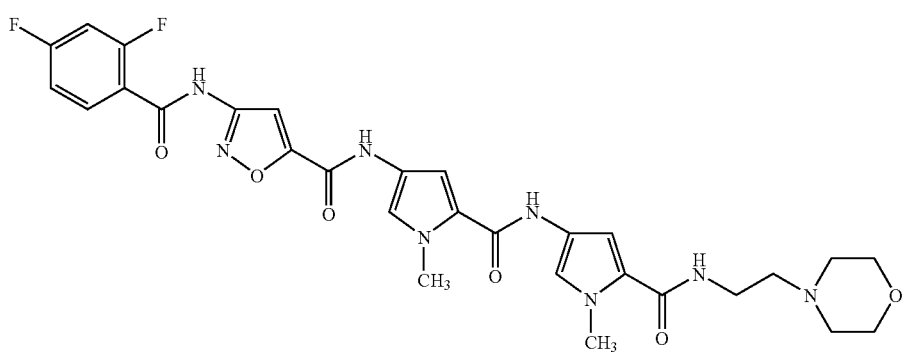

E-8

107

Compound E-8

Oxalyl chloride (85 µl, 0.97 mmol) was added to a suspension of acid 312 (26 mg, 0.097 mmol) in THF (1 mL). The reaction mixture was heated at 80° C. for 2 hours. All volatile components were then removed under vacuum. A solution of amine 13 (99 mg, 0.24 mmol) in DMF (2 mL) and DIEA (0.5 mL) was then added and the reaction mixture was heated at 70° C. for 4 hours. The reaction mixture was allowed to cool and was purified by Procedure E, giving compound E-8.

108

EXAMPLE BB

Scheme 32 illustrates the synthesis of compounds having a 2-amino-5-carboxy thiazole moiety adjacent to an N-terminal halogenated benzamide moiety, as represented by compound E-9.

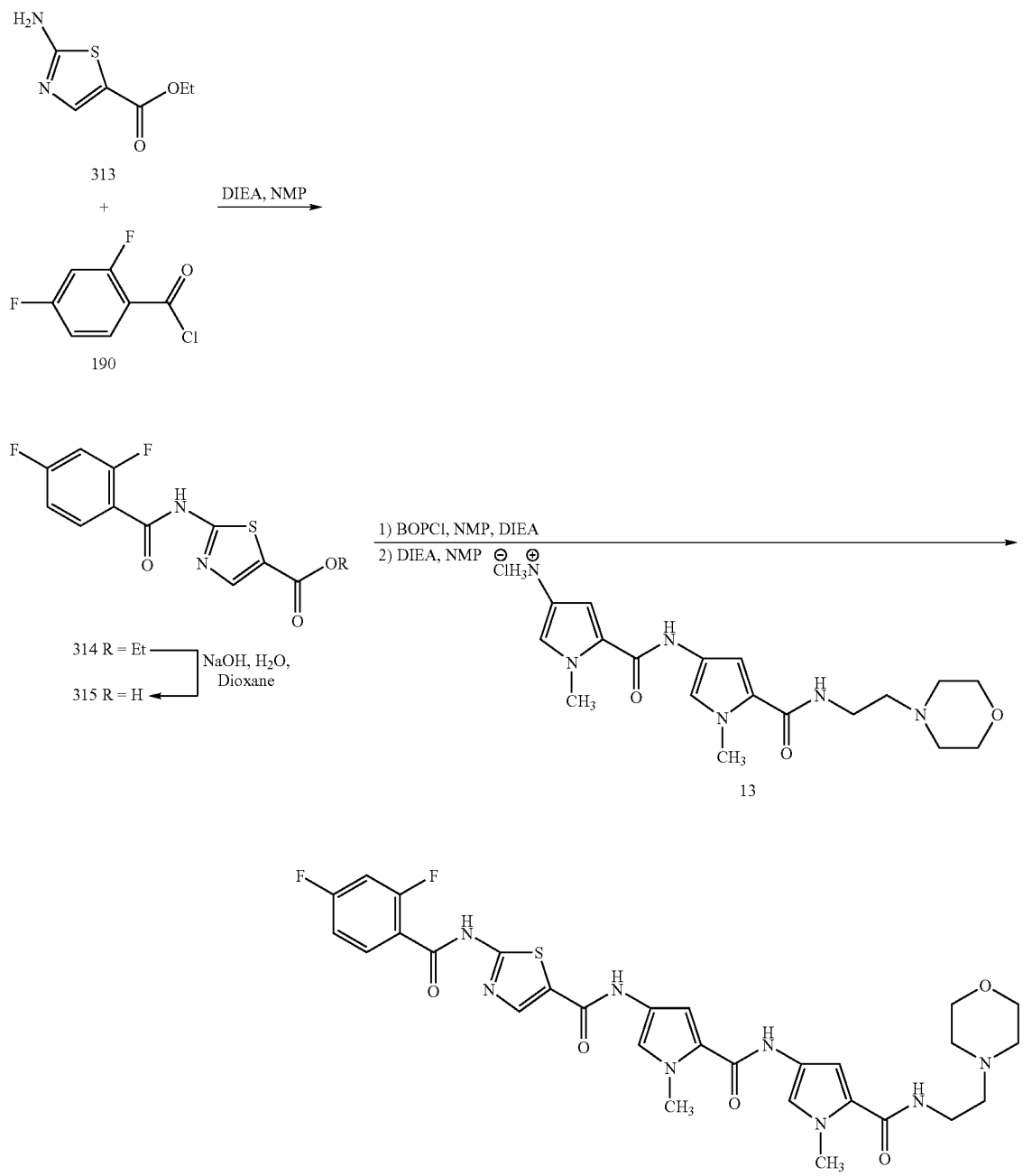

Compounds 314/315

Amine 313 (Henichart et al., *Heterocycles*, v.32, No.4, p. 693, 1991) (200 mg, 1.16 mmol) and acid chloride 190 (142 µl, 1.16 mmol) were coupled according to Procedure D. Workup according to Procedure G gave amide-ester 314 (360 mg). Amide-ester 314 (360 mg, 1.15 mmol) was saponified to give amide-acid 315 (300 mg) using Procedure H, except that the organic solvent used was dioxane.

Compound E-9

Amide-acid 315 (100 mg, 0.35 mmol) and amine 13 (144 mg, 0.35 mmol) were coupled according to Procedure C using BOPCl (89 mg, 0.35 mmol). Purification according to Procedure E gave product E-9.

EXAMPLE CC

This example illustrates the synthesis of compounds containing an internal 4-amino-benzoic acid moiety. Representative examples are compounds F-3 and F4.

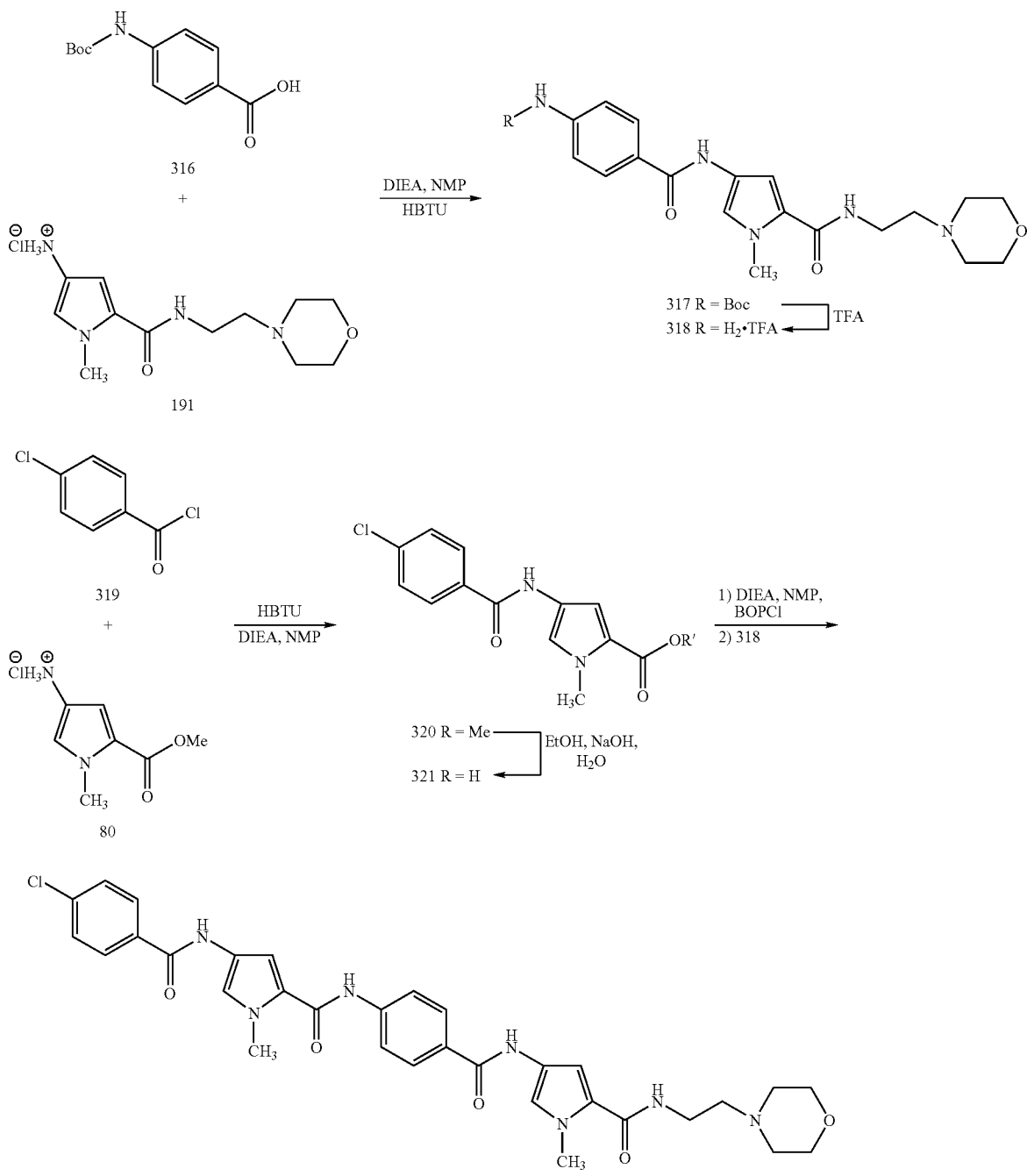

Scheme 33

F-4

Compounds 317/318

Amine 191 (1.95 mL, 35% weight solution in NMP, 3 mmol) and acid 319 (854 mg, 3.6 mmol) were coupled according to Procedure A using HBTU (1.25 g, 3.3 mmol). The reaction was poured into water and the product extracted into AcOEt (3×). The combined organic layers were dried (MgSO₄) and evaporated to give compound 317. Excess TFA was added and the reaction mixture was stirred at RT to remove the Boc group. Following removal of volatile components under vacuum, the TFA salt of amine 318 was obtained, which was used without further purification.

Compounds 320/321

Amine 80 (6.67 g, 35 mmol) and acid chloride 319 (4.89 mL, 38.5 mmol) were coupled according to Procedure D. Product 320 was obtained according to Procedure G. Crude product 320 was saponified using Procedure H to give 321 (9.4 g) as a pure white solid.

Compound F-4

Acid 321 (167 mg, 0.6 mmol) and amine 318 (0.5 mmol) were coupled according to Procedure C using BOPCl (140 mg, 0.55 mmol). Purification according to Procedure E gave the product F4.

EXAMPLE DD

This example illustrates the synthesis of more compounds containing a 4-aminobenzoic acid moiety, as represented by compound F-6.

Scheme 34

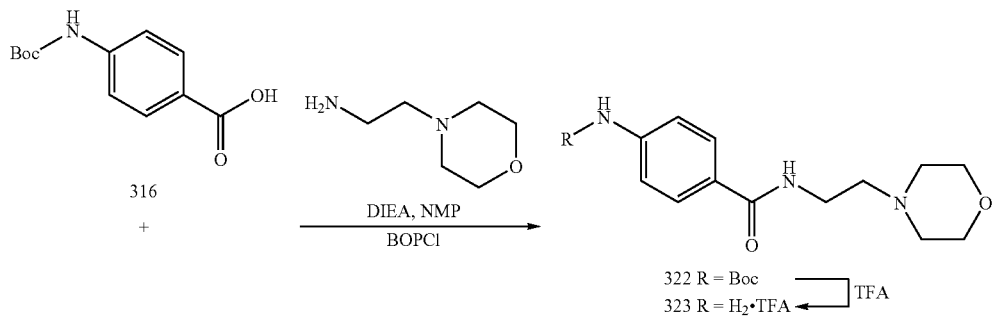

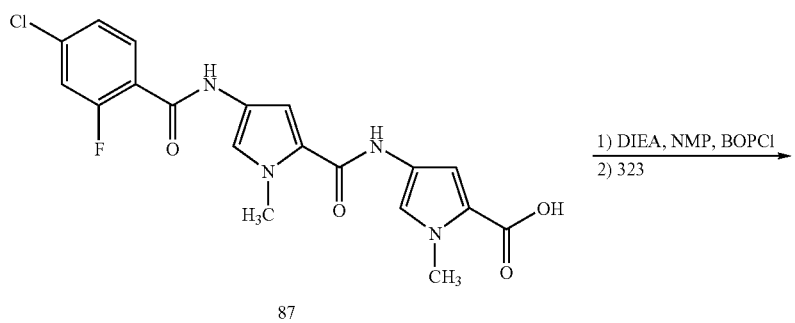

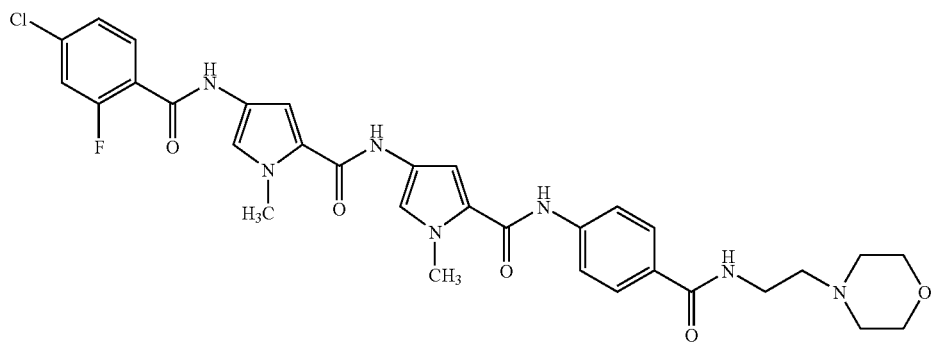

F-6

Compounds 322/323

Acid 316 (522 mg, 2.2 mmol) and 4-(2-aminoethyl) morpholine (260 μl, 2.0 mmol) were coupled according to Procedure C using BOPCl (535 mg, 2.1 mmol). The reaction mixture was poured into water and the product extracted into ethyl acetate (3×). The combined organic layers were dried (MgSO₄) and evaporated to give compound 322. Trifluoroacetic acid (excess) was added and the reaction mixture was stirred at RT to remove the Boc group. Following removal of volatile components under vacuum, the TFA salt of amine 323 was obtained, which was used without further purification.

Compound F-19

Acid 12 (628 mg, 1.5 mmol) and amine 323 (1.0 mmol) were coupled according to Procedure C using BOPCl (364 mg, 1.43 mmol). Purification according to Procedure E gave the product F-6.

EXAMPLE EE

This example illustrates the synthesis of compounds containing a 3-aminobenzoic acid moiety, as represented by compounds F-8, F-9 and F-10.

Scheme 35

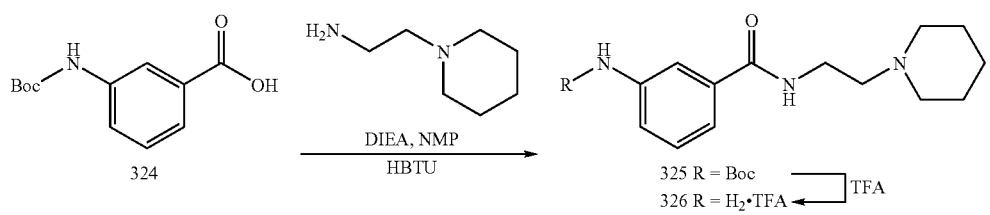

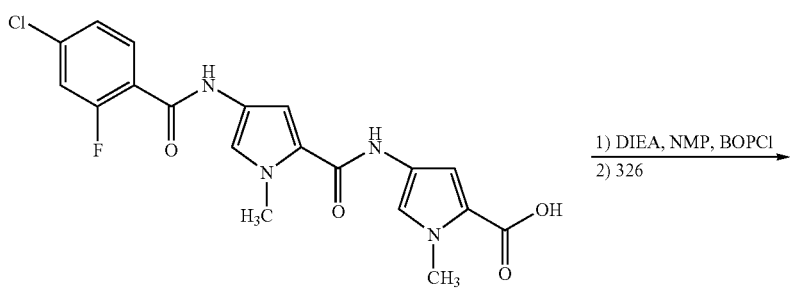

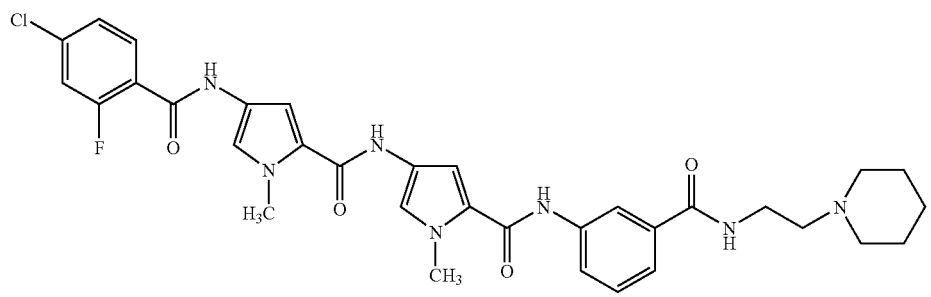

F-8

Compounds 325/326

Acid 324 (1.56 g, 6.6 mmol) and 1-(2-aminoethyl)piperidine (845 μl, 6.0 mmol) were coupled according to Procedure A using HBTU (2.28 g, 6.0 mmol). The reaction mixture was poured into water and the product extracted into ethyl acetate (3×). The combined organic layers were dried (MgSO₄) and evaporated to give compound 325. Excess TFA was added and the reaction stirred at room temperature to remove the Boc group. Following removal of volatile components under vacuum, the TFA salt of amine 326 was obtained and was used without further purification.

Compound F-8

Acid 12 (653 mg, 1.56 mmol) and amine 326 (1.2 mmol) were coupled according to Procedure C using BOPCl (321 mg, 1.26 mmol). Purification according to Procedure E gave the product F-8.

EXAMPLE FF

This example illustrates the synthesis of compounds containing a 2-amino-5-carboxypyridine moiety, as represented by compounds F-5 and F-7. Scheme 37 illustrates their synthesis by specific reference to compound F-7.

Scheme 36

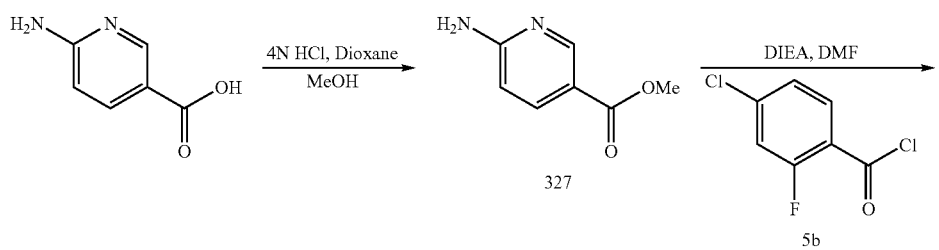

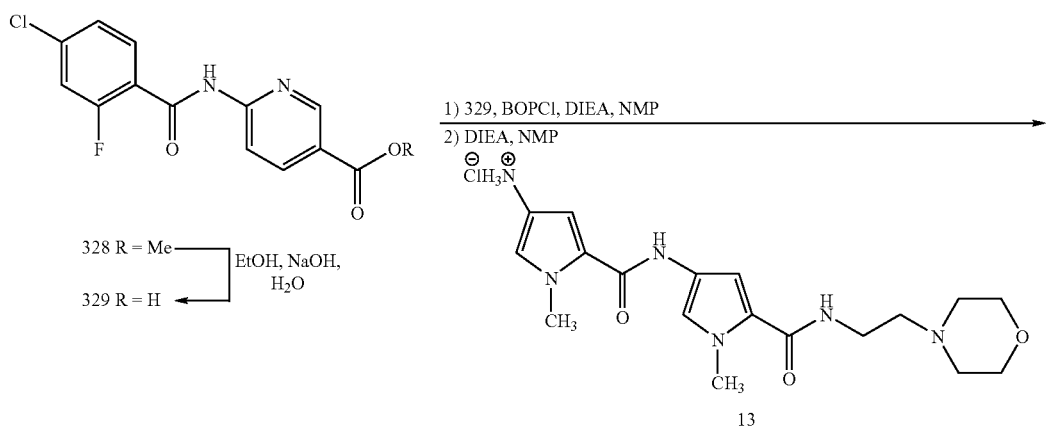

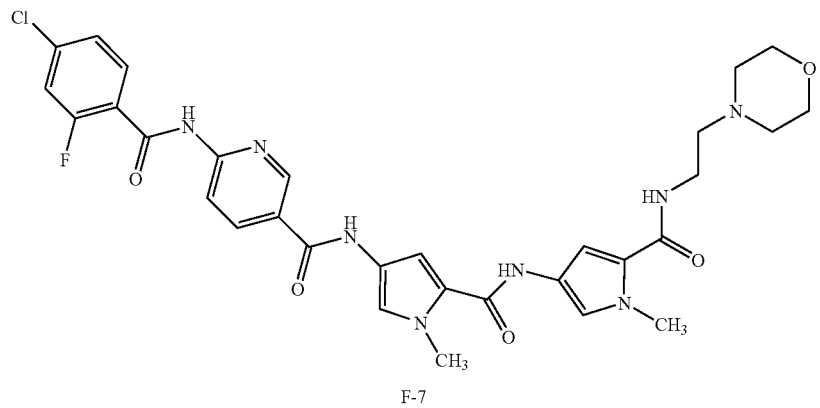

F-7

Compounds 328/329

6-Aminonicotinic acid (10 g, 72.4 mmol) in MeOH (55 mL) was treated with a 4N solution of HCl in dioxane (54 mL, 217 mmol). The reaction mixture was heated at reflux for 12 hours. Removal of volatile components under vacuum left amino ester 327 as a white solid. Amino ester 327 (411 mg, 2.7 mmol) and acid chloride 5b (2.84 mmol) were coupled using Procedures D and G to give product 328. Product 328 was saponified using Procedure H to give acid 329.

Compound F-7. Acid 329(103 mg, 0.35 mmol) and amine 13 (132 mg, 0.32 mmol) were coupled according to Procedure C using BOPCl (85 mg, 0.33 mmol). Purification according to Procedure E gave compound F-7.

EXAMPLE GG

Compounds such as A-31 to A-33 and C-21 to C-25, in which the N-terminal phenyl group has a pendant amine substituent, from the corresponding fluoro polyamide by nucleophilic aromatic substitution of the fluorine by the corresponding amine, using reaction conditions of 48 hr at 60-70° C. in NMP. For instance, the treatment of compound A-3 with 4-(2-aminoethyl)morpholine under such conditions gave compound A-31.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A compound having the formula

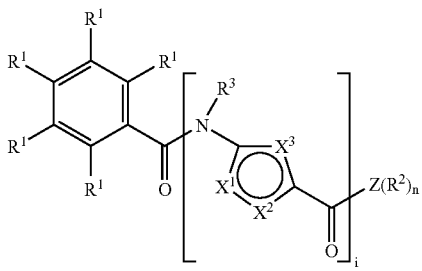

wherein i is 3;
one of $X^1$, $X^2$, and $X^3$ is a ring vertex selected from the group consisting of —O—, —S—, and —$NR^2$—, and the other two of $X^1$, $X^2$, and $X^3$ are ring vertices selected from the group consisting of =N— and =$CR^4$—, wherein each moiety

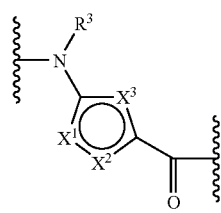

is the same or different and at least one moiety is other than

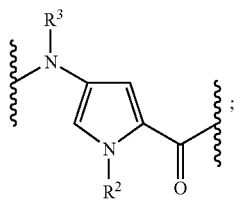

each $R^1$ is independently H, F, Cl, CN, $CF_3$, OH, $N(R^2)_2$, $OR^2$ or a substituted or unsubstituted $(C_1-C_{12})$alkyl group, with the proviso that at least one $R^1$ is F, Cl, CN or $CF_3$;
each $R^2$ and $R^3$ is independently H or a substituted or unsubstituted $(C_1-C_{12})$alkyl group;
each $R^4$ is independently H, F, Cl, Br, I, CN, OH, $NO_2$, $NH_2$, or a substituted or unsubstituted $(C_1-C_{12})$alkyl group;
$Z(R^2)_n$ is a member selected from the group consisting of:

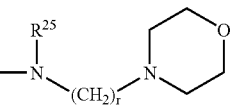

r is an integer ranging from 2 to 8, inclusive;
each $R^{25}$ is independently selected from the group consisting of H, $CH_3$, $CH_2CH_3$, $CH_2CH_2CH_3$, or $CH(CH_3)_2$;
said compound having at least one basic group having a $pK_b$ of 12 or less or a quaternized nitrogen group.

2. A compound according to claim 1, wherein

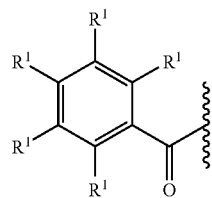

is selected from the group consisting of

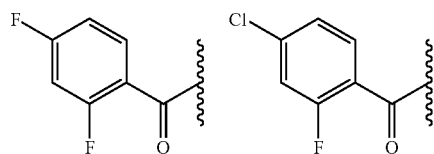

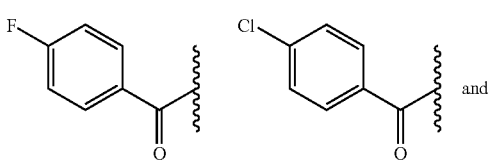

and

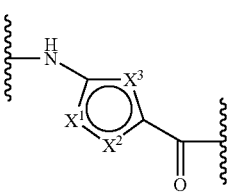

3. A compound according to claim 1, wherein the moiety

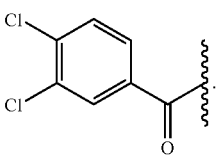

which is other than
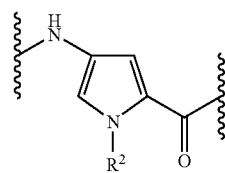
is selected from the group consisting of
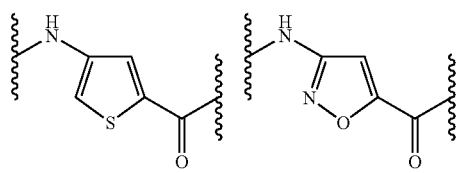
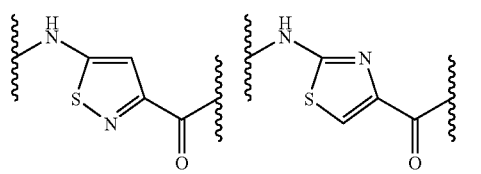
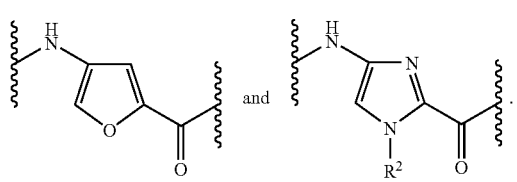 and
4. A compound according to claim 1, wherein each $R^1$ is independently H, F or Cl;
 i is 3;
 two of said moiety
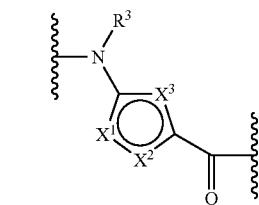
are
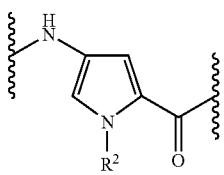
and one is
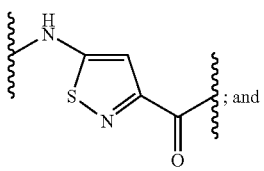 ; and
$Z(R^2)_n$ is
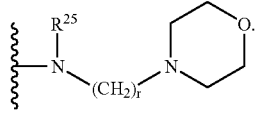
5. A compound according to claim 1, having the formula:
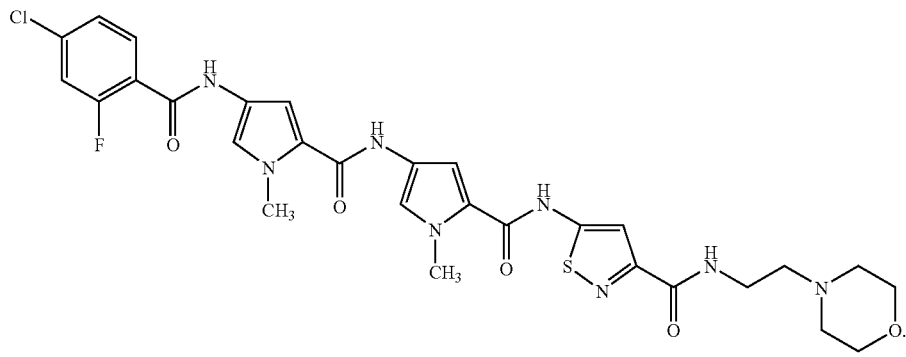
* * * * *